(12) United States Patent
Howard et al.

(10) Patent No.: US 9,399,073 B2
(45) Date of Patent: Jul. 26, 2016

(54) PYRROLOBENZODIAZEPINES

(71) Applicants: MEDIMMUNE LIMITED, Cambridge (GB); SEATTLE GENETICS, INC., Bothell, WA (US)

(72) Inventors: Philip Wilson Howard, London (GB); Arnaud Tiberghien, London (GB); Scott Jeffrey, Bothell, WA (US); Patrick Burke, Bothell, WA (US)

(73) Assignees: SEATTLE GENETICS, INC., Bothell, WA (US); MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/351,173

(22) PCT Filed: Oct. 12, 2012

(86) PCT No.: PCT/EP2012/070233
§ 371 (c)(1),
(2) Date: Apr. 11, 2014

(87) PCT Pub. No.: WO2013/053873
PCT Pub. Date: Apr. 18, 2013

(65) Prior Publication Data
US 2014/0274907 A1    Sep. 18, 2014

Related U.S. Application Data

(60) Provisional application No. 61/547,198, filed on Oct. 14, 2011.

(51) Int. Cl.
*C07D 487/04* (2006.01)
*A61K 47/48* (2006.01)
*C07D 519/00* (2006.01)
*C07H 15/22* (2006.01)

(52) U.S. Cl.
CPC ..... *A61K 47/48338* (2013.01); *A61K 47/48092* (2013.01); *C07D 487/04* (2013.01); *C07D 519/00* (2013.01); *C07H 15/22* (2013.01)

(58) Field of Classification Search
CPC ................................... C07D 487/04
See application file for complete search history.

(56) References Cited

U.S. PATENT DOCUMENTS

| | | | |
|---|---|---|---|
| 3,361,742 A | 1/1968 | Julius et al. |
| 3,523,941 A | 8/1970 | Leimgruber et al. |
| 3,524,849 A | 8/1970 | Batcho et al. |
| 3,794,644 A | 2/1974 | Karlyone et al. |
| 4,185,016 A | 1/1980 | Takanabe et al. |
| 4,239,683 A | 12/1980 | Takanabe et al. |
| 4,309,437 A | 1/1982 | Ueda et al. |
| 4,353,827 A | 10/1982 | Hunkeler et al. |
| 4,382,032 A | 5/1983 | Hunkeler et al. |
| 4,386,028 A | 5/1983 | Hunkeler et al. |
| 4,405,516 A | 9/1983 | Hunkeler et al. |
| 4,405,517 A | 9/1983 | Hunkeler et al. |
| 4,407,752 A | 10/1983 | Hunkeler et al. |
| 4,427,587 A | 1/1984 | Kaneko et al. |
| 4,427,588 A | 1/1984 | Kaneko et al. |
| 4,701,325 A | 10/1987 | Ueda et al. |
| 4,923,984 A | 5/1990 | Matsumura et al. |
| 5,418,241 A | 5/1995 | Jegham et al. |
| 6,362,331 B1 | 3/2002 | Kamal et al. |
| 6,562,806 B1 | 5/2003 | Thurston et al. |
| 6,608,192 B1 | 8/2003 | Thurston et al. |
| 6,660,742 B2 | 12/2003 | Lee et al. |
| 6,660,856 B2 | 12/2003 | Wang |
| 6,747,144 B1 | 6/2004 | Thurston et al. |
| 6,884,799 B2 | 4/2005 | Kamal et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,244,724 B2 | 7/2007 | Liu et al. |
| 7,265,105 B2 | 9/2007 | Thurston et al. |
| 7,407,951 B2 | 8/2008 | Thurston et al. |
| 7,429,658 B2 | 9/2008 | Howard et al. |
| 7,528,126 B2 | 5/2009 | Howard et al. |
| 7,557,099 B2 | 7/2009 | Howard et al. |
| 7,612,062 B2 | 11/2009 | Gregson et al. |
| 7,704,924 B2 | 4/2010 | Thurston et al. |
| 7,741,319 B2 | 6/2010 | Howard et al. |
| 8,034,808 B2 | 10/2011 | Delavault et al. |
| 8,163,736 B2 | 4/2012 | Gauzy et al. |
| 8,487,092 B2 | 7/2013 | Howard et al. |
| 8,501,934 B2 | 8/2013 | Howard et al. |
| 8,592,576 B2 | 11/2013 | Howard et al. |
| 8,633,185 B2 | 1/2014 | Howard et al. |
| 8,637,664 B2 | 1/2014 | Howard et al. |
| 8,697,688 B2 | 4/2014 | Howard et al. |
| 8,829,184 B2 | 9/2014 | Howard et al. |
| 8,940,733 B2 | 1/2015 | Howard et al. |
| 9,102,704 B2 | 8/2015 | Howard |
| 2003/0195196 A1 | 10/2003 | Thurston et al. |
| 2004/0138269 A1 | 7/2004 | Sun et al. |
| 2004/0198722 A1 | 10/2004 | Thurston et al. |
| 2007/0092940 A1 | 4/2007 | Eigenbrot et al. |
| 2007/0154906 A1 | 7/2007 | Martin et al. |
| 2007/0185336 A1 | 8/2007 | Rossen et al. |
| 2007/0191349 A1 | 8/2007 | Howard et al. |
| 2007/0232592 A1 | 10/2007 | Delavault et al. |
| 2007/0249591 A1 | 10/2007 | Howard et al. |
| 2008/0090812 A1 | 4/2008 | Pepper et al. |
| 2008/0092940 A1 | 4/2008 | Nakajima |
| 2008/0213289 A1 | 9/2008 | Francisco et al. |
| 2009/0148942 A1 | 6/2009 | Mcdonagh et al. |
| 2011/0160192 A1 | 6/2011 | Howard et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2013/0028917 A1 | 1/2013 | Howard et al. |
| 2013/0028919 A1 | 1/2013 | Howard et al. |
| 2013/0035484 A1 | 2/2013 | Howard et al. |
| 2013/0266595 A1 | 10/2013 | Flygare et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0120118 A1 | 5/2014 | Howard |
| 2014/0127239 A1 | 5/2014 | Howard |
| 2014/0234346 A1 | 8/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |

| | | | | | |
|---|---|---|---|---|---|
| 2015/0344482 A1 | 12/2015 | Howard et al. | WO | WO 2014/057122 | 4/2014 |
| 2016/0015828 A1 | 1/2016 | Torgov | WO | WO 2014/022679 | 6/2014 |
| 2016/0031887 A1 | 2/2016 | Howard et al. | WO | WO 2014/096365 | 6/2014 |
| | | | WO | WO 2014/096368 | 6/2014 |

FOREIGN PATENT DOCUMENTS

| | | |
|---|---|---|
| WO | WO 2014/130879 | 8/2014 |
| WO | WO 2014/140174 | 9/2014 |
| WO | WO 2014/140862 | 9/2014 |
| EP | 1813614 | 8/2007 |
| WO | WO 2014/159981 | 10/2014 |
| FR | 2027356 | 12/1969 |
| WO | WO 2014/174111 | 10/2014 |
| FR | 2586683 | 3/1987 |
| WO | WO 2013/053872 | 4/2015 |
| GB | 1299198 | 12/1972 |
| WO | WO 2015/052321 | 4/2015 |
| GB | 2053894 | 2/1981 |
| WO | WO 2015/052322 | 4/2015 |
| JP | 53-82792 | 7/1978 |
| WO | WO 2015/052532 | 4/2015 |
| JP | 57131791 | 8/1982 |
| WO | WO 2015/052533 | 4/2015 |
| JP | 58180487 | 10/1983 |
| WO | WO 2015/052534 | 4/2015 |
| WO | WO 92/19620 | 11/1992 |
| WO | WO 2015/052535 | 4/2015 |
| WO | WO 93/18045 | 9/1993 |
| WO | WO 2015/095124 | 6/2015 |
| WO | WO 95/04718 | 2/1995 |
| WO | 2015/159076 | 10/2015 |
| WO | WO 00/03291 | 1/2000 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 01/16104 | 3/2001 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/082023 | 9/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/085930 | 8/2007 |
| WO | WO 2008/010101 | 1/2008 |
| WO | WO 2008/047242 | 4/2008 |
| WO | WO 2008/050140 | 5/2008 |
| WO | WO 2008/070593 | 6/2008 |
| WO | WO 2009/016516 | 2/2009 |
| WO | WO 2009/060208 | 5/2009 |
| WO | WO 2009/060215 | 5/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/038159 | 3/2011 |
| WO | WO 2011/100227 | 8/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053872 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/164592 | 11/2013 |
| WO | WO 2013/164593 | 11/2013 |
| WO | WO 2014/011518 | 1/2014 |
| WO | WO 2014/011519 | 1/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/057114 | 4/2014 |
| WO | WO 2014/057115 | 4/2014 |
| WO | WO 2014/057117 | 4/2014 |
| WO | WO 2014/057118 | 4/2014 |
| WO | WO 2014/057119 | 4/2014 |
| WO | WO 2014/057120 | 4/2014 |

OTHER PUBLICATIONS

Adair, J.R. et al., "Antibody-drug conjugates—a perfect synergy," Exp. Opin. Biol. Ther. (2012) 16 pages.

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird, R.E. et al., "ABCB1 genetic polymorphism influences the pharmacology of the new pyrrolobenzodiazepine derivative SJG-136," Pharmacogenomics Journal (2008) 8(4):289-296.

Alley, M.C. et al., "SJG-136 (NSC 694501), a novel rationally designed DNA minor groove interstrand cross-linking agent with potent and broad spectrum antitumor activity. Part 2: Efficacy evaluations," Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Althius, T. H. and Hess, H. J., "Synthesis and Identification of the Major Metabolites of Prazosin Formed in Dog and Rat," J. Medicinal Chem. (1977) 20(1):146-148.

Antonow, D. et al.,"Parallel synthesis of a novel C2-aryl pyrrolo[2,1-c][1,4]benzodiazepine (PBD) library," J. Comb. Chem. (2007) 9:437-445.

Arima et al., "Studies on Tomaymycin, a New Antibiotic. I. Isolation and Properties of Tomaymycin," J. Antibiotics (1972) 25:437-444.

Arnould, S., "Impact on the cell cycle and involvement of ATM, ATR, chk1 and chk2 kinases in the cytotoxicity of SJG-136, a new pyrrolobenzodiazepine dimer," Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. (2006) 5(6):1602-1609.

Banker, G.S. et al., Modern Pharmaceutics, Third edition, Marcel Dekker, New York (1996) 451 and 596.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters (2000) 41:6171-6174.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.

Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.

Burke, P.J. et al., "Novel immunoconjugates comprised of streptonigrin and 17-amino-geldanamycin attached via a dipeptide-p-aminobenzyl-amine linker system," Bioorg. Med. Chem. Lett., Apr. 2009, 19(10):2650-2653.

Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cheung, A., "Direct liquid chromatography determination of the reactive imine SJG-136 (NSC 694501)," J. Chromat. B: Anal. Techn. Biomed. Life Sci. (2005) 822(1-2):10-20.

Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.

Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.

Clingen, P.H., "The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Courtney, S. M. et al., "A new convenient procedure for the synthesis of pyrrolo[2,1-c][1,4]benzodiazepines", Tetrahedron Letters, vol. 34, No. 33, 5327-28 (1993).

Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.

Dong, Q. et al., "Reductive cleavage of TROC groups under neutral conditions with cadmium-lead couple," Tetrahedron Lett. (1995) 36(32):5681-5682.

Doronina, S.O. et al., "Development of potent monoclonal antibody auristatin conjugates for cancer therapy," Nature Biotech. (2003) 21:778-784.

Dorwald, F.Z., Side Reactions in Organic Synthesis: a Guide to Successful Synthesis Design, Weinheim: Wiley-VCH Verlag GmbH & Co., KGaA (2005) Preface.

Doyle, M., "Response of Staphylococcus aureus to subinhibitory concentrations of a sequence-selective, DNA minor groove cross-linking pyrrolobenzodiazepine dimer," J. Antimicrob. Chemo., Aug. 2009, 64(5):949-959.

Dupont, C. et al., "Synthesis of rhazinilam analogue acting as an inhibitor of tubulin assembly," Tetrahedron Lett. (2000) 41:5853-5856.

Farmer, J.D. et al., "Synthesis and DNA crosslinking ability of a dimeric anthramycin analog," Tetrahedron Letters (1988) 29(40):5105-5108, Abstract only.

Farmer, J.D. et al., "DNA binding properties of a new class of linked anthramycin analogs,", Chemical Abstracts, Abstract No. 239940r, vol. 114, No. 25, 25 899-903 (1991).

Fey, T. et al., "Silica-supported TEMPO catalyst: synthesis and application in the anelli oxidation of alcohols," J. Org. Chem. (2001) 66:8154-8159.

Firsching, A. et al., "Antiproliferative and angiostatic activity of suramin analogues," Cancer Res. (1995) 55:4957-4961.

Foloppe, M.P. et al., "DNA-binding properties of pyrrolo[2,1-c][1,4]benzodiazephine N10-C11 amidines," Eur. J. Med. Chem., 31, 407-410 (1996).

Fujisawa Pharmaceutical Co., Ltd., Abstract No. 139983k, "Benzodiazepine derivatives", Chemical Abstracts, vol. 99, No. 17, 603 (1983).

Fujisawa Pharmaceutical Co., Ltd., Abstract No. 72145x, "Benzodiazepine derivatives", Chemical Abstracts, vol. 98, No. 9, 638 (1983).

Fukuyama, T. et al., "Total Synthesis of (+)-Porothramycin B," Tetrahedron Letters, vol. 34, 16, 2577-2580 (1993).

Gallmeier, E., "Targeted disruption of FANCC and FANCG in human cancer provides a preclinical model for specific therapeutic options," Gastroenterology (2006) 130(7):2145-2154.

Gavezzotti, A., "Are crystal structures predictable?" Acc. Chem. Res. (1994) 27:309-314.

Greene, T.W. and Wuts, P.G.M., Protective Groups in Organic Synthesis, John Wiley & Sons, 2nd ed., Ch 7, 315-345 (1991).

Greene, T.W. et al., Protective Groups in Organic Synthesis, John Wiley & Sons (1999) 3rd Edition, 23-200, 503-549, 633-647.

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).

Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).

Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.

Guiotto, A. et al., "Synthesis of novel C7-aryl substituted pyrrolo[2,1-c][1,4]benzodiazepines (PBDs) via Pro-N10-trot protection and suzuki coupling," Bioorganic & Medicinal Chemistry Letters, 8, No. 21, 3017-3018 (1998).

Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.

Hadjivassileva, T., "Interactions of pyrrolobenzodiazepine dimers and duplex DNA from methicillin-resistant Staphylococcus aureus," Int. J. Antimicrob. Agents (2007) 29(6):672-678.

Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.

Hamaguchi, A., "DNA cross-linking and in vivo antitumour activity of the extended pyrrolo[2,1-c][1,4]benzodiazepine dimer SG2057 (DRG-16)," EJC Supplements (Nov. 2006) 4(12):96.

Hara et al., "DC 102, a new glycosidic pyrrolo(1,4)benzodiazepine antibiotic produced by Streptomyces sp.", J. Antibiotics, 41, 702-704 (1988).

Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.

Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.

Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.

Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.

Hochhauser, D., "Phase I study of sequence-selective minor groove DNA binding agent SJG-136 in patients with advanced solid tumors," Clin. Cancer Res., Mar. 2009, 15(6):2140-2147.

Hochlowski, J. et al., "Abbeymycin, a new anthramycin-type antibiotic produced by a streptomycete," *J. Antibiotics*, 40, 145-148 (1987).

Howard, P.W. et al., "Design, synthesis and biological evaluation of ZC-423, a novel C2-aryl substituted pyrrolobenzodiazepine (PBD) dimer," Clinical Cancer Research (2005) 11(23):90155-90165 (A205).

Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages. now: Sep. 2009, 19:6463-6466.

Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.

Howard, P.W., "Design, synthesis and biological evaluation of novel C2-aryl-substituted pyrrolo[2,1-c][1,4]benzodiazepine monomers," Proceedings of the American Association for Cancer Research Annual Meeting (Apr. 2006) 47:132.

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *Micromonospora* sp." *J. Antibiotics*, 41, 1281-1284 (1988).

Janjigian, Y.Y., "A phase I trial of SJG-136 (NSC#694501) in advanced solid tumors," Cancer Chemotherapy and Pharmacology, Aug. 2009, 65(5):833-838.

Jeffrey, S.C., "Design, synthesis, and in vitro evaluation of dipeptide-based antibody minor groove binder conjugates," J. Med. Chem. (2005) 48(5):1344-1358.

Jia, L., "Interspecies differences in pharmacokinetics and time-dissociated toxicokinetics of SJG-136," Proceedings of the American Association for Cancer Research Annual Meeting (Mar. 2004) 45:487.

Jia, L., "Use of the comet assay as a surrogate biomarker for the in vivo measurement of DNA damage to lymphocytes," Proceedings of the American Association for Cancer Research Annual Meeting (Mar. 2004) 45:452-453.

Jordan, V.C., "Tamoxifen: a most unlikely pioneering medicine," Nature Reviews: Drug Discovery (2003) 2:205-213.

Kamal et al., "Synthesis and DNA-binding affinity of A-C8/C-C2 alkoxyamido-linked pyrrolo[2,1-c][1,4]benzodiazepine dimers" Biorg. Med. Chem. Left. (2003) 13(22):3955-3958.

Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.

Kamal, A., "Development of pyrrolo[2,1-c][1,4]benzodiazepine beta-galactoside prodrugs for selective therapy of cancer by ADEPT and PMT," Chemmedchem (2008) 3:794-802.

Kamal, A., "Remarkable DNA binding affinity and potential anticancer activity of pyrrolo[2,1-c][1,4]benzodiazepine-naphthalamide conjugates linked through piperazine side-armed alkane spacers," Bioorg. Med. Chem. (2008) 16(15):7218-7224.

Kamal, A., "Remarkable enhancement in the DNA-binding ability of C2-fluoro substituted pyrrolo[2,1-c][1,4]benzodiazepines and their anticancer potential," Bioorg. Med. Chem., Jan. 2009, 17(4):1557-1572.

Kamal, A., "Synthesis of fluorinated analogues of SJG-136 and their DNA-binding potential," Bioorg. Med. Chem. Left (2004) 14(22):5699-5702.

Kamal, A., et al., "An Efficient Synthesis of Pyrrolo[2,1-c][1,4] Benzodiazepine Antibiotics via Reductive Cyclization," *Bioorg. Med. Chem. Ltrs*, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kunimoto et al., "Mazethramycin, a new member of anthramycin group antibiotics," *J Antibiotics*, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," *J. Org. Chem.*, 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Marin, D., "Voltammetric studies of the interaction of pyrrolo[2,1-c][1,4]benzodiazepine (PBD) monomers and dimers with DNA," J. Electroanal. Chem. (2006) 593(1-2):241-246.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomaymycin adduct," J. Med. Chem. (1994) 37:3132-3140.

Nagasaka, T. and Koseki, Y, "Stereoselective Synthesis of Tilivalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

Narayanaswamy, M., "A novel HPLC/MS assay to measure DNA interstrand cross-linking efficacy in oligonucleotides of varying sequence," EJC Supplements (Nov. 2006) 4(12):92-93.

Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.

Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A., et al., "The Synthesis of Functionalized Pyrrolo-[2,1-c][1,4]-Benzodiazepines," Synlett, 75-78 (1997).

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.

Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.

Puzanov, I., "Phase I and pharmacokinetic trial of SJG-136 administered on a daily x5 schedule," EJC Supplements (Nov. 2006) 4(12):93.

Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.

Rahman, K.M., "Effect of microwave irradiation on covalent ligand-DNA interactions," Chem. Commun. (Cambridge, UK), Apr. 2009, 20:2875-2877.

Rahman, K.M., "Rules of DNA adduct formation for pyrrolobenzodiazepine (PBD) dimers," Proceedings of the American Association for Cancer Research Annual Meeting (Apr. 2010) 51:851.

Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.

Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.

Rich, I.N., "Validation and development of a predictive paradigm for hemotoxicology using a multifunctional bioluminescence colony-forming proliferation assay," Toxicological Sci. (2005) 87(2):427-441.

Sagnou, M.J. et al., "Design and Synthesis of Novel Pyrrolobenzodiazepine (PDB) Prodrugs for ADEPT and GDEPT,"Bioorganic & Medicinal Chemistry Letters, 10, 2083-2086 (2000).

Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.

Shimizu, K et al., "Prothracarcin, a Novel Antitumor Antibiotic," J. Antibiotics, 35, 972-978 (1982).

Smellie, M. et al., "Cellular pharmacology of novel C8-linked anthramycin-based sequence-selective DNA minor groove cross-linking agents," Br. J. Cancer (1994) 70:48-53.

Smellie, M. et al., "Sequence selective recognition of duplex DNA through covalent interstrand cross-linking," Biochem. (2003) 42:8232-8239.

Souillac, P. et al., "Chracterization of delivery systems, differential scanning calorimetry," Encyclopedia of Controlled Drug Delivery (1999) 212-227 (pp. 217-218).

Suggitt, M., "The hollow fibre model—facilitating anti-cancer preclinical pharmacodynamics and improving animal welfare," Int. J. Oncol. (2006) 29(6):1493-1499.

Suggs, J.W. et al., "Synthesis and structure of anthramycin analogs via hydride reduction of dilactams," Tetrahedron Letters, 26, No. 40, 4871-4874 (1985).

Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.

Takeuchi, T. et al., "Neothramycins A and B, New Antitumor Antibiotics," J Antibiotics, 29, 93-96 (1976).

Tercel, M. et al., "Unsymmetrical DNA cross-linking agents: combination of the CBI and PBD pharmacophores," J. Med. Chem. (2003) 46:2132-2151.

Thurston, D. E., "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).

Thurston, D.E. and Bose, D.S., "Synthesis of DNA-Interactive Pyrrolo[2,1-c][1,4]benzodiazepines," Chem. Rev., 94:433-465 (1994).

Thurston, D.E. and Thompson, A.S., "The molecular recognition of DNA," Chem. Brit., 26, 767-772 (1990).

Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," J Org. Chem., 61:8141-8147 (1996).

Thurston, D.E. et al., "Synthesis of a novel GC-specific covalent-binding DNA affinity-cleavage agent based on pyrrolobenzodiazepines (PBDs)," Chemical Communications, 563-565 (1996).

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.

Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.

Tozuka et al., "Studies on tomaymycin. II. Total synthesis of the antitumor antibiotics, E-and Z-tomaymycins," J. Antibiotics (Tokyo) (1983) 36:276-282.

Tsunakawa, M. et al., "Porothramycin, a new antibiotic of the anthramycin group: Production, isolation, structure and biological activity," J. Antibiotics, 41:1366-1373 (1988).

Umezawa, H. et al., Chemical Abstract No. 4427a, "Mazethramycins" Chemical Abstracts, vol. 90, No. 1, 428 (1979).

Vippagunta, S.R. et al., "Crystalline solids," Adv. Drug Delivery Rev. (2001) 48:3-26.

Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.

Weidner-Wells, M.A. et al., "Photochemical approach to the synthesis of the pyrrolo[1,4]benzodiazepine antibiotics," J. Org. Chem. (1989) 54:5746-5758.

Wells, G. et al., "Design, synthesis and biophysical and biological evaluation of a series of pyrrolobenzodiazepine-poly(N-methylpyrrole) conjugates," J. Med. Chem. (2006) 49:5442-5461.

(56) References Cited

OTHER PUBLICATIONS

Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42:4028-4041 (1999).
Wolff, M.E., Burger's Medicinal Chemistry, 4th Edition, Part I, Wiley: New York (1979) 336-337.
Wolff, M.E., Burger's Medicinal Chemistry, 5th Edition, Part I, John Wiley & Sons (1995) 975-977.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
Antonow, D. et al., "Synthesis of DNA-Interactive Pyrrolo [2,1-c][1,4] benzodiazepines (PBDs)" Chemical Reviews, 2011, 111(4):2815-2864.
Shimizu et al., "Prothracarcin, a novel antitumor antibiotic," The Journal of Antibiotics (1982) 29, 2492-2503.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Bioconjugate Chem. (2002) 13, 855-869.
International Search Report and Written Opinion for Application No. PCT/US2011/032664 dated Aug. 19, 2011 (13 pages).
International Search Report and Written Opinion for Application No. PCT/EP2012/070233 dated Jan. 28, 2013 (8 pages).
U.S. Appl. No. 14/774,535, Howard et al., filed Sep. 10, 2015.
U.S. Appl. No. 14/995,944, Howard et al., filed Jan. 14, 2016.

*Primary Examiner* — Bruck Kifle

(74) *Attorney, Agent, or Firm* — Michael Best & Friedrich LLP

(57) ABSTRACT

A compound with the formula (I), wherein: $R^2$ is of formula (II), where X is selected from the group comprising: OH, SH, $CO_2H$, COH, N=C=O, $NHNH_2$, $CONHNH_2$, formula (A), formula (B), $NHR^N$, wherein $R^N$ is selected from the group comprising H and $C_{1-4}$ alkyl; $R^{C1}$, $R^{C2}$ and $R^{C3}$ are independently selected from H and unsubstituted $C_{1-2}$ alkyl; and either: $R^{12}$ is selected from the group consisting of: (ia) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene; (ib) $C_{1-5}$ saturated aliphatic alkyl; (ic) $C_{3-6}$ saturated cycloalkyl; (id) formula (C), wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5; (ie) formula (D), wherein one of $R^{25a}$ and $R^{25b}$ is H and the other is selected from: phenyl, which phenyl is optionally substituted by a group selected from halo, methyl, methoxy; pyridyl; and thiophenyl; and (if) formula (E), where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl; $R^6$ and $R^9$ are independently selected from H, R, OH, OR, SH, SR, $NH_2$, NHR, NRR', nitro, $Me_3Sn$ and halo; where R and R' are independently selected from optionally substituted $C_{1-12}$ alkyl, $C_{3-20}$ heterocyclyl and $C_{5-20}$ aryl groups; $R^7$ is selected from H, R, OH, OR, SH, SR, $NH_2$, NHR, NHRR', nitro, $Me_3Sn$ and halo; either: (a) $R^{10}$ is H, and $R^{11}$ is OH, $OR^A$, where $R^A$ is $C_{1-4}$ alkyl; (b) $R^{10}$ and $R^{11}$ form a nitrogen-carbon double bond between the nitrogen and carbon atoms to which they are bound; or (c) $R^{10}$ is H and $R^{11}$ is $SO_zM$, where z is 2 or 3 and M is a monovalent pharmaceutically acceptable cation; R" is a $C_{3-12}$ alkylene group, which chain may be interrupted by one or more heteroatoms, and/or aromatic rings; Y and Y' are selected from O, S, or NH; $R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, wherein if $R^{11}$ and $R^{11'}$ are $SO_zM$, M may represent a divalent pharmaceutically acceptable cation.

(I)

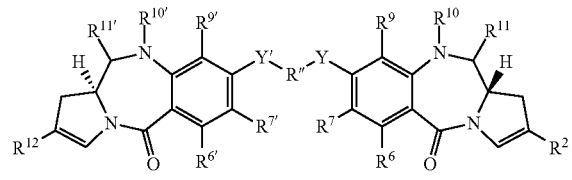

(II)

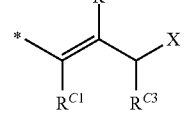

(A)

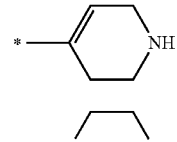

(B)

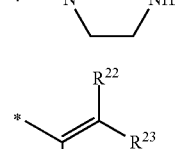

(C)

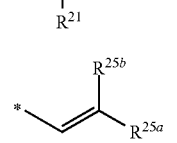

(D)

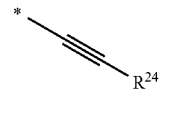

(E)

17 Claims, No Drawings

PYRROLOBENZODIAZEPINES

CROSS-REFERENCE TO RELATED APPLICATIONS

This application is a national stage filing under 35 U.S.C. 371 of International Application No. PCT/EP2012/070233 filed Oct. 12, 2012, and claims the benefit of U.S. Provisional Application No. 61/547,198 filed Oct. 14, 2011, which is incorporated by reference herein.

The present invention relates to pyrrolobenzodiazepines (PBDs), in particular pyrrolobenzodiazepine dimers having one monomer unit with a C2-C3 double bond and an aryl group at the C2 position and the second monomer unit with a C2-C3 double bond and a substituted propylene group at the C2 position, and their inclusion in targeted conjugates.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and numerous synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

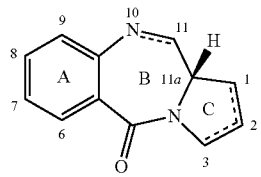

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDeventer, *Acc. Chem. Res.*, 19, 230-237 (1986)). Their ability to form an adduct in the minor groove, enables them to interfere with DNA processing, hence their use as antitumour agents.

It has been previously disclosed that the biological activity of these molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity. One example of a PBD dimmer, SG2000 (SJG-136):

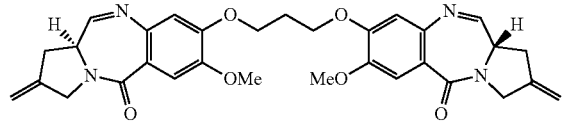

has recently entered Phase II clinical trials in the oncology area (Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)).

More recently, the present inventors have previously disclosed in WO 2005/085251, dimeric PBD compounds bearing C2 aryl substituents, such as SG2202 (ZC-207):

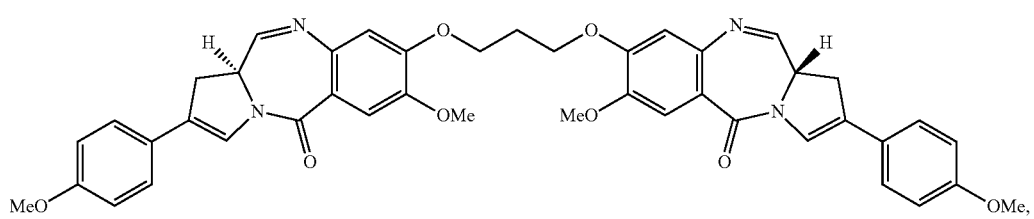

and in WO2006/111759, bisulphites of such PBD compounds, for example SG2285 (ZC-423):

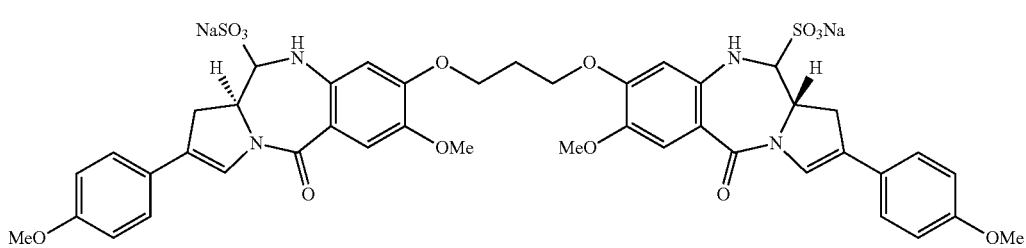

These compounds have been shown to be highly useful cytotoxic agents (Howard, P. W., et al., *Bioorg. Med. Chem.* (2009), 19 (22), 6463-6466, doi: 10.1016/j.bmcl.2009.09.012).

Due to the manner in which these highly potent compounds act in cross-linking DNA, these molecules have been made symmetrically. This provides for straightforward synthesis, either by constructing the PBD moieties simultaneously having already formed the dimer linkage, or by reacting already constructed PBD moieties with the dimer linking group.

WO 2010/043880 discloses unsymmetrical dimeric PBD compound bearing aryl groups in the C2 position of each monomer, where one of these aryl groups bears a substituent designed to provide an anchor for linking the compound to another moiety. Co-pending International application PCT/US2011/032664, filed 15 Apr. 2011, published as WO 2011/130613, discloses the inclusion of these PBD dimer compounds in targeted conjugates. Co-pending International application PCT/US2011/032668, filed 15 Apr. 2011, published as WO 2011/130616, discloses unsymmetrical dimeric PBD compound bearing an aryl group in the C2 position of one monomer bearing a substituent designed to provide an anchor for linking the compound to another moiety, the other monomer bearing a non-aromatic group in the C2 position. The inclusion of these compounds in targeted conjugates is also disclosed.

DISCLOSURE OF THE INVENTION

The present inventors have developed further unsymmetrical dimeric PBD compounds for inclusion in targeted conjugates, eliminating the need for an aryl group bearing an anchor. The C2 group bearing a substituent designed to provide an anchor for linking the compound to another moiety in the present invention is a propylene group. These compounds may be easier to synthesise and have advantages in their use, particularly in their biological properties and the synthesis of conjugates, and the biological properties of these conjugates.

The present invention comprises a compound with the formula I:

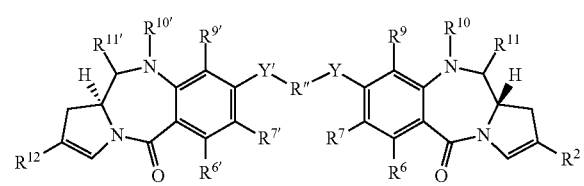

or a pharmaceutically acceptable salt or solvate thereof, wherein:
$R^2$ is of formula II:

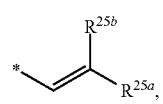

where X is selected from the group comprising: OH, SH, $CO_2H$, COH, N=C=O, $NHNH_2$, $CONHNH_2$,

[two cyclic structures: *—cyclohexenyl-NH, *—N-piperazinyl-NH]

$NHR^N$, wherein $R^N$ is selected from the group comprising H and $C_{1-4}$ alkyl;
$R^{C1}$, $R^{C2}$ and $R^{C3}$ are independently selected from H and unsubstituted $C_{1-2}$ alkyl;
and either:
$R^{12}$ is selected from the group consisting of:
(ia) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;
(id)

[structure with $R^{22}$, $R^{21}$, $R^{23}$]

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5; (ie)

[structure with $R^{25b}$, $R^{25a}$]

wherein one of $R^{25a}$ and $R^{25b}$ is H and the other is selected from: phenyl, which phenyl is optionally substituted by a group selected from halo, methyl, methoxy; pyridyl; and thiophenyl; and (if)

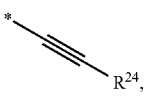

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo; either:

(a) $R^{10}$ is H, and $R^{11}$ is OH, $OR^A$, where $R^A$ is $C_{1-4}$ alkyl; or (b) $R^{10}$ and $R^{11}$ form a nitrogen-carbon double bond between the nitrogen and carbon atoms to which they are bound; or (c) $R^{10}$ is H and $R^{11}$ is $SO_zM$, where z is 2 or 3 and M is a monovalent pharmaceutically acceptable cation;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, wherein if $R^{11}$ and $R^{11'}$ are $SO_zM$, M may represent a divalent pharmaceutically acceptable cation.

A second aspect of the present invention provides the use of a compound of the first aspect of the invention in the manufacture of a medicament for treating a proliferative disease. The second aspect also provides a compound of the first aspect of the invention for use in the treatment of a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

A third aspect of the present invention comprises a compound of formula II:

II

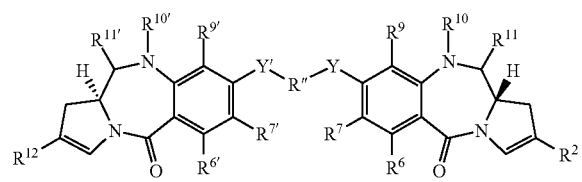

or a pharmaceutically acceptable salt or solvate thereof, wherein:

$R^2$ is of formula II:

II

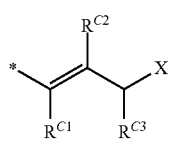

where X is selected from the group comprising: OH, SH, $CO_2H$, COH, N=C=O, $NHNH_2$, $CONHNH_2$,

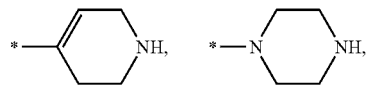

$NHR^N$, wherein $R^N$ is selected from the group comprising H and $C_{1-4}$ alkyl, and either:

$R^{12}$ is selected from the group consisting of:

(ia) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

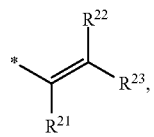

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

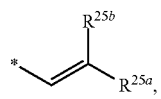

wherein one of $R^{25a}$ and $R^{25b}$ is H and the other is selected from: phenyl, which phenyl is optionally substituted by a group selected from halo, methyl, methoxy; pyridyl; and thiophenyl; and (if)

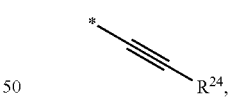

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

(a) $R^{10}$ is carbamate nitrogen protecting group, and $R^{11}$ is O-$Prot^O$, wherein $Prot^O$ is an oxygen protecting group; or (b) $R^{10}$ is a hemi-aminal nitrogen protecting group and $R^{11}$ is an oxo group;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine; Y and Y' are selected from O, S, or NH;

$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$.

A fourth aspect of the present invention comprises a method of making a compound of formula I, or a pharmaceutically acceptable salt or solvate thereof, from a compound of formula II, or a pharmaceutically acceptable salt or solvate thereof, by deprotection of the imine bond.

The unsymmetrical dimeric PBD compounds of the present invention are made by different strategies to those previously employed in making symmetrical dimeric PBD compounds. In particular, the present inventors have developed a method which involves adding each each C2 substituent to a symmetrical PBD dimer core in separate method steps. Accordingly, a fifth aspect of the present invention provides a method of making a compound of the first or third aspect of the invention, comprising at least one of the method steps set out below.

In a sixth aspect, the present invention relates to Conjugates comprising dimers of PBDs linked to a targeting agent, wherein the PBD dimer is of formula I, or a pharmaceutically acceptable salt or solvate thereof (supra).

In some embodiments, the Conjugates have the following formula III:

$$L\text{-}(LU\text{-}D)_p \quad (III)$$

or a pharmaceutically acceptable salt or solvate thereof, wherein L is a Ligand unit (i.e., a targeting agent), LU is a Linker unit and D is a Drug unit that is a PBD dimer (see below). The subscript p is an integer of from 1 to 20. Accordingly, the Conjugates comprise a Ligand unit covalently linked to at least one Drug unit by a Linker unit. The Ligand unit, described more fully below, is a targeting agent that binds to a target moiety. The Ligand unit can, for example, specifically bind to a cell component (a Cell Binding Agent) or to other target molecules of interest. Accordingly, the present invention also provides methods for the treatment of, for example, various cancers and autoimmune disease. These methods encompass the use of the Conjugates wherein the Ligand unit is a targeting agent that specifically binds to a target molecule. The Ligand unit can be, for example, a protein, polypeptide or peptide, such as an antibody, an antigen-binding fragment of an antibody, or other binding agent, such as an Fc fusion protein.

In conjugates of the present invention, the PBD dimer D is of formula I, or a pharmaceutically acceptable salt or solvate thereof, except that X is selected from the group comprising: *—O—+, *—S—+, *—$CO_2$—+, *—CO—+, *—NH(C=O)—+, *—NHNH—+, *—CONHNH—+,

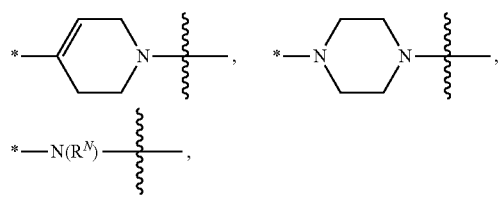

wherein $R^N$ is selected from the group comprising H and $C_{1-4}$ alkyl, and the asterix indicates the point of attachment to the remainder of the Drug unit and the wavy line or + indicates the point of attachment to the Linker Unit.

The drug loading is represented by p, the number of drug molecules per Ligand unit (e.g., an antibody). Drug loading may range from 1 to 20 Drug units (D) per Ligand unit (e.g., Ab or mAb). For compositions, p represents the average drug loading of the Conjugates in the composition, and p ranges from 1 to 20.

In some embodiments, p is from about 1 to about 8 Drug units per Ligand unit. In some embodiments, p is 1. In some embodiments, p is 2. In some embodiments, p is from about 2 to about 8 Drug units per Ligand unit. In some embodiments, p is from about 2 to about 6, 2 to about 5, or 2 to about 4 Drug units per Ligand unit. In some embodiments, p is about 2, about 4, about 6 or about 8 Drug units per Ligand unit.

The average number of Drugs units per Ligand unit in a preparation from a conjugation reaction may be characterized by conventional means such as mass spectroscopy, ELISA assay, and HPLC. The quantitative distribution of Conjugates in terms of p may also be determined. In some instances, separation, purification, and characterization of homogeneous Conjugates, where p is a certain value, from Conjugates with other drug loadings may be achieved by means such as reverse phase HPLC or electrophoresis.

In a seventh aspect, the present invention relates to Linker-Drug compounds (i.e., Drug-Linkers) comprising dimers of PBDs (see above) linked to a linking unit. These Drug-linkers can be used as intermediates for the synthesis of Conjugates comprising dimers of PBDs linked to a targeting agent.

These Drug-Linkers have the following formula V:

$$LU\text{-}D \quad (V)$$

or a pharmaceutically acceptable salt or solvate thereof, wherein LU is a Linker unit and D is a Drug unit that is a PBD dimer.

In the Drug-Linkers of the present invention, the PBD dimer D is of formula I, or a pharmaceutically acceptable salt or solvate thereof, except that X is selected from the group comprising: *—O—$^q$, *—S—$^q$, *—$CO_2$—$^q$, *—CO—$^q$q, *—NH(C=O)—$^q$, *—NHNH—$^q$, *—CONHNH—$^q$,

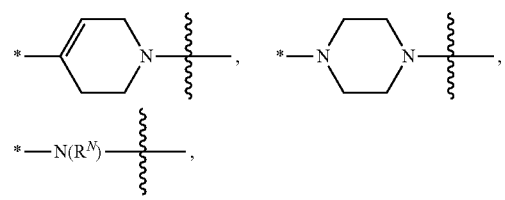

wherein $R^N$ is selected from the group comprising H and $C_{1-4}$ alkyl, and the asterix indicates the point of attachment to the remainder of the Drug unit and the wavy line or q indicates the point of attachment to the Linker Unit.

DEFINITIONS

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference. The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$.

Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.
Thione (thioketone): =S.
Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

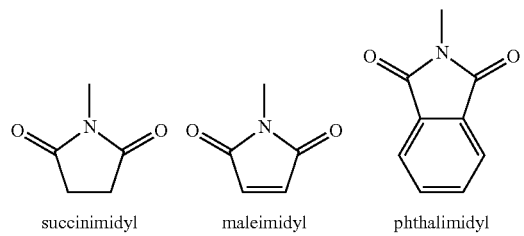

succinimidyl     maleimidyl     phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

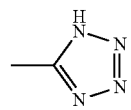

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Oxygen protecting group: the term "oxygen protecting group" refers to a moiety which masks a hydroxy group, and these are well known in the art. A large number of suitable groups are described on pages 23 to 200 of Greene, T. W. and Wuts, G. M., Protective Groups in Organic Synthesis, 3$^{rd}$ Edition, John Wiley & Sons, Inc., 1999, which is incorporated herein by reference. Classes of particular interest include silyl ethers (e.g. TMS, TBDMS), substituted methyl ethers (e.g. THP) and esters (e.g. acetate).

Carbamate nitrogen protecting group: the term "carbamate nitrogen protecting group" pertains to a moiety which masks the nitrogen in the imine bond, and these are well known in the art. These groups have the following structure:

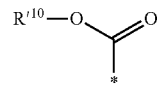

wherein R'$^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Hemi-aminal nitrogen protecting group: the term "hemi-aminal nitrogen protecting group" pertains to a group having the following structure:

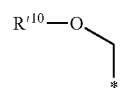

wherein R'$^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

Conjugates

The present invention provides Conjugates comprising a PBD dimer connected to a Ligand unit via a Linker unit. In one embodiment, the Linker unit includes a Stretcher unit (A), a Specificity unit (L$^1$), and a Spacer unit (L$^2$). The Linker unit is connected at one end to the Ligand unit (L) and at the other end to the PBD dimer compound (D).

In one aspect, such a Conjugate is shown below in formula IIIa:

or a pharmaceutically acceptable salt or solvate thereof, wherein:
L is the Ligand unit; and
-A$^1_a$-L$^1_s$-L$^2_y$- is a Linker unit (LU), wherein:
-A$^1$- is a Stretcher unit,
a is 1 or 2,
-L$^1$- is a Specificity unit,
s is an integer ranging from 0 to 12,
-L$^2$- is a Spacer unit,
y is 0, 1 or 2;
-D is a PBD dimer; and
p is from 1 to 20.

In another aspect, such a Conjugate is shown below in formula IIIb:

Also illustrated as:

or a pharmaceutically acceptable salt or solvate thereof, wherein:
L is the Ligand unit; and
-A$^1_a$-L$^1_s$(L$^2_y$)- is a Linker unit (LU), wherein:
-A$^1$- is a Stretcher unit linked to a Stretcher unit (L$^2$),
a is 1 or 2,
-L$^1$- is a Specificity unit linked to a Stretcher unit (L$^2$), s is an integer ranging from 0 to 12,
-$L^2$- is a Spacer unit,
y is 0, 1 or 2;
-D is a PBD dimer; and
p is from 1 to 20.

Preferences

The following preferences may apply to all aspects of the invention as described above, or may relate to a single aspect. The preferences may be combined together in any combination.

In one embodiment, the Conjugate has the formula:

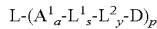

L-($A^1_a$-$L^1_s$-$L^2_y$-D)$_p$

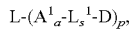

L-($A^1_a$-$L^1_s$-D)$_p$,

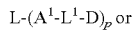

L-($A^1$-$L^1$-D)$_p$ or

L-($A^1$-D)$_p$ or a pharmaceutically acceptable salt or solvate thereof, wherein L, $A^1$, a, $L^1$, s, $L^2$, D, y and p are as described above.

In one embodiment, the Ligand unit (L) is a Cell Binding Agent (CBA) that specifically binds to a target molecule on the surface of a target cell. An exemplary formula is illustrated below:

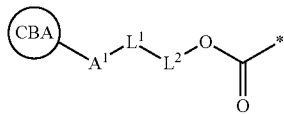

where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit, which is a covalent bond, a self-immolative group or together with —OC(=O)— forms a self-immolative group, and $L^2$ is optional. —OC(=O)— may be considered as being part of $L^1$ or $L^2$, as appropriate.

In another embodiment, the Ligand unit (L) is a Cell Binding Agent (CBA) that specifically binds to a target molecule on the surface of a target cell. An exemplary formula is illustrated below:

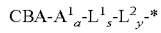

CBA-$A^1_a$-$L^1_s$-$L^2_y$-* where the asterisk indicates the point of attachment to the Drug unit (D), CBA is the Cell Binding Agent, $L^1$ is a Specificity unit, $A^1$ is a Stretcher unit connecting $L^1$ to the Cell Binding Agent, $L^2$ is a Spacer unit which is a covalent bond or a self-immolative group, and a is 1 or 2, s is 0, 1 or 2, and y is 0 or 1 or 2.

In the embodiments illustrated above, $L^1$ can be a cleavable Specificity unit, and may be referred to as a "trigger" that when cleaved activates a self-immolative group (or self-immolative groups) $L^2$, when a self-immolative group(s) is present. When the Specificity unit $L^1$ is cleaved, or the linkage (i.e., the covalent bond) between $L^1$ and $L^2$ is cleaved, the self-immolative group releases the Drug unit (D).

In another embodiment, the Ligand unit (L) is a Cell Binding Agent (CBA) that specifically binds to a target molecule on the surface of a target cell. An exemplary formula is illustrated below:

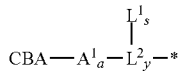

CBA—$A^1_a$—$L^2_y$—*
 |
 $L^1_s$ where the asterisk indicates the point of attachment to the Drug (D), CBA is the Cell Binding Agent, $L^1$ is a Specificity unit connected to $L^2$, $A^1$ is a Stretcher unit connecting $L^2$ to the Cell Binding Agent, $L^2$ is a self-immolative group, and a is 1 or 2, s is 1 or 2, and y is 1 or 2.

In the various embodiments discussed herein, the nature of $L^1$ and $L^2$ can vary widely. These groups are chosen on the basis of their characteristics, which may be dictated in part, by the conditions at the site to which the conjugate is delivered. Where the Specificity unit $L^1$ is cleavable, the structure and/or sequence of $L^1$ is selected such that it is cleaved by the action of enzymes present at the target site (e.g., the target cell). $L^1$ units that are cleavable by changes in pH (e.g. acid or base labile), temperature or upon irradiation (e.g. photolabile) may also be used. $L^1$ units that are cleavable under reducing or oxidising conditions may also find use in the Conjugates.

In some embodiments, $L^1$ may comprise one amino acid or a contiguous sequence of amino acids. The amino acid sequence may be the target substrate for an enzyme.

In one embodiment, $L^1$ is cleavable by the action of an enzyme. In one embodiment, the enzyme is an esterase or a peptidase. For example, $L^1$ may be cleaved by a lysosomal protease, such as a cathepsin.

In one embodiment, $L^2$ is present and together with —C(=O)O— forms a self-immolative group or self-immolative groups. In some embodiments, —C(=O)O— also is a self-immolative group.

In one embodiment, where $L^1$ is cleavable by the action of an enzyme and $L^2$ is present, the enzyme cleaves the bond between $L^1$ and $L^2$, whereby the self-immolative group(s) release the Drug unit.

$L^1$ and $L^2$, where present, may be connected by a bond selected from:

—C(=O)NH—,
—C(=O)O—,
—NHC(=O)—,
—OC(=O)—,
—OC(=O)O—,
—NHC(=O)O—,
—OC(=O)NH—,
—NHC(=O)NH, and
—O— (a glycosidic bond).

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxy group of $L^1$ that connects to $L^2$ may be derived from a hydroxy group of an amino acid side chain, for example a serine amino acid side chain.

In one embodiment, —C(=O)O— and $L^2$ together form the group:

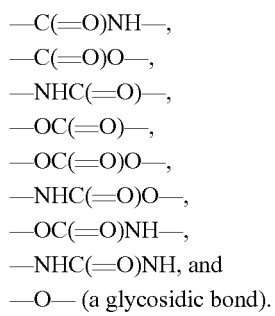

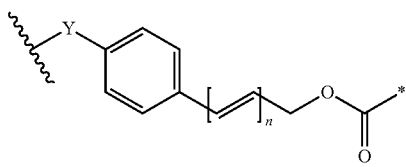

where the asterisk indicates the point of attachment to the Drug unit, the wavy line indicates the point of attachment to the $L^1$, Y is —N(H)—, —O—, —C(=O)N(H)— or —C(=O)O—, and n is 0 to 3. The phenylene ring is optionally substituted with one, two or three substituents as described herein.

In one embodiment, Y is NH.

In one embodiment, n is 0 or 1. Preferably, n is 0.

Where Y is NH and n is 0, the self-immolative group may be referred to as a p-aminobenzylcarbonyl linker (PABC).

The self-immolative group will allow for release of the Drug unit (i.e., the asymmetric PBD) when a remote site in the linker is activated, proceeding along the lines shown below (for n=0):

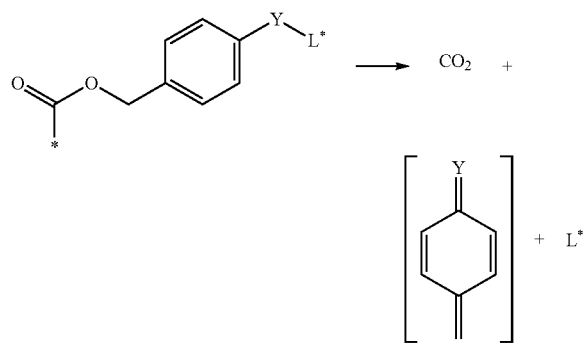

where the asterisk indicates the attachment to the Drug, L* is the activated form of the remaining portion of the linker and the released Drug unit is not shown. These groups have the advantage of separating the site of activation from the Drug.

In another embodiment, —C(=O)O— and $L^2$ together form a group selected from:

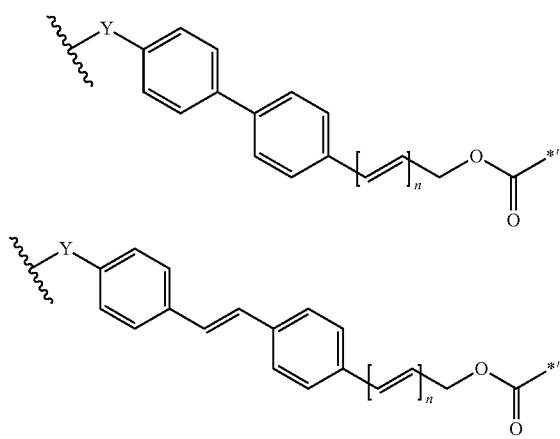

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted.

In another embodiment, —C(=O)O— and $L^2$ together form a group selected from:

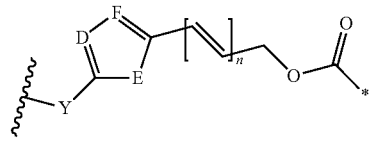

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the covalent bond between $L^1$ and $L^2$ is a cathepsin labile (e.g., cleavable) bond.

In one embodiment, $L^1$ comprises a dipeptide. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$-$X_2$— in dipeptide, —NH—$X_1$-$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$-$X_2$— in dipeptide, —NH—$X_1$-$X_2$—CO—, is selected from:
-Phe-Lys-,
-Val-Ala-,
-Val-Lys-,
-Ala-Lys-, and
-Val-Cit-.

Most preferably, the group —$X_1$-$X_2$— in dipeptide, —NH—$X_1$-$X_2$—CO—, is -Phe-Lys-, Val-Cit or -Val-Ala-.

Other dipeptide combinations of interest include:
-Gly-Gly-,
-Pro-Pro-, and
-Val-Glu-.

Other dipeptide combinations may be used, including those described by Dubowchik et al., which is incorporated herein by reference.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective groups in Organic Synthesis, Greene and Wuts.

Possible side chain protecting groups are shown below for those amino acids having reactive side chain functionality:

Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z;
Ser: Bzl, TBDMS, TBDPS;
Thr: Bz;
Trp: Boc;
Tyr: Bzl, Z, Z—Br.

In one embodiment, —$X_2$— is connected indirectly to the Drug unit. In such an embodiment, the Spacer unit $L^2$ is present.

In one embodiment, the dipeptide is used in combination with a self-immolative group(s) (the Spacer unit). The self-immolative group(s) may be connected to —$X_2$—.

Where a self-immolative group is present, —$X_2$— is connected directly to the self-immolative group. In one embodiment, —$X_2$— is connected to the group Y of the self-immolative group. Preferably the group —$X_2$—CO— is connected to Y, where Y is NH.

In one embodiment, —$X_1$— is connected directly to $A^1$. Preferably the group NH—$X_1$— (the amino terminus of $X_1$) is connected to $A^1$. $A^1$ may comprise the functionality —CO— thereby to form an amide link with —$X_1$—.

In one embodiment, $L^1$ and $L^2$ together with —OC(=O)— comprise the group —$X_1$-$X_2$-PABC-. The PABC group is connected directly to the Drug unit. In one example, the self-immolative group and the dipeptide together form the group -Phe-Lys-PABC-, which is illustrated below:

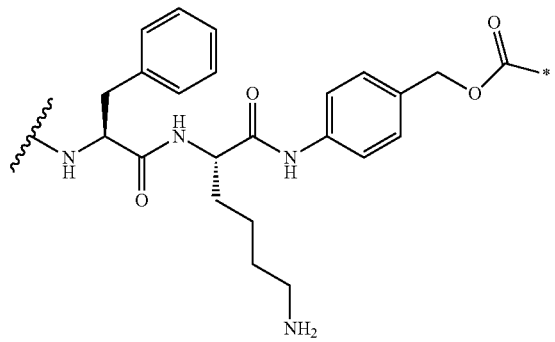 [SMILES: *N[C@@H](Cc1ccccc1)C(=O)N[C@@H](CCCCN)C(=O)Nc1ccc(COC(*)=O)cc1]

where the asterisk indicates the point of attachment to the Drug unit, and the wavy line indicates the point of attachment to the remaining portion of $L^1$ or the point of attachment to $A^1$. Preferably, the wavy line indicates the point of attachment to $A^1$.

Alternatively, the self-immolative group and the dipeptide together form the group -Val-Ala-PABC-, which is illustrated below:

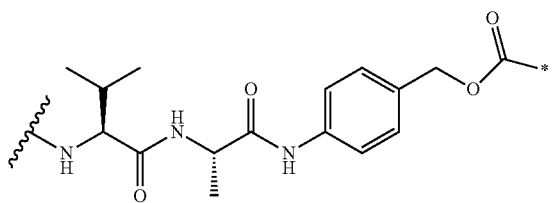 [SMILES: *N[C@H](C(=O)N[C@@H](C)C(=O)Nc1ccc(COC(*)=O)cc1)C(C)C]

where the asterisk and the wavy line are as defined above.

In another embodiment, $L^1$ and $L^2$ together with —OC(=O)— represent:

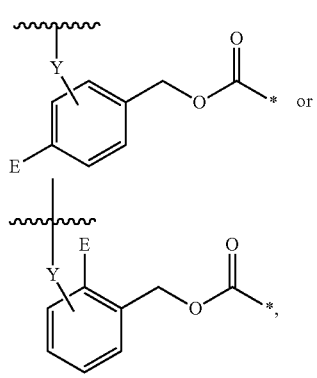

where the asterisk indicates the point of attachment to the Drug unit, the wavy line indicates the point of attachment to $A^1$, Y is a covalent bond or a functional group, and E is a group that is susceptible to cleavage thereby to activate a self-immolative group.

E is selected such that the group is susceptible to cleavage, e.g., by light or by the action of an enzyme. E may be —$NO_2$ or glucuronic acid (e.g., β-glucuronic acid). The former may be susceptible to the action of a nitroreductase, the latter to the action of a β-glucuronidase.

The group Y may be a covalent bond.

The group Y may be a functional group selected from:

—C(=O)—
—NH—
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
$SO_2$, and
—S—.

The group Y is preferably —NH—, —$CH_2$—, —O—, and —S—.

In some embodiments, $L^1$ and $L^2$ together with —OC(=O)— represent:

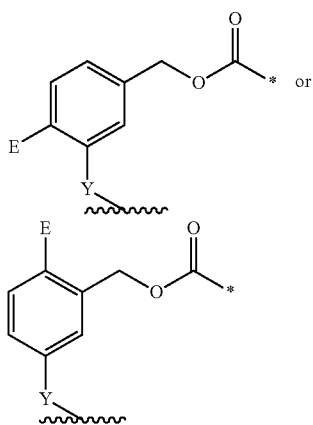 or where the asterisk indicates the point of attachment to the Drug unit, the wavy line indicates the point of attachment to A, Y is a covalent bond or a functional group and E is glucuronic acid (e.g., β-glucuronic acid). Y is preferably a functional group selected from —NH—.

In some embodiments, $L^1$ and $L^2$ together represent:

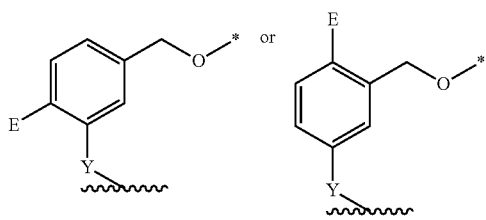

where the asterisk indicates the point of attachment to the remainder of $L^2$ or the Drug unit, the wavy line indicates the point of attachment to $A^1$, Y is a covalent bond or a functional group and E is glucuronic acid (e.g., β-glucuronic acid). Y is preferably a functional group selected from —NH—, —CH$_2$—, —O—, and —S—.

In some further embodiments, Y is a functional group as set forth above, the functional group is linked to an amino acid, and the amino acid is linked to the Stretcher unit $A^1$. In some embodiments, amino acid is β-alanine. In such an embodiment, the amino acid is equivalently considered part of the Stretcher unit.

The Specificity unit $L^1$ and the Ligand unit are indirectly connected via the Stretcher unit.

$L^1$ and $A^1$ may be connected by a bond selected from:

—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

In one embodiment, the group $A^1$ is:

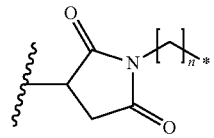

where the asterisk indicates the point of attachment to $L^1$, the wavy line indicates the point of attachment to the Ligand unit, and n is 0 to 6. In one embodiment, n is 5.

In one embodiment, the group $A^1$ is:

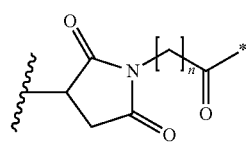

where the asterisk indicates the point of attachment to $L^1$, the wavy line indicates the point of attachment to the Ligand unit, and n is 0 to 6. In one embodiment, n is 5.

In one embodiment, the group $A^1$ is:

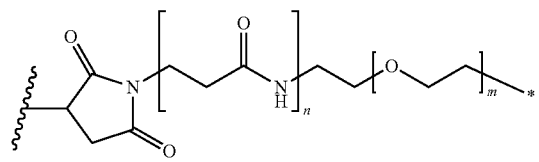

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

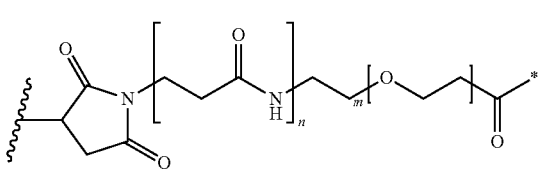

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

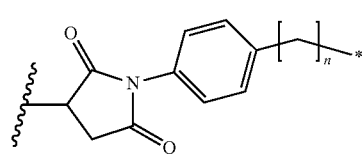

where the asterisk indicates the point of attachment to $L^1$, the wavy line indicates the point of attachment to the Ligand unit, and n is 0 to 6. In one embodiment, n is 5.

In one embodiment, the group $A^1$ is:

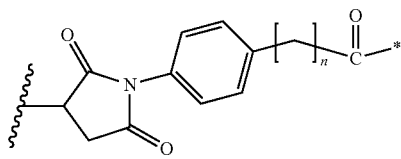

where the asterisk indicates the point of attachment to $L^1$, the wavy line indicates the point of attachment to the Ligand unit, and n is 0 to 6. In one embodiment, n is 5.

In one embodiment, the group $A^1$ is:

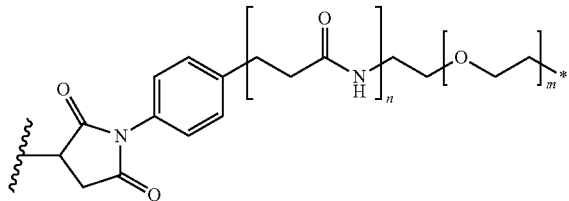

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the group $A^1$ is:

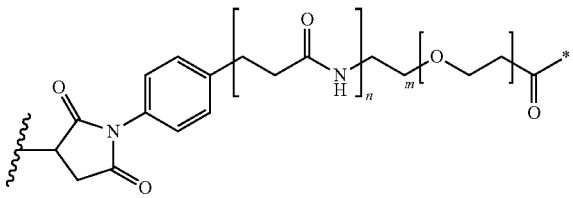

where the asterisk indicates the point of attachment to $L^1$, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the connection between the Ligand unit and $A^1$ is through a thiol residue of the Ligand unit and a maleimide group of $A^1$.

In one embodiment, the connection between the Ligand unit and $A^1$ is:

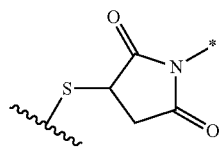 [SMILES: *SC1CC(=O)N(*)C1=O]

where the asterisk indicates the point of attachment to the remaining portion of $A^1$, $L^1$, $L^2$ or D, and the wavy line indicates the point of attachment to the remaining portion of the Ligand unit. In this embodiment, the S atom is typically derived from the Ligand unit.

In each of the embodiments above, an alternative functionality may be used in place of the malemide-derived group shown below:

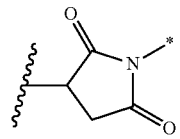 [SMILES: *C1CC(=O)N(*)C1=O]

where the wavy line indicates the point of attachment to the Ligand unit as before, and the asterisk indicates the bond to the remaining portion of the $A^1$ group, or to $L^1$, $L^2$ or D.

In one embodiment, the maleimide-derived group is replaced with the group:

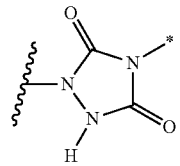 [SMILES: *n1[nH]c(=O)n(*)c1=O]

where the wavy line indicates point of attachment to the Ligand unit, and the asterisk indicates the bond to the remaining portion of the $A^1$ group, or to $L^1$, $L^2$ or D.

In one embodiment, the maleimide-derived group is replaced with a group, which optionally together with a Ligand unit (e.g., a Cell Binding Agent), is selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH$_2$C(=O)—
—C(=O)CH$_2$—,
=N—NH—, and
—NH—N=.

Of these —C(=O)CH$_2$— may be preferred especially when the carbonyl group is bound to —NH—.

In one embodiment, the maleimide-derived group is replaced with a group, which optionally together with the Ligand unit, is selected from:

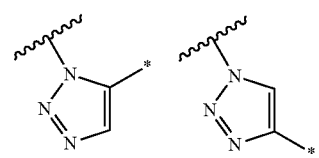 [SMILES: *c1cnnn1* ; *c1cn(*)nn1]

where the wavy line indicates either the point of attachment to the Ligand unit or the bond to the remaining portion of the $A^1$ group, and the asterisk indicates the other of the point of attachment to the Ligand unit or the bond to the remaining portion of the $A^1$ group.

Other groups suitable for connecting $L^1$ to the Cell Binding Agent are described in WO 2005/082023.

In one embodiment, the Stretcher unit $A^1$ is present, the Specificity unit $L^1$ is present and Spacer unit $L^2$ is absent. Thus, $L^1$ and the Drug unit are directly connected via a bond. Equivalently in this embodiment, $L^2$ is a bond.

$L^1$ and D may be connected by a bond selected from:
—C(=O)N<,
—C(=O)O—,
—NHC(=O)—,
—OC(=O)—,
—OC(=O)O—,
—NHC(=O)O—,
—OC(=O)N<, and
—NHC(=O)N<,
where N< or O— are part of D.

In one embodiment, $L^1$ and D are preferably connected by a bond selected from:
—C(=O)N<, and
—NHC(=O)—.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$-$X_2$— in dipeptide, —NH—$X_1$-$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$-$X_2$— in dipeptide, —NH—$X_1$-$X_2$—CO—, is selected from:
-Phe-Lys-,
-Val-Ala-,
-Val-Lys-,
-Ala-Lys-, and
-Val-Cit-.

Most preferably, the group —$X_1$-$X_2$— in dipeptide, —NH—$X_1$-$X_2$—CO—, is -Phe-Lys- or -Val-Ala-.

Other dipeptide combinations of interest include:
-Gly-Gly-,
-Pro-Pro-, and
-Val-Glu-.

Other dipeptide combinations may be used, including those described above.

In one embodiment, $L^1$-D is:

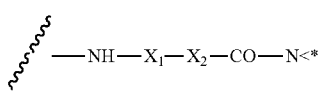

—NH—$X_1$—$X_2$—CO—N<* where —NH—$X_1$-$X_2$—CO is the dipeptide, —N< is part of the Drug unit, the asterisk indicates the points of attachment to the remainder of the Drug unit, and the wavy line indicates the point of attachment to the remaining portion of $L^1$ or the point of attachment to $A^1$. Preferably, the wavy line indicates the point of attachment to $A^1$.

In one embodiment, the dipeptide is valine-alanine and $L^1$-D is:

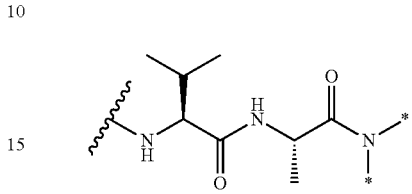

where the asterisks, —N< and the wavy line are as defined above.

In one embodiment, the dipeptide is phenylalnine-lysine and $L^1$-D is:

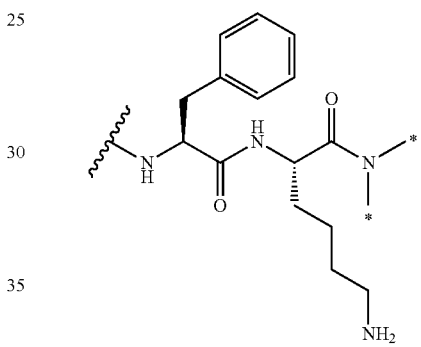

where the asterisks, —N< and the wavy line are as defined above.

In one embodiment, the dipeptide is valine-citrulline.
In one embodiment, the groups $A^1$-$L^1$ are:

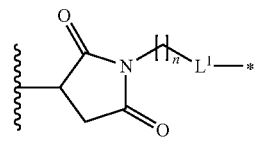

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

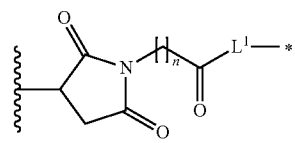

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

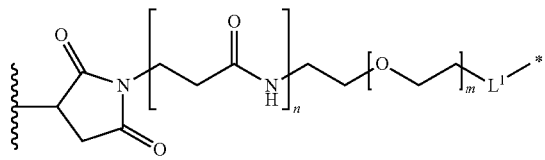

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

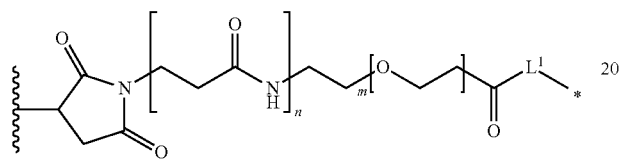

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups $A^1$-$L^1$ are:

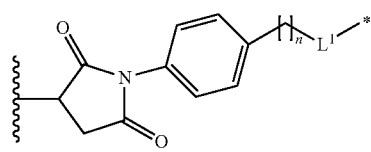

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

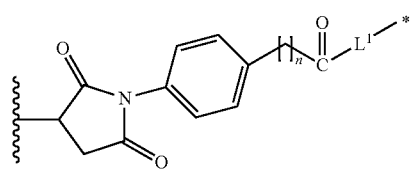

where the asterisk indicates the point of attachment to $L^2$ or D, the wavy line indicates the point of attachment to the Ligand unit, and n is 0 to 6. In one embodiment, n is 5.

In one embodiment, the groups $A^1$-$L^1$ are:

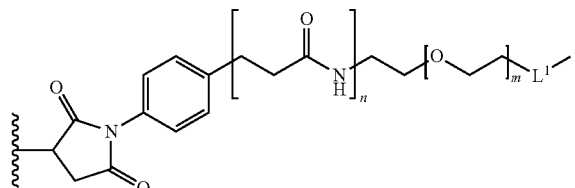

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ is:

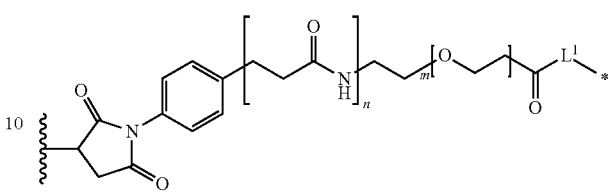

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-$A^1$-$L^1$ are:

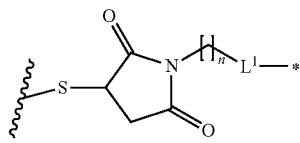

where the asterisk indicates the point of attachment to $L^2$ or D, S is a sulfur group of the Ligand unit, the wavy line indicates the point of attachment to the rest of the Ligand unit, and n is 0 to 6. In one embodiment, n is 5.

In one embodiment, the group L-$A^1$-$L^1$ are:

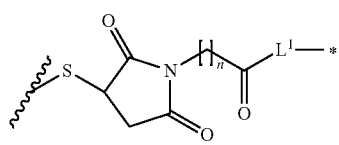

where the asterisk indicates the point of attachment to $L^2$ or D, S is a sulfur group of the Ligand unit, the wavy line indicates the point of attachment to the remainder of the Ligand unit, and n is 0 to 6. In one embodiment, n is 5.

In one embodiment, the groups L-$A^1$-$L^1$ are:

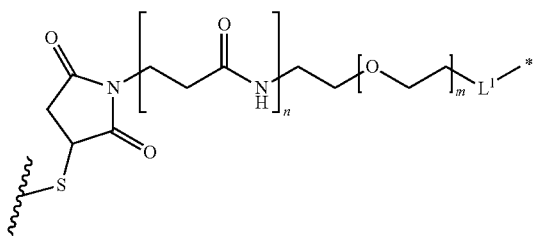

where the asterisk indicates the point of attachment to $L^2$ or D, S is a sulfur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-A¹-L¹ are:

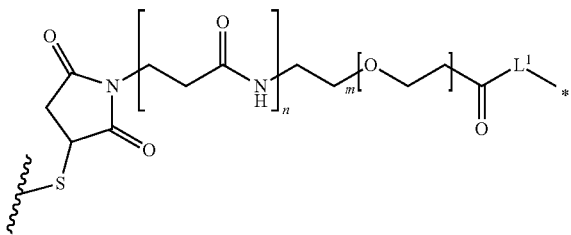

where the asterisk indicates the point of attachment to L² or D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8.

In one embodiment, the groups L-A¹-L¹ are:

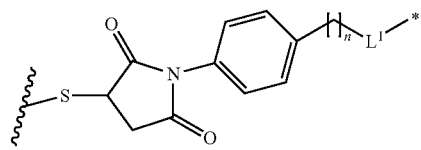

where the asterisk indicates the point of attachment to L² or D, the wavy line indicates the point of attachment to the remainder of the Ligand unit, and n is 0 to 6. In one embodiment, n is 5.

In one embodiment, the groups L-A¹-L¹ are:

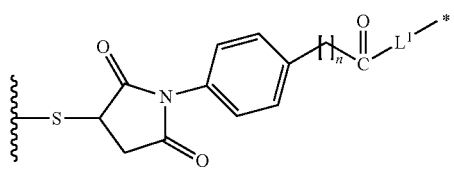

where the asterisk indicates the point of attachment to L² or D, the wavy line indicates the point of attachment to the remainder of the Ligand unit, and n is 0 to 6. In one embodiment, n is 5.

In one embodiment, the groups L-A¹-L¹ are:

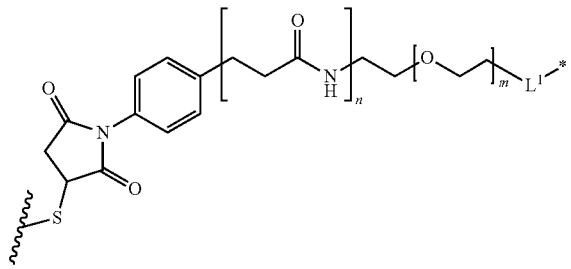

where the asterisk indicates the point of attachment to L² or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups L-A¹-L¹ are:

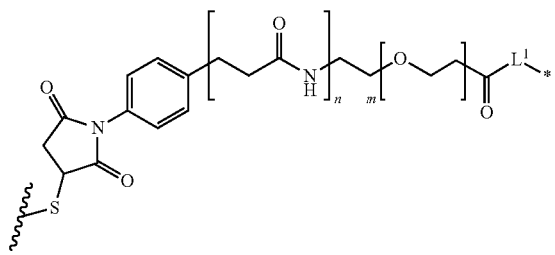

where the asterisk indicates the point of attachment to L² or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the Stretcher unit is an acetamide unit, having the formula:

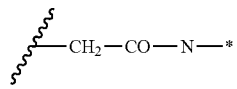

where the asterisk indicates the point of attachment to the remainder of the Stretcher unit, L¹ or D, and the wavy line indicates the point of attachment to the Ligand unit.

Linker-Drugs

In other embodiments, Linker-Drug compounds are provided for conjugation to a Ligand unit. In one embodiment, the Linker-Drug compounds are designed for connection to a Cell Binding Agent.

In one embodiment, the Drug Linker compound has the formula:

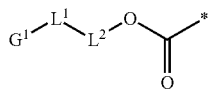

where the asterisk indicates the point of attachment to the Drug unit (D, as defined above), G¹ is a Stretcher group (A¹) to form a connection to a Ligand unit, L¹ is a Specificity unit, L² (a Spacer unit) is a covalent bond or together with —OC(=O)— forms a self-immolative group(s).

In another embodiment, the Drug Linker compound has the formula:

G¹-L¹-L²-.

where the asterisk indicates the point of attachment to the Drug unit (D), G¹ is a Stretcher unit (A¹) to form a connection to a Ligand unit, L¹ is a Specificity unit, L² (a Spacer unit) is a covalent bond or a self-immolative group(s).

L¹ and L² are as defined above. References to connection to A¹ can be construed here as referring to a connection to G¹.

In one embodiment, where L¹ comprises an amino acid, the side chain of that amino acid may be protected. Any suitable protecting group may be used. In one embodiment, the side chain protecting groups are removable with other protecting groups in the compound, where present. In other embodiments, the protecting groups may be orthogonal to other protecting groups in the molecule, where present.

Suitable protecting groups for amino acid side chains include those groups described in the Novabiochem Catalog 2006/2007. Protecting groups for use in a cathepsin labile linker are also discussed in Dubowchik et al.

In certain embodiments of the invention, the group $L^1$ includes a Lys amino acid residue. The side chain of this amino acid may be protected with a Boc or Alloc protected group. A Boc protecting group is most preferred.

The functional group $G^1$ forms a connecting group upon reaction with a Ligand unit (e.g., a cell binding agent).

In one embodiment, the functional group $G^1$ is or comprises an amino, carboxylic acid, hydroxy, thiol, or maleimide group for reaction with an appropriate group on the Ligand unit. In a preferred embodiment, $G^1$ comprises a maleimide group.

In one embodiment, the group $G^1$ is an alkyl maleimide group. This group is suitable for reaction with thiol groups, particularly cysteine thiol groups, present in the cell binding agent, for example present in an antibody.

In one embodiment, the group $G^1$ is:

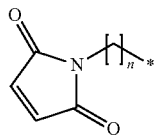

where the asterisk indicates the point of attachment to $L^1$, $L^2$ or D, and n is 0 to 6. In one embodiment, n is 5.

In one embodiment, the group $G^1$ is:

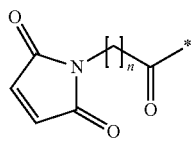

where the asterisk indicates the point of attachment to $L^1$, $L^2$ or D, and n is 0 to 6. In one embodiment, n is 5.

In one embodiment, the group $G^1$ is:

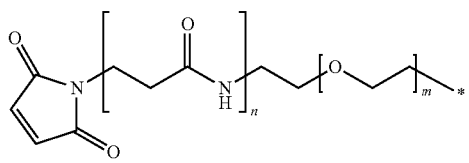

where the asterisk indicates the point of attachment to $L^1$, n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

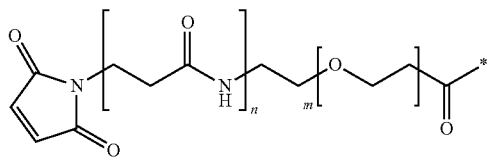

where the asterisk indicates the point of attachment to $L^1$, n is 0 or 1, and m is 0 to 30. In a preferred embodiment, n is 1 and m is 0 to 10, 1 to 8, preferably 4 to 8, and most preferably 4 or 8.

In one embodiment, the group $G^1$ is:

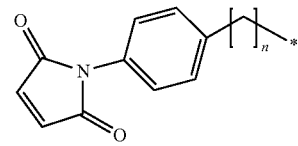

where the asterisk indicates the point of attachment to $L^1$, $L^2$ or D, and n is 0 to 6. In one embodiment, n is 5.

In one embodiment, the group $G^1$ is:

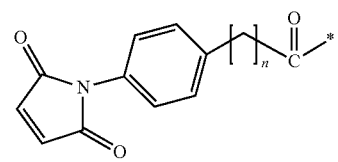

where the asterisk indicates the point of attachment to $L^1$, $L^2$ or D, and n is 0 to 6. In one embodiment, n is 5.

In one embodiment, the group $G^1$ is:

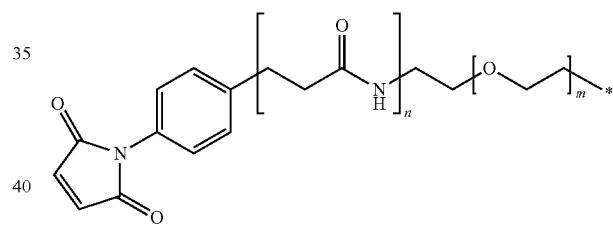

where the asterisk indicates the point of attachment to $L^1$, n is 0 or 1, and m is 0 to 30. In a preferred embodiment, n is 1 and m is 0 to 10, 1 to 2, preferably 4 to 8, and most preferably 4 or 8.

In one embodiment, the group $G^1$ is:

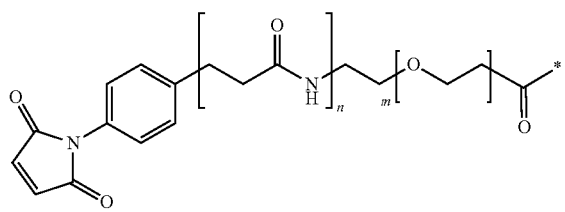

where the asterisk indicates the point of attachment to $L^1$, n is 0 or 1, and m is 0 to 30. In a preferred embodiment, n is 1 and m is 0 to 10, 1 to 8, preferably 4 to 8, and most preferably 4 or 8.

In each of the embodiments above, an alternative functionality may be used in place of the malemide group shown below:

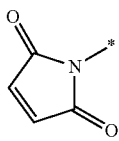

where the asterisk indicates the bond to the remaining portion of the G group.

In one embodiment, the maleimide-derived group is replaced with the group:

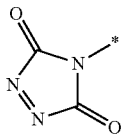

where the asterisk indicates the bond to the remaining portion of the G group.

In one embodiment, the maleimide group is replaced with a group selected from:
—C(=O)OH,
—OH,
—NH$_2$,
—SH,
—C(=O)CH$_2$X, where X is Cl, Br or I,
—CHO,
—NHNH$_2$,
—C≡CH, and
—N$_3$ (azide).

Of these, —C(=O)CH$_2$X may be preferred, especially when the carbonyl group is bound to —NH—.

In one embodiment, L$^1$ is present, and G$^1$ is —NH$_2$, —NHMe, —COOH, —OH or —SH.

In one embodiment, where L$^1$ is present, G$^1$ is —NH$_2$ or —NHMe. Either group may be the N-terminal of an L$^1$ amino acid sequence.

In one embodiment, L$^1$ is present and G$^1$ is —NH$_2$, and L is an amino acid sequence —X$_1$-X$_2$—, as defined above.

In one embodiment, L$^1$ is present and G$^1$ is COOH. This group may be the C-terminal of an L$^1$ amino acid sequence.

In one embodiment, L$^1$ is present and G$^1$ is OH.

In one embodiment, L$^1$ is present and G$^1$ is SH.

The group G$^1$ may be convertable from one functional group to another. In one embodiment, L$^1$ is present and G$^1$ is —NH$_2$. This group is convertable to another group G$^1$ comprising a maleimide group. For example, the group —NH$_2$ may be reacted with an acids or an activated acid (e.g., N-succinimide forms) of those G$^1$ groups comprising maleimide shown above.

The group G$^1$ may therefore be converted to a functional group that is more appropriate for reaction with a Ligand unit.

As noted above, in one embodiment, L$^1$ is present and G$^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, G$^1$ is —NH$_2$ in a chemically protected form. The group may be protected with a carbamate protecting group. The carbamate protecting group may be selected from the group consisting of: Alloc, Fmoc, Boc, Troc, Teoc, Cbz and PNZ.

Preferably, where G$^1$ is —NH$_2$, it is protected with an Alloc or Fmoc group.

In one embodiment, where G$^1$ is —NH$_2$, it is protected with an Fmoc group.

In one embodiment, the protecting group is the same as the carbamate protecting group of the capping group.

In one embodiment, the protecting group is not the same as the carbamate protecting group of the capping group. In this embodiment, it is preferred that the protecting group is removable under conditions that do not remove the carbamate protecting group of the capping group.

The chemical protecting group may be removed to provide a functional group to form a connection to a Ligand unit. Optionally, this functional group may then be converted to another functional group as described above.

In one embodiment, the active group is an amine. This amine is preferably the N-terminal amine of a peptide, and may be the N-terminal amine of the preferred dipeptides of the invention.

The active group may be reacted to yield the functional group that is intended to form a connection to a Ligand unit.

In other embodiments, the Linker unit is a precursor to the Linker unit having an active group. In this embodiment, the Linker unit comprises the active group, which is protected by way of a protecting group. The protecting group may be removed to provide the Linker unit having an active group.

Where the active group is an amine, the protecting group may be an amine protecting group, such as those described in Green and Wuts.

The protecting group is preferably orthogonal to other protecting groups, where present, in the Linker unit.

In one embodiment, the protecting group is orthogonal to the capping group. Thus, the active group protecting group is removable whilst retaining the capping group. In other embodiments, the protecting group and the capping group is removable under the same conditions as those used to remove the capping group.

In one embodiment, the Linker unit is:

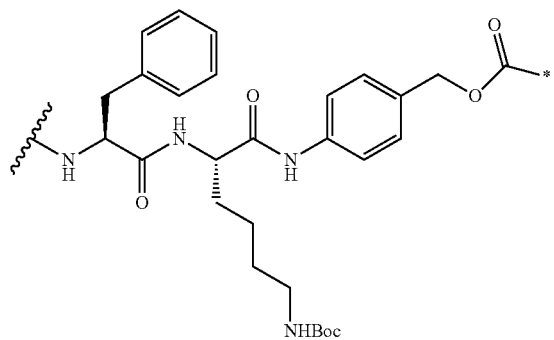 [SMILES: *N[C@@H](Cc1ccccc1)C(=O)N[C@@H](CCCCNC(=O)OC(C)(C)C)C(=O)Nc1ccc(COC(*)=O)cc1]

where the asterisk indicates the point of attachment to the Drug unit, and the wavy line indicates the point of attachment to the remaining portion of the Linker unit, as applicable or the point of attachment to G$^1$. Preferably, the wavy line indicates the point of attachment to G$^1$.

In one embodiment, the Linker unit is:

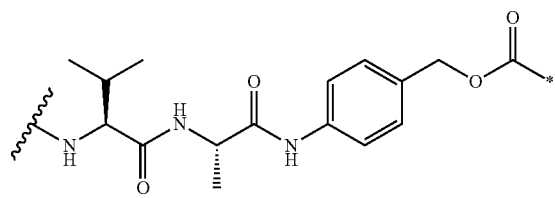

where the asterisk and the wavy line are as defined above.

Other functional groups suitable for use in forming a connection between $L^1$ and the Cell Binding Agent are described in WO 2005/082023.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target. The ligand Unit is also referred to herein as a "binding agent" or "targeting agent".

The terms "specifically binds" and "specific binding" refer to the binding of an antibody or other protein, polypeptide or peptide to a predetermined molecule (e.g., an antigen). Typically, the antibody or other molecule binds with an affinity of at least about $1 \times 10^7$ $M^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')$_2$ and Fv fragments.

The antibody may be a diabody, a domain antibody (DAB) or a single chain antibody.

In one embodiment, the antibody is a monoclonal antibody.

Antibodies for use in the present invention include those antibodies described in WO 2005/082023 which is incorporated herein. Particularly preferred are those antibodies for tumour-associated antigens. Examples of those antigens known in the art include, but are not limited to, those tumour-associated antigens set out in WO 2005/082023. See, for instance, pages 41-55.

In some embodiments, the conjugates are designed to target tumour cells via their cell surface antigens. The antigens may be cell surface antigens which are either over-expressed or expressed at abnormal times or cell types. Preferably, the target antigen is expressed only on proliferative cells (preferably tumour cells); however this is rarely observed in practice. As a result, target antigens are usually selected on the basis of differential expression between proliferative and healthy tissue.

Antibodies have been raised to target specific tumour related antigens including:

Cripto, CD19, CD20, CD22, CD30, CD33, Glycoprotein NMB, CanAg, Her2 (ErbB2/Neu), CD56 (NCAM), CD70, CD79, CD138, PSCA, PSMA (prostate specific membrane antigen), BCMA, E-selectin, EphB2, Melanotransferin, Muc16 and TMEFF2.

The Ligand unit is connected to the Linker unit. In one embodiment, the Ligand unit is connected to A, where present, of the Linker unit.

In one embodiment, the connection between the Ligand unit and the Linker unit is through a thioether bond.

In one embodiment, the connection between the Ligand unit and the Linker unit is through a disulfide bond.

In one embodiment, the connection between the Ligand unit and the Linker unit is through an amide bond.

In one embodiment, the connection between the Ligand unit and the Linker unit is through an ester bond.

In one embodiment, the connection between the Ligand unit and the Linker is formed between a thiol group of a cysteine residue of the Ligand unit and a maleimide group of the Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008070593, which are incorporated herein.

Methods of Treatment

The compounds of the present invention may be used in a method of therapy. Also provided is a method of treatment, comprising administering to a subject in need of treatment a therapeutically-effective amount of a compound of formula I. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Compounds and Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolyts, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Carbinolamines

The invention includes compounds where a solvent adds across the imine bond of the PBD moiety, which is illustrated below where the solvent is water or an alcohol ($R^A$OH, where $R^A$ is $C_{1-4}$ alkyl):

These forms can be called the carbinolamine and carbinolamine ether forms of the PBD. The balance of these equilibria depend on the conditions in which the compounds are found, as well as the nature of the moiety itself.

These particular compounds may be isolated in solid form, for example, by lyophilisation.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

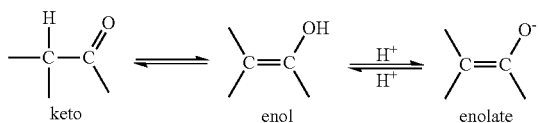

keto          enol          enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or

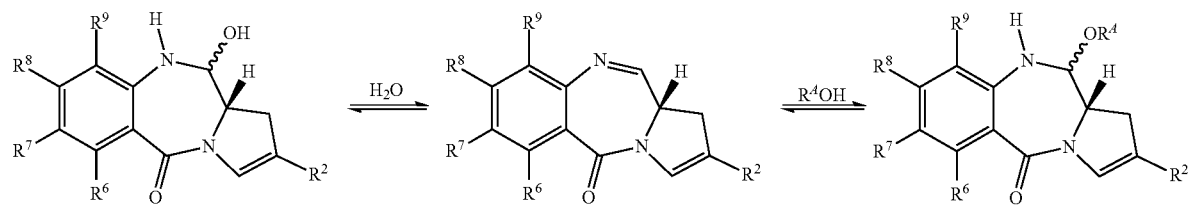

partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

General Synthetic Routes

The synthesis of PBD compounds is extensively discussed in the following references, which discussions are incorporated herein by reference:
a) WO 00/12508 (pages 14 to 30);
b) WO 2005/023814 (pages 3 to 10);
c) WO 2004/043963 (pages 28 to 29); and
d) WO 2005/085251 (pages 30 to 39).

Synthesis Route

The compounds of the present invention, where $R^{10}$ and $R^{11}$ form a nitrogen-carbon double bond between the nitrogen and carbon atoms to which they are bound, can be synthesised from a compound of Formula 2:

Formula 2

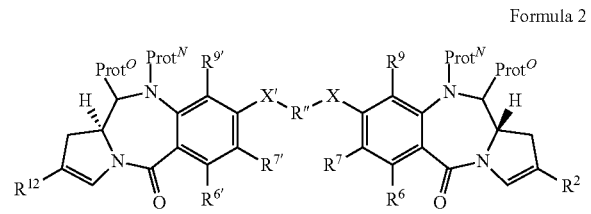

where $R^2$, $R^6$, $R^7$, $R^9$, $R^{6'}$, $R^{7'}$, $R^{9'}$, $R^{12}$, X, X' and R" are as defined for compounds of formula I, $Prot^N$ is a nitrogen protecting group for synthesis and $Prot^O$ is a protected oxygen group for synthesis or an oxo group, by deprotecting the imine bond by standard methods.

The compound produced may be in its carbinolamine or carbinolamine ether form depending on the solvents used. For example if $Prot^N$ is Troc and $Prot^O$ is an oxygen protecting group for synthesis, then the deprotection is carried out using a Cd/Pb couple to yield the compound of formula (I). If $Prot^N$ is SEM, or an analogous group, and $Prot^O$ is an an oxo group, then the oxo group can be removed by reduction, which leads to a protected carbinolamine intermediate, which can then be treated to remove the SEM protecting group, followed by the elimination of water. The reduction of the compound of Formula 2 can be accomplished by, for example, lithium tetraborohydride, whilst a suitable means for removing the SEM protecting group is treatment with silica gel.

Compounds of formula 2 can be synthesised from a compound of formula 3a:

Formula 3a

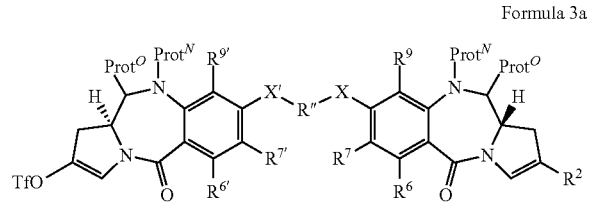

where $R^2$, $R^6$, $R^7$, $R^9$, $R^{6'}$, $R^{7'}$, $R^{9'}$, X, X' and R" are as defined for compounds of formula 2, by coupling an organometallic derivative comprising $R^{12}$, such as an organoboron derivative. The organoboron derivative may be a boronate or boronic acid.

Compounds of formula 2 can be synthesised from a compound of formula 3b:

Formula 3b

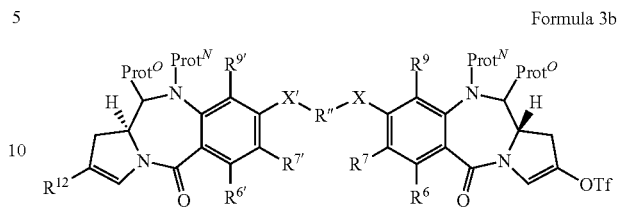

where $R^{12}$, $R^6$, $R^7$, $R^9$, $R^{6'}$, $R^{7'}$, $R^{9'}$, X, X' and R" are as defined for compounds of formula 2, by coupling an organometallic derivative comprising $R^2$, or a precursor thereof, such as an organoboron derivative. The organoboron derivative may be a boronate or boronic acid.

Compounds of formulae 3a and 3b can be synthesised from a compound of formula 4:

Formula 4

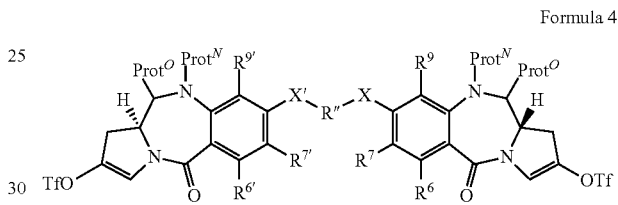

where $R^2$, $R^6$, $R^7$, $R^9$, $R^{6'}$, $R^{7'}$, $R^{9'}$, X, X' and R" are as defined for compounds of formula 2, by coupling about a single equivalent (e.g. 0.9 or 1 to 1.1 or 1.2) of an organometallic derivative, such as an organoboron derivative, comprising $R^2$ or $R^{12}$.

The couplings described above are usually carried out in the presence of a palladium catalyst, for example $Pd(PPh_3)_4$, $Pd(OCOCH_3)_2$, $PdCl_2$, $Pd_2(dba)_3$. The coupling may be carried out under standard conditions, or may also be carried out under microwave conditions.

The two coupling steps are usually carried out sequentially. They may be carried out with or without purification between the two steps. If no purification is carried out, then the two steps may be carried out in the same reaction vessel. Purification is usually required after the second coupling step. Purification of the compound from the undesired by-products may be carried out by column chromatography or ion-exchange separation.

The synthesis of compounds of formula 4 where $Prot^O$ is an oxo group and $Prot^N$ is SEM are described in detail in WO 00/12508, which is incorporated herein by reference. In particular, reference is made to scheme 7 on page 24, where the above compound is designated as intermediate P. This method of synthesis is also described in WO 2004/043963.

The synthesis of compounds of formula 4 where $Prot^O$ is a protected oxygen group for synthesis are described in WO 2005/085251, which synthesis is herein incorporated by reference.

Compounds of formula I where $R^{10}$ and $R^{10'}$ are H and R" and $R^{11'}$ are $SO_zM$, can be synthesised from compounds of formula I where $R^{10}$ and $R^{11}$ form a nitrogen-carbon double bond between the nitrogen and carbon atoms to which they are bound, by the addition of the appropriate bisulphite salt or sulphinate salt, followed by an appropriate purification step.

Further methods are described in GB 2 053 894, which is herein incorporated by reference.

Nitrogen Protecting Groups for Synthesis

Nitrogen protecting groups for synthesis are well known in the art. In the present invention, the protecting groups of particular interest are carbamate nitrogen protecting groups and hemi-aminal nitrogen protecting groups.

Carbamate nitrogen protecting groups have the following structure:

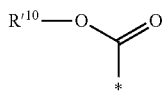

wherein $R'^{10}$ is R as defined above. A large number of suitable groups are described on pages 503 to 549 of Greene, T. W. and Wuts, G. M., Protective Groups in Organic Synthesis, $3^{rd}$ Edition, John Wiley & Sons, Inc., 1999, which is incorporated herein by reference.

Particularly preferred protecting groups include Troc, Teoc, Fmoc, BOC, Doc, Hoc, TcBOC, 1-Adoc and 2-Adoc.

Other possible groups are nitrobenzyloxycarbonyl (e.g. 4-nitrobenzyloxycarbonyl) and 2-(phenylsulphonyl)ethoxycarbonyl.

Those protecting groups which can be removed with palladium catalysis are not preferred, e.g. Alloc.

Hemi-aminal nitrogen protecting groups have the following structure:

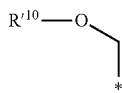

wherein $R'^{10}$ is R as defined above. A large number of suitable groups are described on pages 633 to 647 as amide protecting groups of Greene, T. W. and Wuts, G. M., Protective Groups in Organic Synthesis, $3^{rd}$ Edition, John Wiley & Sons, Inc., 1999, which is incorporated herein by reference. The groups disclosed herein can be applied to compounds of the present invention. Such groups include, but are not limited to, SEM, MOM, MTM, MEM, BOM, nitro or methoxy substituted BOM, $Cl_3CCH_2OCH_2$—.

Protected Oxygen Group for Synthesis

Protected oxygen group for synthesis are well known in the art. A large number of suitable oxygen protecting groups are described on pages 23 to 200 of Greene, T. W. and Wuts, G. M., Protective Groups in Organic Synthesis, $3^{rd}$ Edition, John Wiley & Sons, Inc., 1999, which is incorporated herein by reference.

Classes of particular interest include silyl ethers, methyl ethers, alkyl ethers, benzyl ethers, esters, acetates, benzoates, carbonates, and sulfonates.

Preferred oxygen protecting groups include acetates, TBS and THP.

Synthesis of Drug Conjugates

Conjugates can be prepared as previously described. Linkers having a maleimidyl group (A), a peptide group ($L^1$) and self-immolative group ($L^2$) can be prepared as described in U.S. Pat. No. 6,214,345, which is incorporated herein by reference. Linkers having a maleimidyl group (A) and a peptide group ($L^1$) can be prepared as described in WO 2009/0117531, which is incorporated herein by reference. Other linkers can be prepared according to the references cited herein or as known to the skilled artisan.

Linker-Drug compounds can be prepared according to methods known in the art. Linkage of amine-based X substituents (of the PDB dimer Drug unit) to active groups of the Linker units can be performed according to methods generally described in U.S. Pat. Nos. 6,214,345 and 7,498,298; and WO 2009-0117531, or as otherwise known to the skilled artisan.

Antibodies can be conjugated to Linker-Drug compounds as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 µm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Antibodies with introduced cysteine residues can be conjugated to Linker-Drug compounds as described in International Patent Publication WO2008/070593, which is incorporated herein or as follows. Antibodies containing an introduced cysteine residue in the heavy chain are fully reduced by adding 10 equivalents of TCEP and 1 mM EDTA and adjusting the pH to 7.4 with 1M Tris buffer (pH 9.0). Following a 1 hour incubation at 37° C., the reaction is cooled to 22° C. and 30 equivalents of dehydroascorbic acid is added to selectively reoxidize the native disulfides, while leaving the introduced cysteine in the reduced state. The pH is adjusted to 6.5 with 1M Tris buffer (pH 3.7) and the reaction is allowed to proceed for 1 hour at 22° C. The pH of the solution is then raised again to 7.4 by addition of 1 M Tris buffer (pH 9.0). 3.5 equivalents of the PBD drug linker in DMSO is placed in a suitable container for dilution with propylene glycol prior to addition to the reaction. To maintain solubility of the PBD drug linker, the antibody itself is first diluted with propylene glycol to a final concentration of 33% (e.g., if the antibody solution was in a 60 mL reaction volume, 30 mL of propylene glycol was added). This same volume of propylene glycol (30 mL in this example) is added to the PBD drug linker as a diluent. After mixing, the solution of PBD drug linker in propylene glycol is added to the antibody solution to effect the conjugation; the final concentration of propylene glycol is 50%. The reaction is allowed to proceed for 30 minutes and then quenched by addition of 5 equivalents of N-acetyl cysteine. The ADC is purified by ultrafiltration through a 30 kD membrane. (Note that the concentration of propylene glycol used in the reaction can be reduced for any particular PBD, as its sole purpose is to maintain solubility of the drug linker in the aqueous media.)

For halo-acetamide-based Linker-Drug compounds, conjugation can be performed generally as follows. To a solution of reduced and reoxidized antibodies (having introduced cysteines in the heavy chain) in 10 mM Tris (pH 7.4), 50 mM NaCl, and 2 mM DTPA is added 0.5 volumes of propylene glycol. A 10 mM solution of acetamide-based Linker-Drug compound in dimethylacetamide is prepared immediately prior to conjugation. An equivalent amount of propylene glycol as added to the antibody solution is added to a 6-fold molar excess of the Linker-Drug compound. The dilute Linker-Drug solution is added to the antibody solution and the pH is adjusted to 8-8.5 using 1 M Tris (pH 9). The conjugation reaction is allowed to proceed for 45 minutes at 37° C. The conjugation is verified by reducing and denaturing reversed phase PLRP-S chromatography. Excess Linker-Drug compound is removed with Quadrasil MP resin and the buffer is exchanged into 10 mM Tris (pH 7.4), 50 mM NaCl, and 5% propylene glycol using a PD-10 desalting column.

Illustrative Synthesis Schemes for Drug Linkers

The following schemes are illustrative of routes for synthesising drug linkers—the PBD dimer is shown with specific substituents, and dimer links, but these may be varied within the scope of the present invention.

The glucuronide linker intermediate S1 (reference: Jeffrey et al., *Bioconjugate Chemistry,* 2006, 17, 831-840) can be treated with diphosgene in dichlroromethane at −78° C. to afford the glucuronide chloroformate, which is then reacted with the PBD dimer S2 dissolved in $CH_2Cl_2$ by dropwise addition. Warming the reaction to 0° C. over 2 hours followed by extraction will yield the compound S3. Treating a solution of S3 in an equal solvent mixture of MeOH, tetrahydrofuran, and water (cooled to 0° C.) with lithium hydroxide monohydrate for 4 hours, followed by reaction with glacial acetic acid will yield the compound S4. Adding maleimidocaproyl NHS ester to a solution of S4 in DMF, followed by diisopropylethylamine and stirring at room temperature under nitrogen for 2 hours will yield the desired drug linker S5.

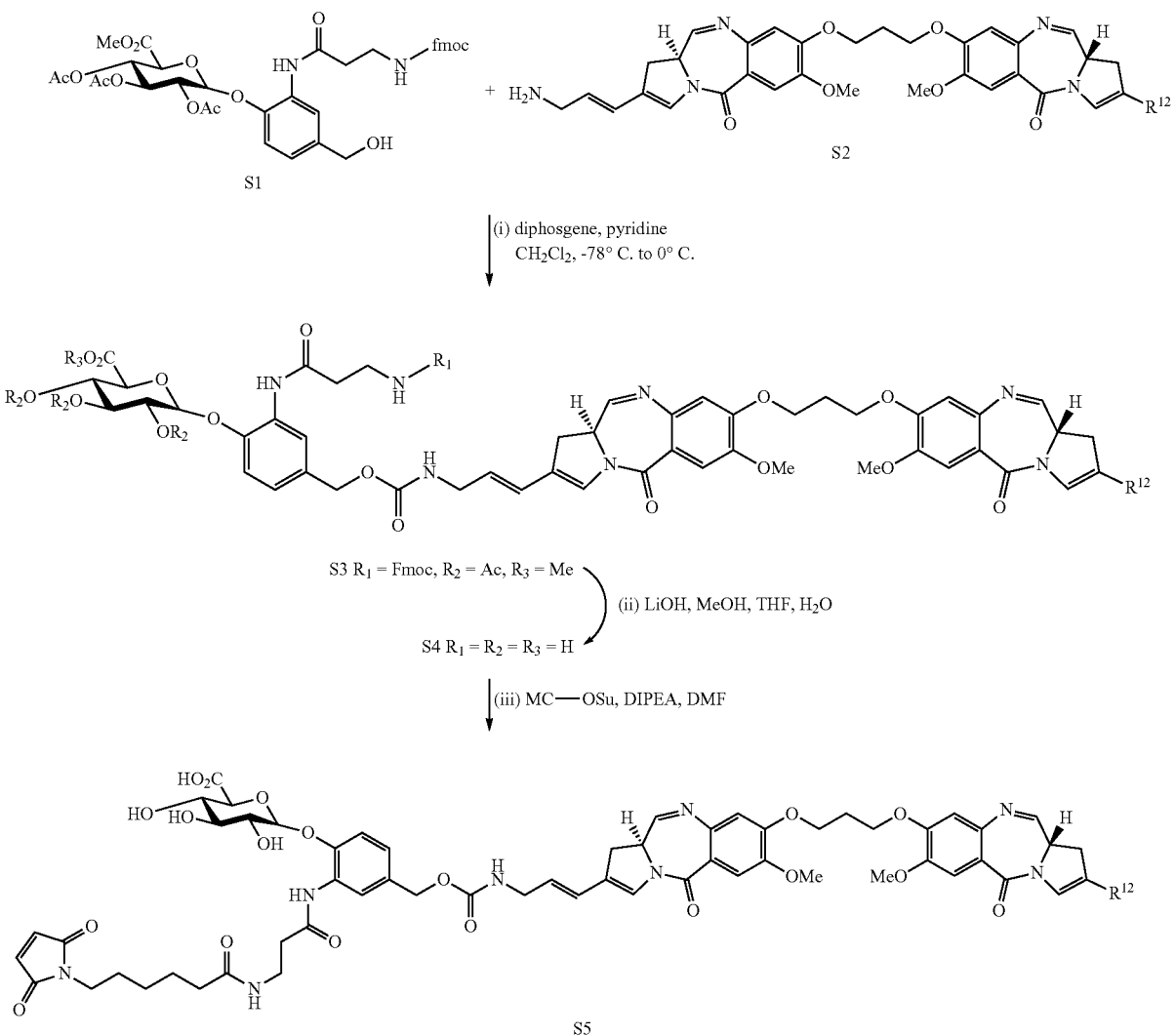

Scheme A

Scheme B
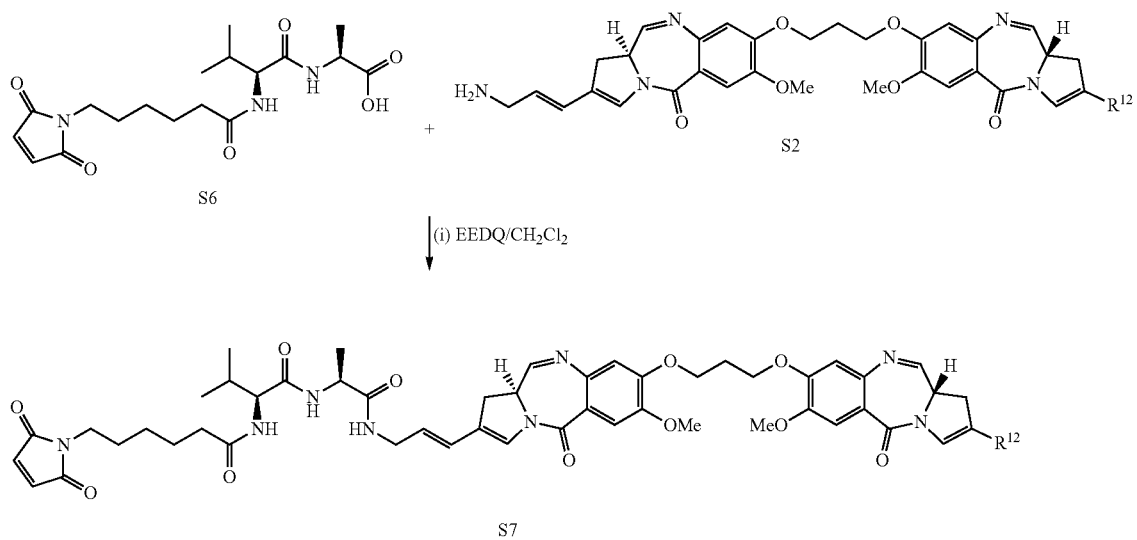
The maleimide linker S6, which can be synthesised by reacting maleimidocaproyl N-hydroxysuccinimide and H-Val-Ala-OH, can be linked to the exemplary compounds, S2, in the presence of EEDQ in anhydrous dichloromethane.
Scheme C
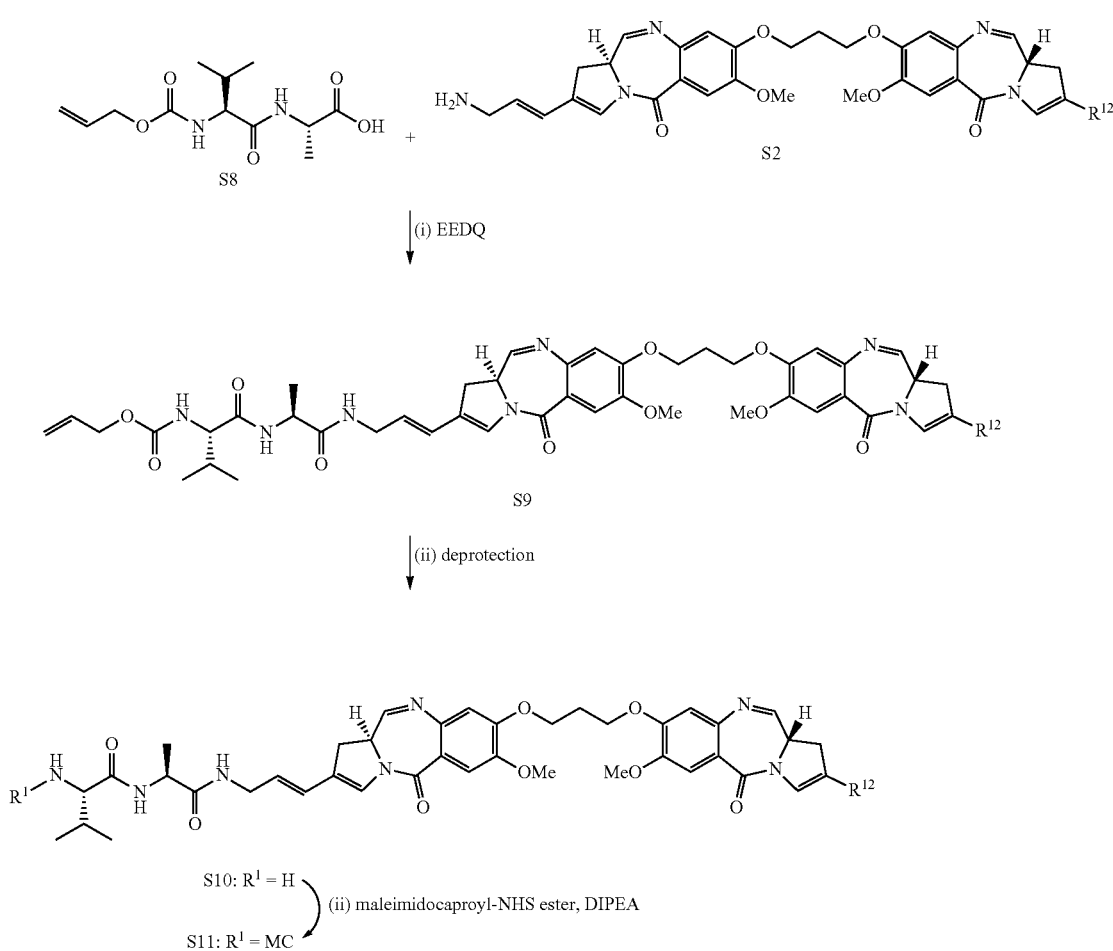

The linker S8 can be linked to the exemplary compounds, S2, in the presence of EEDQ in 5% methanol/dichloromethane. The deprotection of S9 can be carried out with the use of $Ph_3P$, pyrollidine and tetrakis palladium in anhydrous dichloromethane. S10 can be converted to the desired products by adding maleimidocaproyl-NHS ester, in the presence of DIPEA in DMF.

Further Preferences

The following preferences may apply to all aspects of the invention as described above, or may relate to a single aspect. The preferences may be combined together in any combination.

In some embodiments, $R^{6'}$, $R^{7'}$, $R^{9'}$, $R^{10'}$, $R^{11'}$ and Y' are preferably the same as $R^6$, $R^7$, $R^9$, $R^{10}$, $R^{11}$ and Y respectively.

Dimer Link

Y and Y' are preferably O.

R" is preferably a $C_{3-7}$ alkylene group with no substituents. More preferably R" is a $C_3$, $C_5$ or $C_7$ alkylene. Most preferably, R" is a $C_3$ or $C_5$ alkylene.

$R^6$ to $R^9$ $R^9$ is preferably H.

$R^6$ is preferably selected from H, OH, OR, SH, $NH_2$, nitro and halo, and is more preferably H or halo, and most preferably is H.

$R^7$ is preferably selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. $-NMe_2$); $-(OC_2H_4)_qOMe$, where q is from 0 to 2; nitrogen-containing $C_6$ heterocyclyls, including morpholino, piperidinyl and N-methyl-piperazinyl.

These preferences apply to $R^{9'}$, $R^{6'}$ and $R^{7'}$ respectively.

$R^2$ $R^{C1}$, $R^{C2}$ and $R^{C3}$ are independently selected from H and unsubstituted $C_{1-2}$ alkyl. In some preferred embodiments, $R^{C1}$, $R^{C2}$ and $R^{C3}$ are all H. In other embodiments, $R^{C1}$, $R^{C2}$ and $R^{C3}$ are all methyl. In certain embodiments, $R^{C1}$, $R^{C2}$ and $R^{C3}$ are independently selected from H and methyl.

X is a group selected from the list comprising: OH, SH, $CO_2H$, COH, N=C=O, $NHNH_2$, $CONHNH_2$,

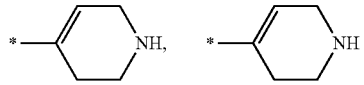

and $NHR^N$, wherein $R^N$ is selected from the group comprising H and $C_{1-4}$ alkyl. X may preferably be: OH, SH, $CO_2H$, —N=C=O or $NHR^N$, and may more preferably be: OH, SH, $CO_2H$, —N=C=O or $NH_2$. Particularly preferred groups include: OH, SH and $NH_2$, with $NH_2$ being the most preferred group.

$R^{12}$ $R^{12}$ is selected from:

(a) $C_{6-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

(d)

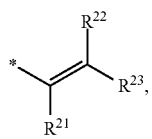

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(e)

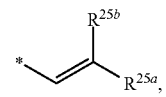

wherein one of $R^{25a}$ and $R^{25b}$ is H and the other is selected from: phenyl, which phenyl is optionally substituted by a group selected from halo methyl, methoxy; pyridyl; and thiophenyl; and (f)

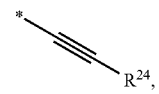

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

When $R^{12}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4-yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4-yl, isoquinolin-5-yl, isoquinolin-6-yl, isoquinolin-7-yl and isoquinolin-8-yl. Of these isoquinolin-3-yl and isoquinolin-6-yl may be preferred.

When $R^{12}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents, when $R^{12}$ is a $C_{5-10}$ Aryl Group

If a substituent on $R^{12}$ when $R^{12}$ is a $C_{8-10}$ aryl group is halo, it is preferably F or Cl, more preferably F.

If a substituent on $R^{12}$ when $R^{12}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^{12}$ when $R^{12}$ is a $C_{5-10}$ aryl group is $C_{1-7}$ alkyl, it may preferably be a $C_{1-4}$ alkyl group (e.g. methyl, ethyl, propryl, butyl).

If a substituent on $R^{12}$ when $R^{12}$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{12}$ when $R^{12}$ is a $C_{5-10}$ aryl group is bis-oxy-$C_{1-3}$ alkylene, this is preferably bis-oxy-methylene or bis-oxy-ethylene.

Particularly preferred substituents when $R^{12}$ is a $C_{5-10}$ aryl group include methoxy, ethoxy, fluoro, chloro, cyano, bis-oxy-methylene, methyl-piperazinyl, morpholino and methyl-thiophenyl. Another particularly preferred substituent for $R^{12}$ is dimethylaminopropyloxy.

Particularly preferred substituted $R^{12}$ groups when $R^{12}$ is a $C_{5-10}$ aryl group include, but are not limited to, 4-methoxyphenyl, 3-methoxyphenyl, 4-methylphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_{3-6}$ saturated cycloalkyl, it may be cyclopropyl, cyclobutyl, cyclopentyl or cyclohexyl. In some embodiments, it may be cyclopropyl.

When $R^{12}$ is

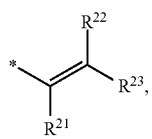

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that are not H are methyl.

In some embodiments, $R^{21}$ is H.
In some embodiments, $R^{22}$ is H.
In some embodiments, $R^{23}$ is H.
In some embodiments, $R^{21}$ and $R^{22}$ are H.
In some embodiments, $R^{21}$ and $R^{23}$ are H.
In some embodiments, $R^{22}$ and $R^{23}$ are H.

An $R^{12}$ group of particular interest is:

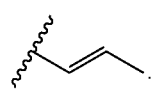 [SMILES: */C=C/C]

When $R^{12}$ is

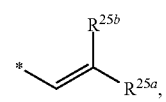

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

M and z

It is preferred that M and M' are monovalent pharmaceutically acceptable cations, and are more preferably $Na^+$.

z is preferably 3.

Particularly preferred compounds of the present invention are of formula Ia:

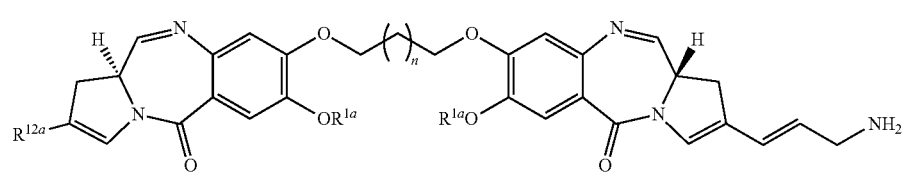

Ia where
n is 1 or 3;
$R^{1a}$ is methyl or phenyl;
$R^{12a}$ is selected from:

(a)

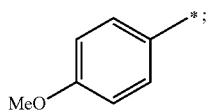

(b)

(c)

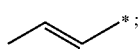

(d)

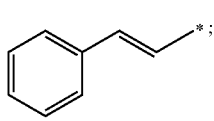

(e)

(f)

Further groups for $R12^a$ may be:

(g)

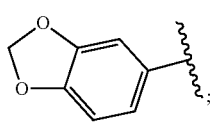 [SMILES: *c1ccc2c(c1)OCO2]

and
(h)

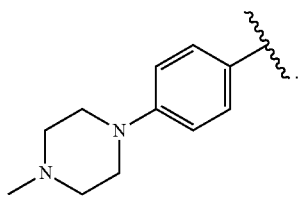 [SMILES: *c1ccc(N2CCN(C)CC2)cc1]

3rd Aspect

The preferences expressed above for the first aspect may apply to the compounds of this aspect, where appropriate.

When $R^{10}$ is carbamate nitrogen protecting group, it may preferably be Teoc, Fmoc and Troc, and may more preferably be Troc.

When $R^{11}$ is O-Prot$^O$, wherein Prot$^O$ is an oxygen protecting group, Prot$^O$ may preferably be TBS or THP, and may more preferably be TBS.

When $R^{10}$ is a hemi-aminal nitrogen protecting group, it may preferably be MOM, BOM or SEM, and may more preferably be SEM.

The preferences for compounds of formula I apply as appropriate to D in the sixth aspect of the invention. For example, in the sixth aspect, the PBD dimer is any of the compounds of formula I, or a pharmaceutically acceptable salt or solvate thereof, described herein expect that,

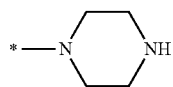

is replaced with

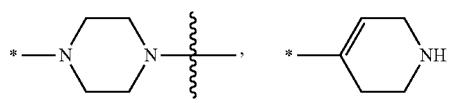

is replaced with

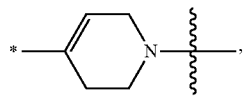

and *—NHR$^N$ is replaced with

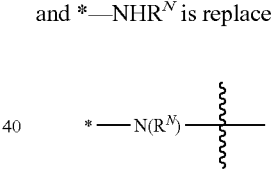

where the wavy line indicates the point of attachment to the Linker Unit.

Accordingly, the Conjugates of the present invention include those having the following formula (IV)

$$L\text{-}(LU\text{-}D)_p \qquad (IV)$$

or a pharmaceutically acceptable salt or solvate thereof, wherein L is a Ligand unit (i.e., a targeting agent), LU is a Linker unit and the PBD dimer D D is any of the compounds of formula I, or a pharmaceutically acceptable salt or solvate thereof, described herein expect that,

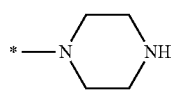

is replaced with

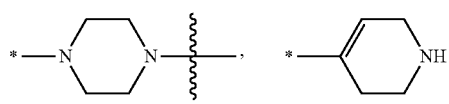

is replaced with

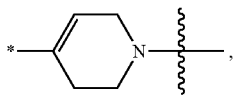

and *—NHR$^N$ is replaced with

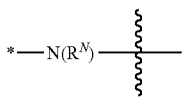

where the wavy line indicates the point of attachment to the Linker Unit.

(a) Conjugates of the present invention include, for example, those of the formula:

where the asterisk indicates the point of attachment to the PBD dimer (D), CBA is the Cell Binding Agent, L$^1$ is a Specificity unit that is cleavable by the action of an enzyme, and A$^1$ is a Stretcher unit connecting L$^1$ to the Cell Binding Agent.

(b) Conjugates of the present invention include, for example, those of the formula:

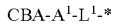

where the asterisk indicates the point of attachment to the PBD dimer (D), CBA is the Cell Binding Agent, A$^1$ is a Stretcher unit connecting L$^1$ to the Cell Binding Agent and L$^1$ is a Specificity unit that is cleavable by the action of cathepsin, L$^1$ is a dipeptide, L$^1$ is a dipeptide that is cleavable by the action of cathepsin or L$^1$ is a dipeptide selected from -Phe-Lys-, -Val-Ala-, -Val-Lys-, -Ala-Lys-, and -Val-Cit-.

Preferred conjugates of the present invention include any of those described in (a) and (b) wherein A$^1$ is

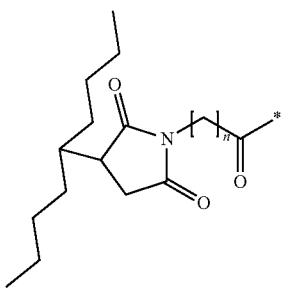

where the asterisk indicates the point of attachment to L$^1$, the wavy line indicates the point of attachment to CBA, and n is 0 to 6 (preferably n is 5).

EXAMPLES

General Experimental Methods for Example 1

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, F$_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

Compound 1 was synthesised as described in WO 2010/043880 (Compound 17), which is herein incorporated by reference.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm Synthesis of Boronate Ester

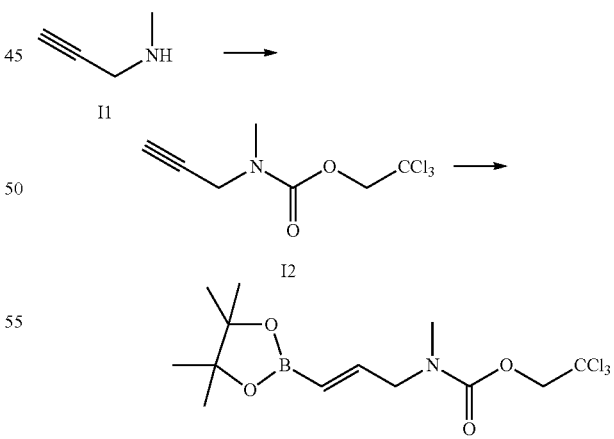

(a) Methyl-prop-2-ynyl-carbamic acid 2,2,2-trichloro-ethyl ester (I2)

A solution of Troc chloroformate (10.2 mL, 75.8 mmol, 1.05 eq) in DCM (100 mL) was added dropwise to a solution of N-methylpropargylamine (I1) (5 g, 72.3 mmol, 1 eq) and TEA (12.08 mL, 0.86 mmol, 1.2 eq) in DCM (150 mL) at −78° C. The reaction mixture was allowed to return to stir overnight at room temperature. The solution was washed with water (200 mL), 0.1 N aqueous citric acid (200 mL), saturated aqueous NaHCO3 (100 mL), and brine (50 mL). The organic phase was dried with magnesium sulphate and evaporated in vacuo to provide the desired product as a colorless oil (15.5 g, 93%). Not detected by LC/MS. $^1$H NMR (400 MHz, CDCl$_3$) δ 4.69 (s, 2H), 4.09 (d, 2H, J=2.4 Hz), 3.01-2.97 (m, 3H), 2.20 (t, 1H, J=2.4 Hz).

(b) Methyl-[(E)-3-(4,4,5,5-tetramethyl-[1,3,2]diox-aborolan-2-yl)-allyl]-carbamic acid 2,2,2-trichloroethyl ester (I3)

Neat BH$_3$.5Me$_2$ complex (1.7 mL, 16.8 mmol, 1.3 eq) was added dropwise to a solution of alpha (−)pinene (5.4 mL, 33.6 mmol, 2.6 eq) in dry THF (5 mL) at 0° C. under argon. The reaction was allowed to stir overnight and a white precipitate was observed. A solution of Troc protected methylpropargylamine (3 g, 13 mmol, 1 eq) in dry THF (5 mL) was added to the reaction mixture at 0° C. and the reaction was allowed to proceed overnight at room temperature. Neat acetaldehyde (22 mL, 387 mmol, 30 eq) was then added at 0° C. and the mixture was stirred for 5 hours. The volatiles were removed under vacuum. Ether (20 mL) was added, followed by pinacol (2.4 g, 20.1 mmol, 1.2 eq). The mixture was allowed to stir at room temperature overnight. The mixture was taken up in pentane (20 mL), washed with water (2×10 mL), then dried over magnesium sulphate. The volatiles were removed by rotoevaporation and the residue was purified by flash chromatography (Gradient: 0/100 to 10/90 ethyl acetate/hexane v/v). The pure fractions were visualised with potassium permanganate and pulled to yield 2.25 g (46%) of pure boronate ester. Not detected by LC/MS. $^1$H NMR (400 MHz, CDCl$_3$) δ 6.44 (dt, 1H, J=18.0 Hz, J=4.9 Hz), 5.48 (dd, 1H, J=18.0 Hz, J=1.3 Hz), 4.66 (d, 2H, J=6.3 Hz), 3.95 (dd, 2H, J=4.9 Hz, J=1.7 Hz), 2.89 (d, 2H, J=8.5 Hz), 1.20 (s, 12H).

Example 1

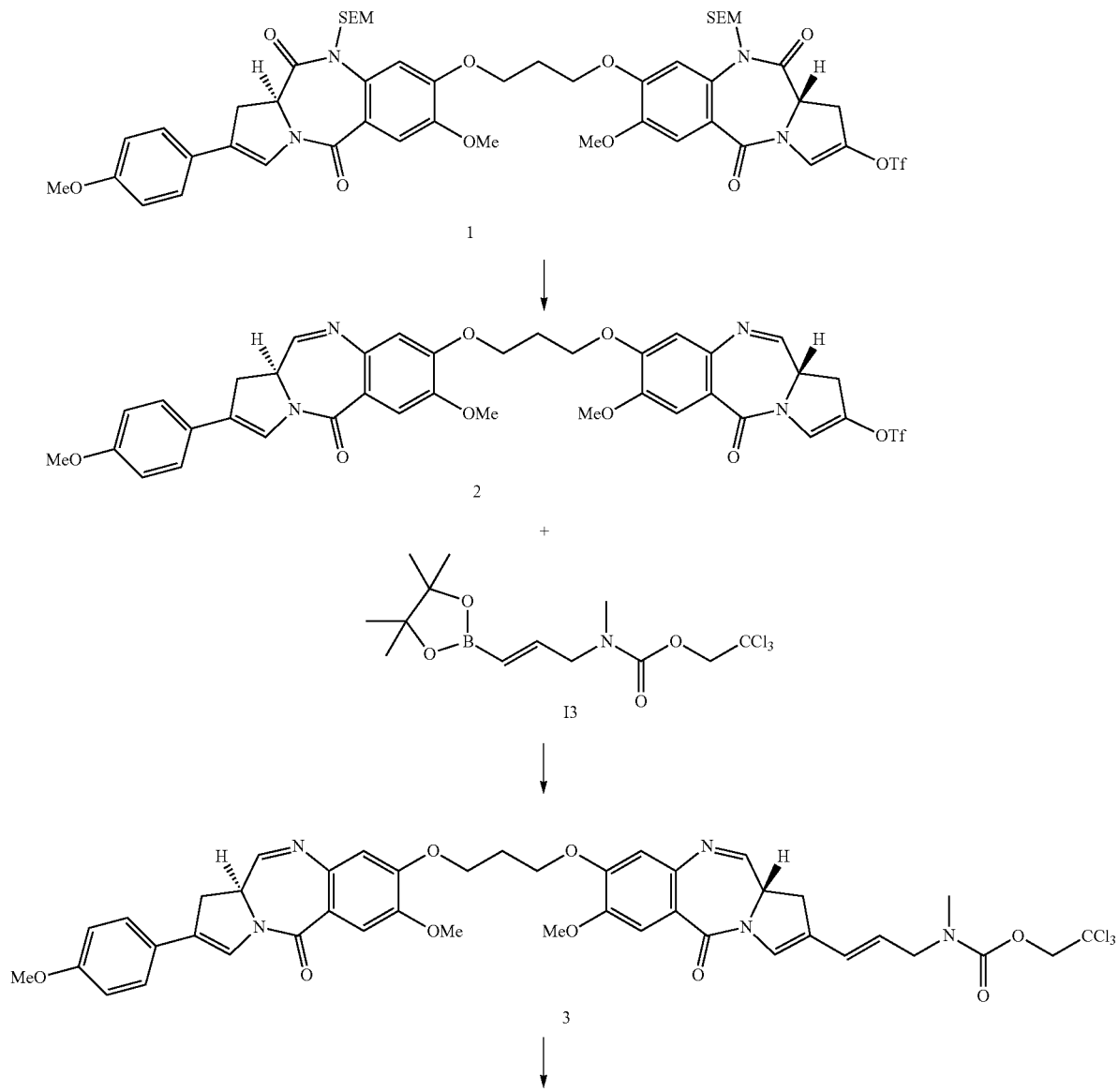

-continued

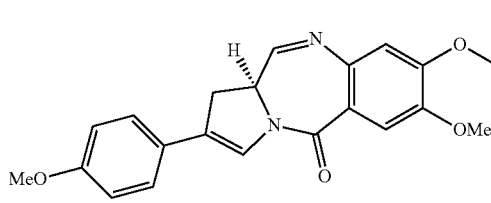 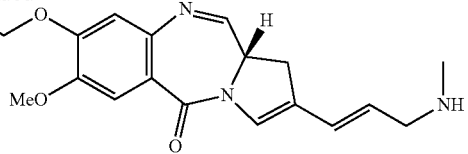

4

(a) Compound 2

Compound 1 (Compound 17 of WO 2010/0043880) was dissolved in dry THF (25 mL) and cooled at −78° C. (700 mg, 0.65 mmol, 1 eq). A solution of super hydride in THF (1M, 1.95 mL, 1.95 mmol, 3 eq) was injected slowly in the stirred reaction mixture. Reaction completion was observed after 30 minutes. The reaction mixture was quenched with water (10 mL) and later extracted with DCM (100 mL). The organics were washed with water (100 mL), then brine (50 mL). The organic phase was dried over magnesium sulphate and the volatiles removed by rotoevaporation, followed by hard vacuum. The residue was treated with DCM (50 mL), ethanol (140 mL), water (70 mL) and silica gel (100 g). The viscous mixture was allowed to stir at room temperature for 3 days. The mixture was filtered slowly through a sinter funnel and the silica residue washed with 90/10 chloroform/methanol v/v (500 mL). The organic phase was washed with water (300 mL), brine (100 mL), dried (magnesium sulphate), filtered, and evaporated in vacuo to provide the crude material which was purified by flash chromatography (gradient methanol/chloroform, 0/100 up 2.5/97.5, v/v) to yield 150 mg (29%) of relatively unstable PBD mono triflate (2) which was used directly in the next step.

(b) Compound 3

Solid Pd(PPh$_3$)$_4$ (6.6 mg, 5.7 μmol) was added to a stirred solution of the PBD mono-triflate (2)(150 mg, 0.19 mmol) and Troc-protected boronated ester (I3)(114 mg, 0.31 mmol), in toluene (8 mL), EtOH (4 mL), and Na$_2$CO$_3$ (65 mg, 0.61 mmol), in H$_2$O (4 mL) at room temperature. The reaction mixture was allowed to stir under a nitrogen atmosphere for 20 hours, at which point the reaction was deemed complete as judged by LC/MS and TLC (EtOAc). The solvent was removed by rotary evaporation under reduced pressure in vacuo and the resulting residue partitioned between EtOAc (30 mL) and H$_2$O (60 mL). The aqueous phase was extracted with EtOAc (2×30 mL) and the combined organic layers washed with H$_2$O (30 mL), brine (40 mL), dried (MgSO$_4$), filtered and evaporated to provide the crude product (3). The crude product was purified by flash chromatography (gradient methanol/chloroform, 0.5/100 up 2.5/97.5, v/v) to yield 60 mg (35.5%). LC/MS rt 3.28 min m/z (879.97) M+H.

(c) Compound 4

Finely divided, freshly prepared Cd/Pb couple (150 mg) was added to a solution of Troc protected PBD dimer (3)(55 mg, 0.070 mmol) in THF/1N aqueous ammonium acetate (1.5 mL/1.5 mL). The reaction mixture was stirred vigorously and completion was observed after 1 h. The mixture was filtered through celite and the filtrate taken up in 15% MeOH in chloroform (v/v, 3×20 mL) and 1N aqueous sodium carbonate (50 mL). The organics were washed with brine (20 mL), dried on sodium sulphate and the volatiles removed in vacuum. The crude material was purified by preparative LC/MS to provide compound 4. LC/MS rt 2.43 min m/z (704.4) M+H.

General Experimental Methods for Following Examples

LCMS data were obtained using an Agilent 1200 series LC/MS with an Agilent 6110 quadrupole MS, with Electrospray ionisation. Mobile phase A—0.1% Acetic acid in water. Mobile Phase B—0.1% in acetonitrile. Flow rate of 1.00 ml/min. Gradient from 5% B rising up to 95% B over 3 minutes, remaining at 95% B for 1 minute and then back down to 5% B over 6 seconds. The total run time is 5 minutes. Column: Phenomenex Gemini-NX 3 μm C18, 30×2.00 mm. Chromatograms based on UV detection at 254 nm. Mass Spectra were achieved using the MS in positive mode. Proton NMR chemical shift values were measured on the delta scale at 400 MHz using a Bruker AV400. The following abbreviations have been used: s, singlet; d, doublet; t, triplet; q, quartet; m, multiplet; br, broad. Coupling constants are reported in Hz. Unless otherwise stated, column chromatography (by the flash procedure) were performed on Merck Kieselgel silica (Art. 9385). Mass spectroscopy (MS) data were collected using a Waters Micromass LCT instrument coupled to a Waters 2795 HPLC separations module. Thin Layer Chromatography (TLC) was performed on silica gel aluminium plates (Merck 60, F$_{254}$). All other chemicals and solvents were purchased from Sigma-Aldrich or Fisher Scientific and were used as supplied without further purification.

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, F$_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm Synthesis of Key Intermediates (i) 1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (7)

Compound 5 was synthesised as described in WO 2010/043880 (Compound 6a), which is herein incorporated by reference.

(a) 1,1'-[[(Propane-1,3-diyl)dioxy]bis[(11aS)-11-sulpho-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]](6)

Diol 5 (25.60 g, 29.9 mmol, 1.0 eq.), NaOAc (6.90 g, 84.1 mmol, 2.8 eq.) and TEMPO (0.188 g, 1.2 mmol, 0.04 eq.) were dissolved in DCM (326 mL) under nitrogen. This was cooled to −8° C. and TCCA (9.70 g, 41.7 mmol, 1.4 eq.) was added portionwise over 20 minutes during which the solution turned dark brown which lightened as reaction proceeded. After 30 mins cold DCM (200 mL) was added and mixture was filtered through celite and then washed with a solution of saturated sodium hydrogencarbonate/sodium thiosulphate (1:1 v/v; 200 mL×2). The organic layer was dried over MgSO$_4$, filtered and concentrated under reduced pressure to yield the bis ketone 6 as a yellow/orange sponge (25.5 g, 100%). LC/MS (3.173 min (ES$^+$)). m/z: 854.20 [M]$^+$. $^1$H NMR (400 MHz, CDCl$_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.9, 3.1 Hz), 4.31-4.18 (m, 6H), 3.89-3.84 (m, 8H), 3.78-3.62 (m, 4H), 3.55 (dd, 2H, J=19.3, 3.0 Hz), 2.76 (dd, 2H, J=18.6, 10.2 Hz), 2.42 (p, 2H, J=5.8 Hz), 0.98-0.91 (m, 4H), 0.00 (s, 18H).

(b) 1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione] (7)

Anhydrous 2,6-lutidine (1.984 g, 17.864 mmol, 6.22 eq.) was injected in one portion to a vigorously stirred solution of

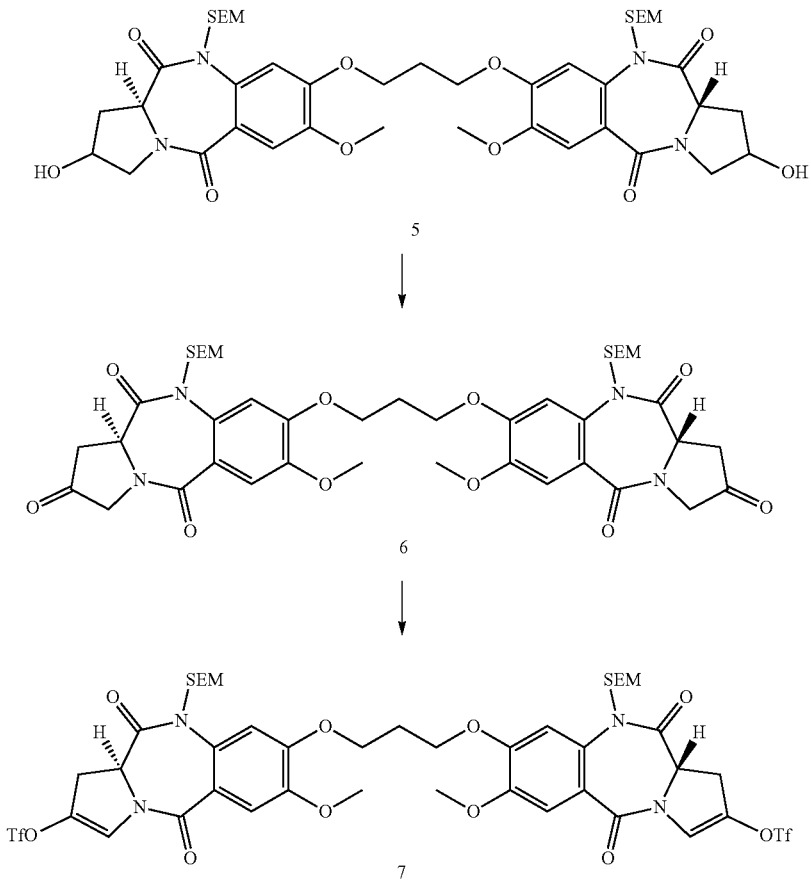 [SMILES: COc1cc2c(cc1OCCCOc1cc3c(cc1OC)C(=O)N1CC(O)C[C@H]1C(=O)N3COCC[Si](C)(C)C)N(COCC[Si](C)(C)C)C(=O)[C@@H]1CC(O)CN1C2=O ; COc1cc2c(cc1OCCCOc1cc3c(cc1OC)C(=O)N1CC(=O)C[C@H]1C(=O)N3COCC[Si](C)(C)C)N(COCC[Si](C)(C)C)C(=O)[C@@H]1CC(=O)CN1C2=O ; COc1cc2c(cc1OCCCOc1cc3c(cc1OC)C(=O)N1C=C(OS(=O)(=O)C(F)(F)F)C[C@H]1C(=O)N3COCC[Si](C)(C)C)N(COCC[Si](C)(C)C)C(=O)[C@@H]1CC(OS(=O)(=O)C(F)(F)F)=CN1C2=O]

bis-ketone 6 (2.45 g, 2.977 mmol, 1.0 eq.) in dry DCM (90 mL) at −45° C. (dry ice/acetonitrile) under a nitrogen atmosphere. Anhydrous triflic anhydride (5.04 g, 17.86 mmol, 6.0 eq.) taken from a freshly opened ampule was injected rapidly dropwise while maintaining the temperature no higher than −40° C. The reaction mixture was allowed to stir at −45° C. for 1 hour at which point TLC (50/50 v/v n-hexane/EtOAc) and LCMS revealed complete consumption of the starting material. The cold reaction mixture was immediately diluted with DCM (100 mL) and, with vigorous shaking, washed with water (1×50 mL), 5% citric acid solution (1×100 mL), saturated NaHCO$_3$ (100 mL), brine (50 mL) and dried over MgSO$_4$, filtered and concentrated under reduced pressure to give the crude product which was purified by flash chromatography (silica gel, gradient elution 90:10 n-hexane/EtOAc v/v to 60:40 n-hexane/EtOAc v/v) to afford the bis enol triflate 7 as a yellow foam (2.097 g, 63%). LC/MS (3.916 min (ES$^+$)). m/z: 1117.24 [M]$^+$. $^1$H NMR (400 MHz, CDCl$_3$) δ 7.33 (s, 2H), 7.26 (s, 2H), 7.14 (t, 2H, J=2.0 Hz), 5.51 (d, 2H, J=10.1 Hz), 4.76 (d, 2H, J=10.1 Hz), 4.62 (dd, 2H, J=11.0, 3.6 Hz), 4.32-4.23 (m, 4H), 3.94-3.90 (m, 8H), 3.81-3.64 (m, 4H), 3.16 (ddd, 2H, J=16.4, 11.1, 2.3 Hz), 2.43 (p, 2H, J=5.9 Hz), 1.23-0.92 (m, 4H), 0.02 (s, 18H).

(ii) (E)-(9H-fluoren-9-yl)methyl 3-(4,4,5,5-tetramethyl-1,3,2-dioxaborolan-2-yl)allylcarbamate (10)

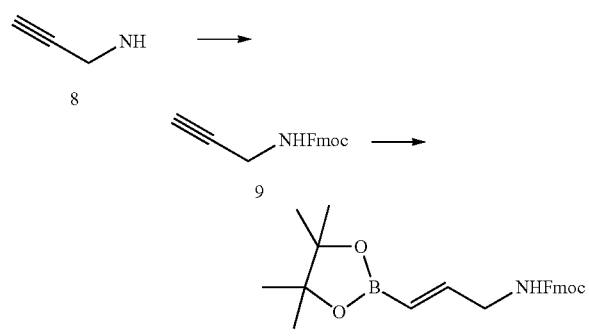

(a) (9H-fluoren-9-yl)methyl prop-2-ynylcarbamate (9)

A solution of Fmoc chloride (25.00 g, 96.64 mmol, 1.05 eq.) in DCM (150 mL) was added dropwise to a solution of propargylamine 8 (5.89 mL, 92.04 mmol, 1.0 eq.) and triethylamine (15.4 mL, 110.4 mmol, 1.2 eq.) in DCM (200 mL) at −78° C. The reaction mixture was allowed to stir at room temperature, and after 16 hours the solution was washed with water (300 mL), 0.1 N aqueous citric acid (300 mL), saturated aqueous NaHCO$_3$ (300 mL) and brine (200 mL). The organic phase was dried over magnesium sulphate, filtered and concentrated under reduced pressure to provide an amorphous white powder. Sonication in cold hexane (200 mL) followed by filtration afforded the product as a white solid (24.316 g, 95%). LC/MS (2.758 min (ES$^+$)). m/z: 300.0 [M+Na]$^+$. $^1$H NMR (400 MHz, CDCl$_3$) δ 7.74 (d, 2H, J=7.6 Hz), 7.57 (d, 2H, J=7.4 Hz), 7.41-7.37 (m, 2H), 7.30 (dt, 2H, J=7.5, 1.2 Hz), 4.93 (br s, 1H), 4.41 (d, 2H, J=6.9 Hz), 4.21 (t, 1H, J=6.4 Hz), 3.99 (d, 2H, J=3.3 Hz), 2.24 (t, 1H, J=2.5 Hz).

(b) (E)-(9H-fluoren-9-yl)methyl 3-(4,4,5,5-tetramethyl-1,3,2-dioxaborolan-2-yl)allylcarbamate (10)

Neat BH$_3$.5Me$_2$ complex (9.35 mL, 92.47 mmol, 1.3 eq.) was added dropwise to a solution of alpha (−)pinene (25.20 g, 19.72 mmol, 2.6 eq.) in dry THF (40 mL) at 0° C. under nitrogen. The reaction was allowed to stir overnight and a white precipitate was observed. A solution of Fmoc propargylamine 9 (19.72 g, 71.13 mmol, 1.0 eq.) in dry THF (40 mL) was added to the reaction mixture at 0° C. and the reaction was allowed to proceed overnight at room temperature causing the white precipitate to dissolve and form a pale straw suspension. Neat acetaldehyde (121.32 mL, 2.134 mol, 30.0 eq.) was then added at 0° C. and the mixture was stirred for 5 hours. The volatiles where removed under reduced pressure. Diethyl ether (125 mL) was added, followed by pinacol (10.08 g, 85.36 mmol, 1.2 eq.). The mixture was allowed to stir at room temperature overnight. The mixture was taken up in DCM (125 mL), washed with water (2×75 mL), then dried over magnesium sulphate. The volatiles were removed by concentration under reduced pressure and the residue was purified by flash chromatography (0/100 to 60/40 ethyl acetate/hexane v/v). The product fractions were combined and concentrated under reduced pressure to give a colourless oil which was taken up in a small amount of DCM, cooled to −78° C. and hexane added until a white precipitate formed. The suspension was allowed to stir for 5 minutes and filtered to afford the product as a white solid (14.09 g, 49%). LC/MS (min (ES$^+$)). m/z: [M]$^+$. $^1$H NMR (400 MHz, CDCl$_3$)) δ 7.76 (d, 2H, J=7.6 Hz), 7.59 (d, 2H, J=7.4 Hz), 7.40 (t, 2H, J=7.4 Hz), 7.32 (t, 2H, J=7.4 Hz), 6.59 (dt, 1H, J=18.0, 4.7 Hz), 5.60 (d, 2H, J=18.0 Hz), 4.90-4.83 (m, 1H), 4.40 (d, 2H, J=7.1 Hz), 4.22 (t, 1H, J=7.1 Hz), 3.92 (t, 1H, J=4.7 Hz), 1.27 (s, 12H).

(iii) (S)-2-((S)-2-(((9H-fluoren-9-yl)methoxy)carbonylamino)-3-methylbutanamido)propanoic acid (HO-Ala-Val-Fmoc) (12)

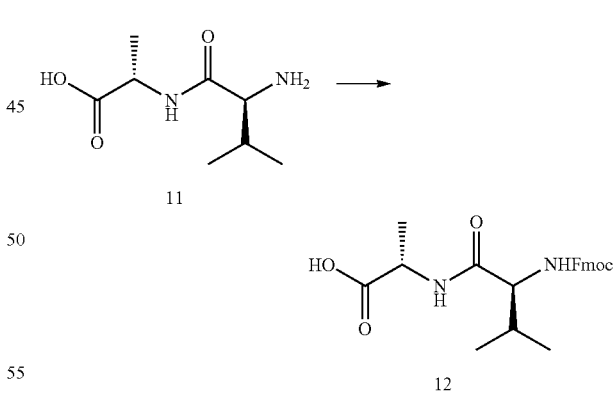

H-Val-Ala-OH 11 (1.0 g, 5.313 mmol, 1.0 eq.) and Na$_2$CO$_3$ (1.42 g, 13.282 mmol, 2.5 eq.) were solubilised in distilled H$_2$O (40 mL) and the mixture was cooled to 0° C. before dioxane (40 mL) was added. Partial precipitation of the amino acid salt occurred. A solution of Fmoc-Cl (1.44 g, 5.579 mmol, 1.05 eq.) dissolved in dioxane (40 mL) was added dropwise with vigorous stirring over 10 minutes. The resulting mixture was stirred at 0° C. for 2 hours before the ice bath was removed and the stirring maintained for 16 hours. The solvent was evaporated under reduced pressure and the solid remaining dissolved in water (450 mL). The pH was adjusted to 2 with 1N HCl (25 mL) and the aqueous layer was subsequently extracted with EtOAc (3×250 mL). The combined organics were washed with brine (100 mL), dried over MgSO$_4$, filtered and the volatiles removed under reduced pressure to afford pure HO-Ala-Val-Fmoc 12 as a white solid (2.06 g, 94%). LC/MS (2.758 min (ES$^+$)), m/z: 411.0 [M+H]$^+$. $^1$H NMR (400 MHz, DMSO-d$_6$) δ 12.47 (br s, 1H), 8.20 (d, 1H, J=6.7 Hz), 7.89 (d, 2H, J=7.5 Hz), 7.75 (t, 2H, J=6.8 Hz), 7.43-7.38 (m, 3H), 7.34-7.30 (m, 2H), 4.31-4.16 (m, 4H), 3.88 (dd, 1H, J=8.8, 7.2 Hz), 1.98 (m, 1H), 1.26 (d, 3H, J=7.3 Hz), 0.89 (d, 3H, J=6.8 Hz), 0.86 (d, 3H, J=6.8 Hz).

Example 2

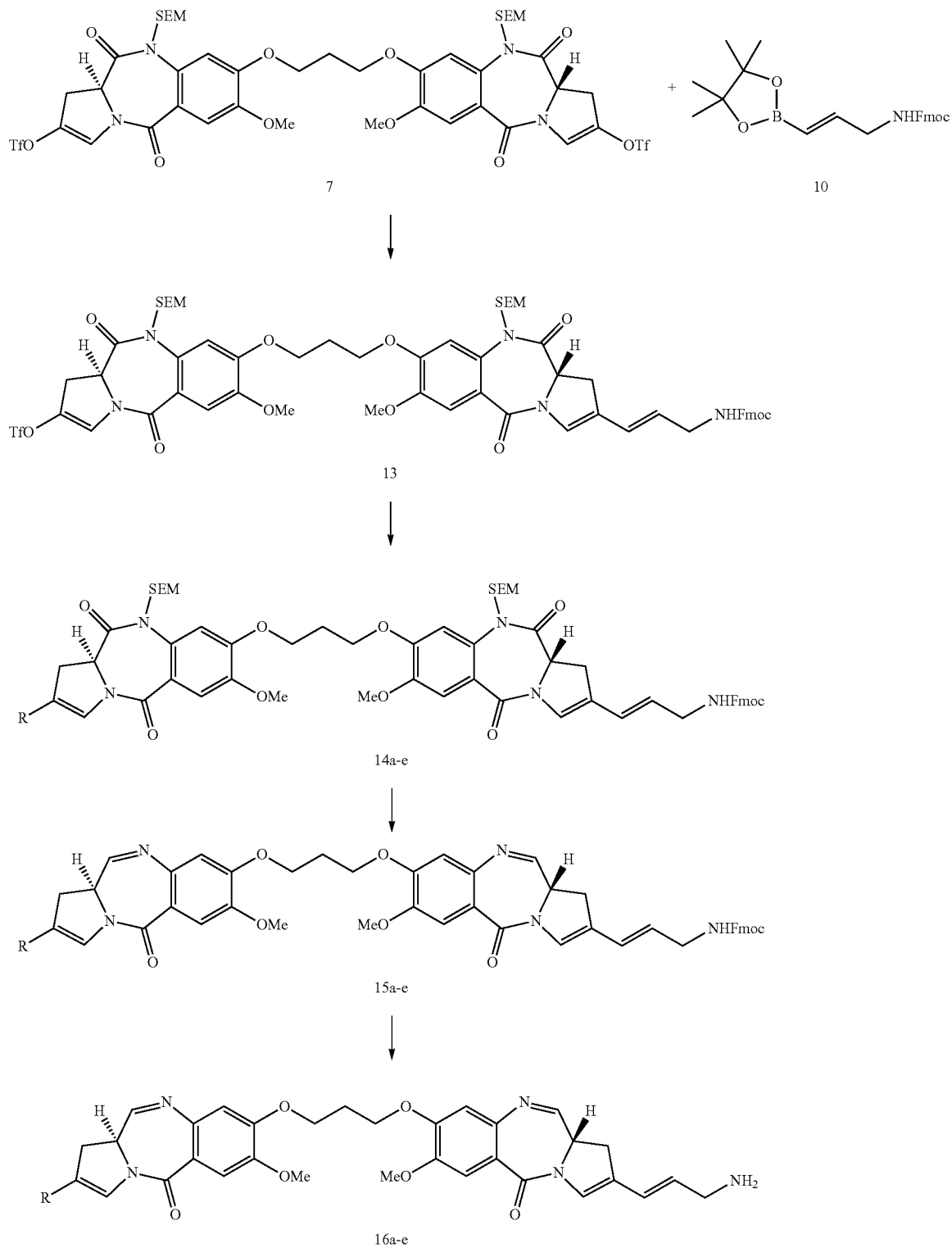

R

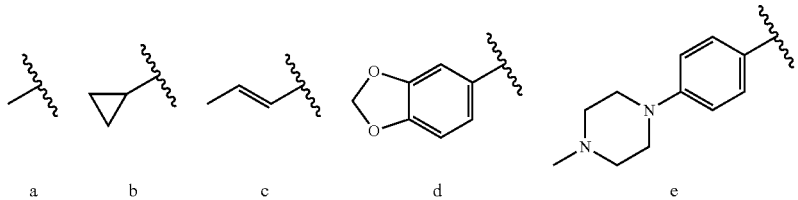

a  b  c  d  e (a) (S)-8-(3-(((S)-2-((E)-3-(((9H-fluoren-9-yl)methoxy)carbonylamino)prop-1-enyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (13)

A suspension of the boronic ester 10 (2.19 g, 5.61 mmol, 0.95 eq.) in toluene (6 mL) was added dropwise over 1 hour to a stirring solution of the bis-enol triflate 7 (6.6 g, 5.91 mmol, 1.0 eq.), tetrakis(triphenylphosphine)palladium(0) (0.273 g, 0.236 mmol, 0.04 eq.), sodium carbonate (2.00 g, 18.91 mmol, 3.2 eq.) in methanol (28 mL), toluene (56 mL) and water (34 mL). The reaction mixture was allowed to stir at room temperature overnight, then concentrated to dryness and the residue was taken up in EtOAc (200 mL) and washed with water (2×150 mL), brine (150 mL), dried over MgSO$_4$, filtered and concentrated under reduced pressure The crude product was purified by flash chromatography (silica gel, 80:20 hexane/EtOAc v/v to 10:90 hexane/EtOAc then neat EtOAc) to afford recovered 7, product and bis-substituted impurity. 2.49 g (37%) of 13 as a yellow solid. LC/MS (3.930 min (ES$^+$)), m/z: 1247.39 [M+H]$^+$. $^1$H NMR (400 MHz, CDCl$_3$) δ 7.78 (d, 2H, J=7.6 Hz), 7.60 (d, 2H, J=7.4 Hz), 7.41 (t, 2H, J=7.6 Hz), 7.36-7.31 (m, 1H), 7.14 (m, 1H), 6.96 (m, 1H), 6.36 (d, 1H, J=14.4 Hz), 5.69-5.59 (m, 1H), 5.51 (dd, 2H, J=10.1, 3.0 Hz), 4.87-4.81 (m, 1H), 4.75 (dd, 2H, J=10.1, 7.9 Hz), 4.61 (dd, 1H, J=10.9, 3.6 Hz), 4.54 (dd, 2H, J=10.6, 3.3 Hz), 4.43 (d, 2H, J=6.6 Hz), 4.31-4.20 (m, 6H), 3.95-3.87 (m, 9H), 3.81-3.63 (m, 6H), 3.15 (ddd, 1H, J=16.2, 10.9, 2.3 Hz), 2.93-2.83 (m, 1H), 2.43 (hep, 1H, J=5.8 Hz), 1.00-0.92 (m, 4H), 0.01 (s, 18H). 2.06 g (33%) of 7. LC/MS (3.916 min (ES$^+$)). 0.770 g of bis-substituted impurity as a yellow solid. LC/MS (3.977 min (ES$^+$)). m/z: 1376.52 [M+H]$^+$.

(b) Compounds 14a-e (i) (9H-fluoren-9-yl)methyl(E)-3-((S)-7-methoxy-8-(3-((S)-7-methoxy-2-methyl-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylcarbamate (14a)

Triphenylarsine (0.010 g, 0.0321 mmol, 0.8 eq.) was added to a mixture of triflate 13 (0.050 g, 0.0401 mmol, 1.0 eq.), methylboronic acid (0.012 g, 0.20 mmol, 5.0 eq.), silver oxide (0.074 g, 0.321 mmol, 8.0 eq.) and potassium phosphate tribasic (0.102 g, 0.481 mmol, 12.0 eq.) in dry dioxane (2 mL) under a nitrogen atmosphere. The reaction was flushed with nitrogen and bis(benzonitrile)palladium(II) chloride (0.003 g, 0.00802 mmol, 0.2 eq.) was added. The reaction was flushed with nitrogen once more before being warmed to 70° C. for 1 hour. The reaction conditions above were repeated on 0.200 g of triflate 13, and the combined reaction mixtures were filtered through a pad of Celite® with ethyl acetate washings. The crude material was concentrated under reduced pressure and purified by flash chromatography to afford the product as a pale yellow solid (0.010 g, 56%). LC/MS (3.823 min (ES$^+$)), m/z: 1112.92 [M+H]$^+$.

(ii) (9H-fluoren-9-yl)methyl(E)-3-((S)-7-methoxy-8-(3-((S)-7-methoxy-5,11-dioxo-2-((E)-prop-1-enyl)-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylcarbamate (14c)

Trans-1-propen-1-ylboronic acid (0.103 g, 1.20 mmol, 3.0 eq.), triethylamine (0.220 ml, 1.60 mmol, 4.0 eq.) and mono triflate 13 (0.500 g, 0.401 mmol, 1.0 eq.) were dissolved in a mixture of ethanol (10 mL), toluene (20 mL) and water (3 mL) under a nitrogen atmosphere. The reaction mixture was degassed under nitrogen for 5 minutes and tetrakis(triphenylphosphine)palladium(0) (0.018 g, 0.016 mmol, 0.04 eq.) added. The reaction mixture was stirred at 60° C. for 50 minutes, then concentrated to dryness under reduced pressure and the crude solid was purified by flash chromatography (silica gel, 50:50 acetate/hexane v/v then 66:33 ethyl acetate/hexane v/v) to afford the product as pale yellow solid. (0.35 g, 77%). LC/MS (3.910 min (ES$^+$)), m/z: 1137.86 [M+H]$^+$.

(iii) (9H-fluoren-9-yl)methyl(E)-3-((S)-8-(3-((S)-2-(benzo[d][1,3]dioxol-5-yl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylcarbamate (14d)

3,4-(methylenedioxy)phenyl boronic acid (0.027 g, 0.160 mmol, 2.0 eq.), triethylamine (0.065 g, 0.064 mmol, 8.0 eq.) and mono triflate 13 (0.100 g, 0.080 mmol, 1.0 eq.) were dissolved in a mixture of ethanol (1 mL), toluene (2 mL) and water (0.4 mL) under nitrogen. The reaction vessel was evacuated and flushed with nitrogen three times before the addition of tetrakis(triphenylphosphine)palladium(0) (0.006 g, 0.005 mmol, 0.06 eq.). The flask was then evacuated and flushed with nitrogen three times and heated under microwave irradiation at 80° C. for 8 minutes. This reaction was repeated twice on 0.100 g scale and once on 0.130 g scale. The crude reaction mixtures were combined, diluted with DCM (10 mL) and washed with H₂O (10 mL). The organic layer was dried over MgSO₄, filtered and concentrated under reduced pressure and the residue was purified by flash chromatography (silica gel, 30/70 to 20/80 v/v hexane/ethyl acetate) to afford the product as a pale yellow solid (0.199 g, 62%). LC/MS (3.887 min (ES+)), m/z: 1217.57 [M+H]+. ¹H NMR (400 MHz, CDCl₃) δ 7.77 (d, 2H, J=7.4 Hz), 7.60 (d, 2H, J=7.5 Hz), 7.43-7.29 (m, 7H), 6.97-6.94 (m, 2H), 6.88 (dd, 2H, J=7.8, 1.7 Hz), 6.78 (d, 2H, J=8.1 Hz), 6.35 (d, 1H, J=15.7 Hz), 5.97 (s, 2H), 5.69-5.59 (m, 1H), 5.50 (dd, 2H, J=10.1, 2.7 Hz), 4.84 (m, 1H), 4.75 (dd, 2H, J=10.1, 5.8 Hz), 4.61-4.52 (m, 3H), 4.44 (d, 1H, J=6.9 Hz), 4.32-4.20 (m, 6H), 3.94-3.87 (m, 9H), 3.81-3.64 (m, 6H), 3.15 (ddd, 1H, J=16.2, 10.6, 1.9 Hz), 2.88 (m, 1H), 2.43 (m, 1H), 0.99-0.95 (m, 4H), 0.01 (s, 18H).

(iv) (9H-fluoren-9-yl)methyl(E)-3-((S)-7-methoxy-8-(3-((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylcarbamate (14e)

Mono triflate 13 (0.100 g, 0.0802 mmol, 1.0 eq.), (4-methylpiperazin-1-yl)phenylboronic acid, pinacol ester (0.023 g, 0.0762, 0.95 eq.) and triethylamine (0.051 mL, 0.369 mmol, 4.6 eq.) were solubilised in a mixture of Toluene/Ethanol/H₂O [6:3:1] (4 mL) under a nitrogen atmosphere. The reaction was flushed with nitrogen for 5 minutes and palladium-tetrakistriphenylphosphine (0.9 mg, 0.000802 mmol, 0.01 eq.) was added. The reaction was then subjected to microwave irradiation at 80° C. for 5 minutes. The above reaction was repeated 3 times on 0.100 g scale. The combined reaction mixtures were concentrated under reduced pressure, and the solid residue was partitioned between H₂O (180 mL) and ethyl acetate (180 mL). The aqueous layer was extracted with ethyl acetate (2×180 mL) before the combined organics were washed with brine (180 mL), dried over MgSO₄, filtered and concentrated under reduced pressure. The resulting crude mixture was purified by flash chromatography (silica gel, 40:1 v/v DCM/MeOH to 20:1 v/v DCM/MeOH) to afford the desired product as a yellow solid (0.220 g, 54%). LC/MS (2.833 min (ES+)), m/z: 1272.53 [M+H]+. ¹H NMR (400 MHz, CDCl₃) δ 7.77 (d, 2H, J=7.5 Hz), 7.60 (d, 2H, J=7.3 Hz), 7.43-7.39 (m, 3H), 7.35-7.30 (m, 6H), 6.95 (m, 1H), 6.90-6.87 (m, 1H), 6.34 (d, 1H, J=15.7 Hz), 5.67-5.57 (m, 1H), 5.50 (dd, 2H, J=10.1, 3.3 Hz), 4.86 (m, 1H), 4.75 (dd, 2H, J=10.1, 5.6 Hz), 4.54 (m, 2H), 4.44 (d, 2H, J=6.8 Hz), 4.31-4.21 (m, 6H), 3.96-3.87 (m, 9H), 3.81-3.73 (m, 3H), 3.71-3.62 (m, 3H), 3.31-3.20 (m, 5H), 3.10 (m, 1H), 2.87 (m, 1H), 2.58 (m, 4H), 2.43 (m, 2H), 2.36 (s, 3H), 0.97 (m, 4H), 0.01 (s, 18H).

(c) Compounds 15a-e (i) (9H-fluoren-9-yl)methyl(E)-3-((S)-8-(3-((S)-2-(benzo[d][1,3]dioxol-5-yl)-7-methoxy-5-oxo-5,11a-dihydro-1H-benzo[e]pyrrolo[1,2-a][1,4]diazepin-8-yloxy)propoxy)-7-methoxy-5-oxo-5,11a-dihydro-1H-benzo[e]pyrrolo[1,2-a][1,4]diazepin-2-yl)allylcarbamate (15d)

SEM dilactam 14d (0.223 g, 0.183 mmol, 1.0 eq.) was solubilised in THF (10 mL) and cooled to −78° C. under a nitrogen atmosphere. Super hydride solution (0.373 mL, 0.373 mmol, 2.04 eq.). was added dropwise over 5 minutes. After 20 minutes an aliquot was washed with water for LCMS and TLC analysis and after 30 minutes water (30 mL) was added and the cold bath removed. The organic layer was extracted with EtOAc (2×30 mL) and the combined organic extracts washed with brine (30 mL), dried over MgSO₄, filtered and concentrated under reduced pressure. The crude product was dissolved in MeOH (12 mL), DCM (6 mL) and water (2 mL) and enough silica gel to form a thick stirring suspension which was left for 5 days. The suspension was filtered and washed with DCM/MeOH 9:1 (~200 mL) until complete elution of product. The organic layer was washed with brine (2×70 mL), dried over MgSO₄, filtered and concentrated under reduced pressure and the residue was purified by flash chromatography (silica gel, 100/0 to 90/10 v/v CHCl₃/MeOH) to afford the product as a yellow solid (0.133 g, 79%). LC/MS (2.916 min (ES+)), m/z: 926.33 [M+H]+.

(ii) (9H-fluoren-9-yl)methyl(E)-3-((S)-7-methoxy-8-(3-((S)-7-methoxy-2-(4-(4-methylpiperazin-1-yl)phenyl)-5-oxo-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylcarbamate (15e)

SEM dilactam 14e (0.250 g, 0.196 mmol, 1.0 eq.) was solubilised in THF (13 mL) and cooled to −78° C. under a nitrogen atmosphere. Super hydride solution (0.40 mL, 0.401 mmol, 2.04 eq.) was added dropwise over 5 min. After 20 min an aliquot was washed with water for LCMS and TLC analysis. After 30 mins water (30 mL) was added and the cold bath removed. The organic layer was extracted with EtOAc (2×40 mL) and the combined organic extracts washed with brine (40 mL), dried with MgSO₄, filtered and removed under reduced pressure. The crude product was dissolved in MeOH (13 mL), DCM (7 mL) and water (1.7 mL) and enough silica gel to form a thick stirring suspension. After 5 days the suspension was filtered through a sintered funnel and washed with DCM/MeOH 9:1 (~200 mL) until complete elution of product. The organic layer was washed with brine (2×70 mL), dried with MgSO₄, filtered and the solvent removed under reduced pressure. Purification by flash chromatography (silica gel, CHCl₃ 100 to 96:4 v/v CHCl₃/MeOH) afforded the product as a pale yellow solid (0.090 g, 47%). LC/MS (2.112 min (ES+)), m/z: 981.0 [M+H]+.

(d) Compounds 16a-e (i) (S)-2-(E)-3-aminoprop-1-enyl)-8-(3-((S)-2-(benzo[d][1,3]dioxol-5-yl)-7-methoxy-5-oxo-5,11a-dihydro-1H-benzo[e]pyrrolo[1,2-a][1,4]diazepin-8-yloxy)propoxy)-7-methoxy-1H-benzo[e]pyrrolo[1,2-a][1,4]diazepin-5(11aH)-one (16d)

Piperidine (6 drops, excess) was added to a stirring mixture of Fmoc allylamine 15d (0.030 g, 0.0306 mmol, 1.0 eq.) in anhydrous DMF (0.30 mL) and the mixture was stirred at ambient temperature. After 20 minutes, LCMS of the reaction mixture showed reaction completion and the reaction mixture was diluted with DCM (30 mL) and washed with water (3×30 mL). The organic layer was dried over MgSO₄, filtered and concentrated under reduced pressure. The crude material was dissolved in chloroform and the resulting precipitate was collected by filtration to afford the product as an orange solid (0.003 g, 13%). LC/MS (1.802 min (ES+)), m/z: 704.1 [M+H]+.

(ii) (S)-2-((E)-3-aminoprop-1-enyl)-7-methoxy-8-(3-((S)-7-methoxy-2-(4-(4-methylpiperazin-1-yl)phenyl)-5-oxo-5,11a-dihydro-1H-benzo[e]pyrrolo[1,2-a][1,4]diazepin-8-yloxy)propoxy)-1H-benzo[e]pyrrolo[1,2-a][1,4]diazepin-5(11aH)-one (16e)

Piperidine (4 drops, excess) was added to a stirring mixture of Fmoc allylamine 15e (0.02 g, 0.0204 mmol, 1.0 eq.) in anhydrous DMF (0.25 mL) and the mixture was stirred at ambient temperature. After 30 minutes, the reaction mixture was diluted with DCM (30 mL) and washed with water (3×30 mL). The organic layer was dried over MgSO$_4$, filtered and concentrated under reduced pressure. The crude material was dissolved in chloroform and the resulting precipitate was collected by filtration to afford the product as an orange solid (0.001 g, 7%). LC/MS (1.495 min (ES$^+$)), m/z: 379.5 ½[M+2H]$^+$.

Synthesis of Key Intermediate

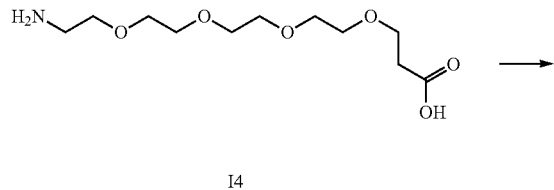

I4

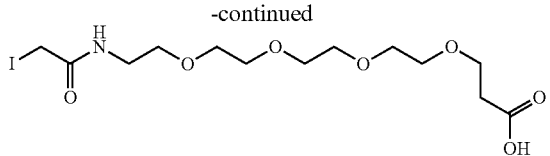

I5

1-iodo-2-oxo-6,9,12,15-tetraoxa-3-azaoctadecan-18-oic acid (I5)

A solution of iodoacetic anhydride (0.250 g, 0.706 mmol, 1.1 eq) in dry DCM (1 mL) was added to amino-PEG$_{(4)}$-acid I4 (0.170 g, 0.642 mmol, 1.0 eq) in DCM (1 mL). The mixture was stirred in the dark at room temperature overnight. The reaction mixture was washed with 0.1 M HCl, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as an orange oil (0.118 g, 42%). LC/MS (1.623 min (ES$^+$)), m/z: 433.98 [M+H]$^+$. $^1$H NMR (400 MHz, CDCl$_3$) δ 8.069 (s, 1H), 7.22 (br s, 1H), 3.79 (t, 2H, J=5.8 Hz), 3.74 (s, 2H), 3.72-3.58 (m, 14H), 3.50-3.46 (m, 2H), 2.62 (t, 2H, J=5.8 Hz).

Example 3

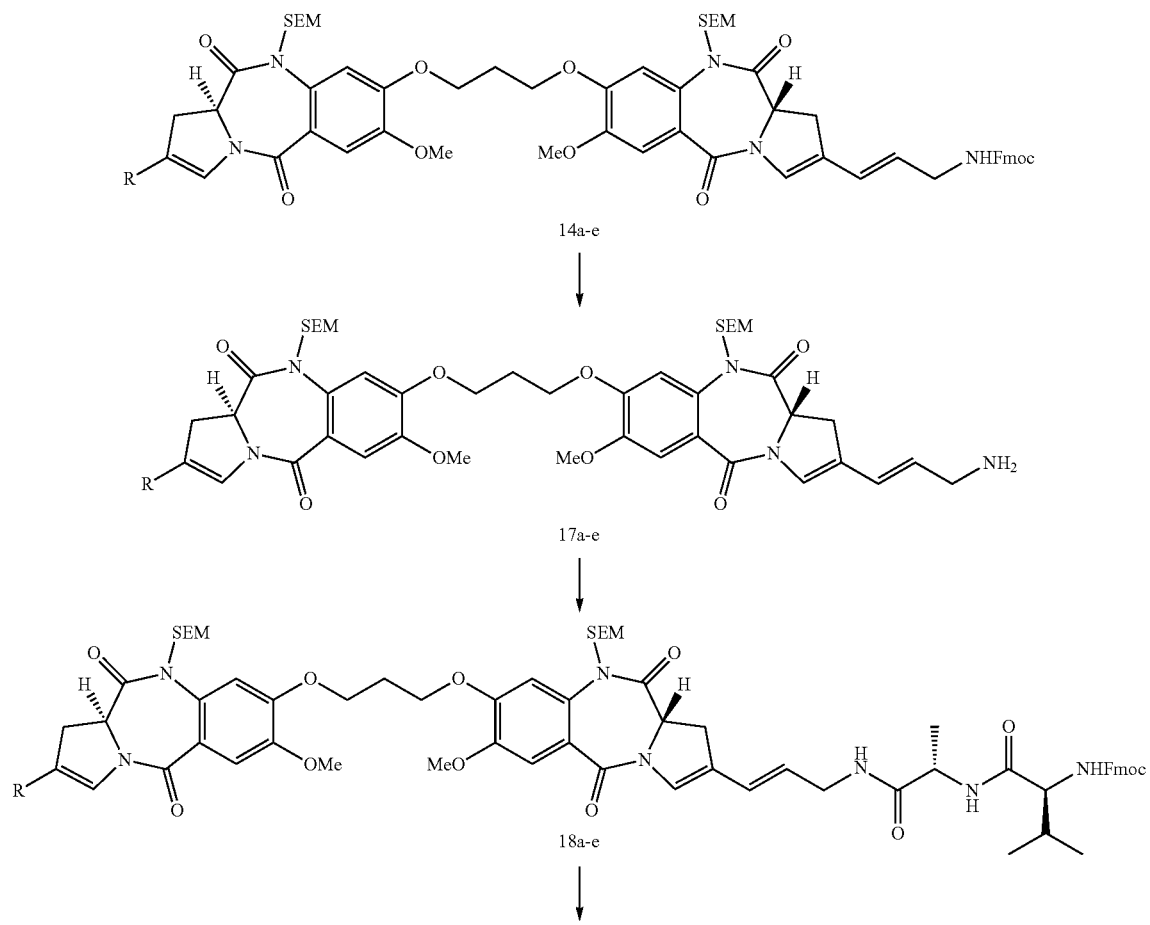

-continued

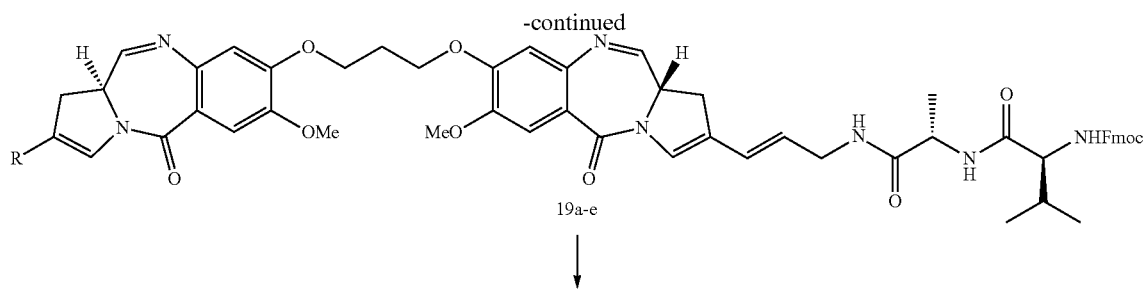
19a-e

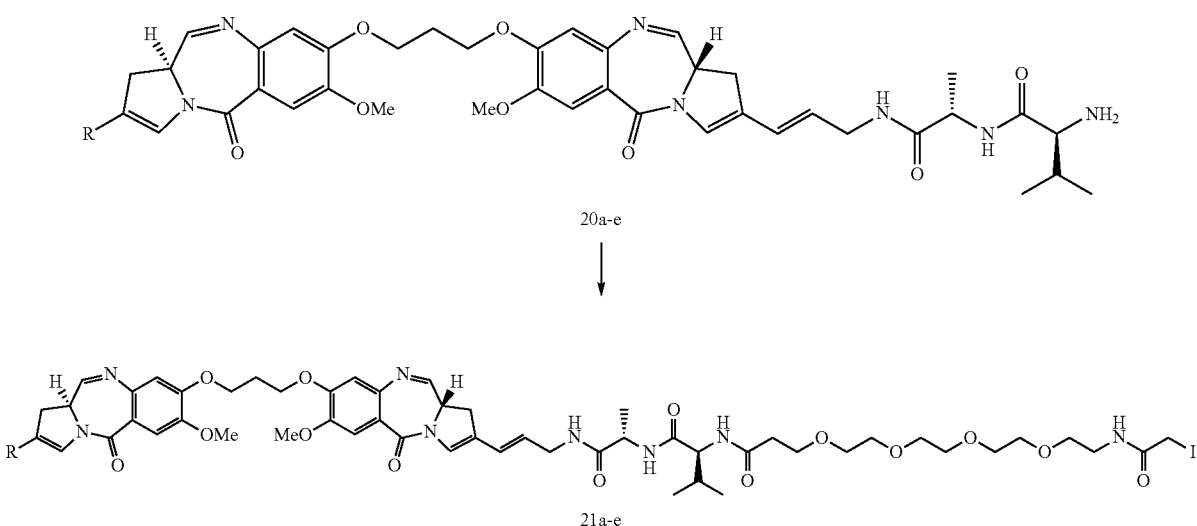
20a-e 21a-e

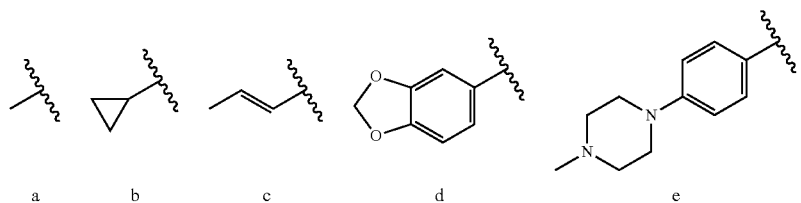

a    b    c    d    e (a) Compounds 17a-e (i) (S)-2-((E)-3-aminoprop-1-enyl)-7-methoxy-8-(3-((S)-7-methoxy-2-methyl-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-10-((2-(trimethylsilyl)ethoxy)methyl)-1H-benzo[e]pyrrolo[1,2-a][1,4]diazepine-5,11(10H,11aH)-dione (17a)

Piperidine (0.133 mL, 1.35 mmol, 12 eq.) was added to a stirred solution of Fmoc amine 14a (0.125 g, 0.112 mmol, 1.0 eq.) in DMF (1.8 ml). After stirring at room temperature for 30 minutes, LCMS analysis indicated consumption of starting material and the reaction mixture was diluted with DCM (200 mL) and washed with water (3×200 mL). The organic layer was dried over MgSO$_4$, filtered and concentrated to dryness to afford the crude product which did not undergo further purification (0.100 g, assumed 100% yield). This material was used without further characterisation.

(ii) (S)-2-((E)-3-aminoprop-1-enyl)-7-methoxy-8-(3-((S)-7-methoxy-5,11-dioxo-2-((E)-prop-1-enyl)-10-((2-(trimethylsilyl)ethoxy)methyl)-5,10,11,11a-tetrahydro-1H-benzo[e]pyrrolo[1,2-a][1,4]diazepin-8-yloxy)propoxy)-10-((2-(trimethylsilyl)ethoxy)methyl)-1H-benzo[e]pyrrolo[1,2-a][1,4]diazepine-5,11(10H,11aH)-dione (17c)

Piperidine (0.40 mL, 4.0 mmol, 12 eq.) was added to a stirred solution of Fmoc amine 14c (0.380 g, 0.334 mmol, 1.0 eq.) in DMF (5.0 mL). After stirring at room temperature for 20 minutes, LCMS analysis indicated consumption of starting material and the reaction mixture was diluted with DCM (300 mL) and washed with water (3×300 mL). The organic layer was dried over MgSO$_4$, filtered and concentrated to dryness under reduced pressure to afford the crude product which did not undergo further purification (0.306 g, assumed 100% yield).

LC/MS (2.533 min (ES$^+$)), m/z: 916.3 [M+H]$^+$.

(iii) (S)-2-((E)-3-aminoprop-1-enyl)-7-methoxy-8-(3-((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-10-((2-(trimethylsilyl)ethoxy)methyl)-1H-benzo[e]pyrrolo[1,2-a][1,4]diazepine-5,11(10H,11aH)-dione (17e)

Piperidine (0.40 mL, 4.0 mmol, 14.2 eq.) was added to a stirred solution of Fmoc amine 14e (0.358 g, 0.282 mmol, 1.0 eq.) in DMF (5.0 mL). The clear solution was stirred at room temperature for 30 minutes. The reaction mixture was diluted with DCM (300 mL) and washed with water (3×300 mL). The organic layer was dried over MgSO$_4$, filtered and concentrated under reduced pressure to afford the crude product which did not undergo further purification (0.296 g, assumed 100% yield). LC/MS (2.049 min (ES$^+$)), m/z: 1051.2 [M+H]$^+$.

(b) Compounds 18a-e (i) (9H-fluoren-9-yl)methyl (R)-1-((S)-1-((E)-3-((S)-7-methoxy-8-(3-((S)-7-methoxy-2-methyl-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylamino)-1-oxopropan-2-ylamino)-3-methyl-1-oxobutan-2-ylcarbamate (18a)

1-Ethyl-3-(3'-dimethylaminopropyl)carbodiimide hydrochloride (0.018 g, 0.095 mmol, 1.0 eq.) was added to a solution of allylamine 17a (assumed 100% yield, 0.100 g, 0.095 mmol, 1.0 eq.) and HO-Ala-Val-Fmoc 12 (0.036 g, 0.095 mmol, 1.0 eq.) in dry dichloromethane (6 mL). The reaction mixture was stirred for 120 minutes at room temperature when the reaction mixture was diluted with dichloromethane (10 mL) and washed sequentially with water (10 mL) and brine (10 mL). The organic layer was dried over MgSO$_4$, filtered and excess dichloromethane removed under reduced pressure. The resulting residue was purified by flash chromatography (silica gel; 100:1 v/v DCM/MeOH to 40:1 v/v DCM/MeOH) to afford the product as a yellow solid (0.050 g, 35%). LC/MS (3.677 min (ES$^+$)), m/z: 1281.42 [M+H]$^+$. $^1$H NMR (400 MHz, CDCl$_3$) δ 7.76 (d, 2H, J=7.7 Hz), 7.58 (m, 2H), 7.40 (t, 2H, J=7.6 Hz), 7.34 (d, 2H, J=5.7 Hz), 7.31 (m, 3H), 7.25 (m, 2H), 6.93 (s, 1H), 6.68 (m, 1H), 6.34 (m, 3H), 5.58 (m, 1H), 5.49 (m, 2H), 4.71 (m, 2H), 4.45 (m, 5H), 4.27 (m, 4H), 4.22 (t, 1H, J=7.0 Hz), 3.97 (m, 2H), 3.89 (m, 7H), 3.75 (m, 2H), 3.65 (m, 3H), 3.44 (m, 1H), 2.77 (m, 2H), 2.43 (m, 2H), 2.14 (m, 1H), 1.83 (d, 3H, J=1.0 Hz), 1.40 (d, 3H, J=6.9 Hz), 0.99-0.91 (m, 10H), 0.01 (s, 9H), 0.00 (s, 9H).

(ii) (9H-fluoren-9-yl)methyl(S)-1-((S)-1-((E)-3-((S)-7-methoxy-8-(3-((S)-7-methoxy-5,11-dioxo-2-((E)-prop-1-enyl)-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylamino)-1-oxopropan-2-ylamino)-3-methyl-1-oxobutan-2-ylcarbamate (18c)

1-Ethyl-3-(3'-dimethylaminopropyl)carbodiimide hydrochloride (0.0641 g, 0.334 mmol, 1.0 eq.) was added to a solution of allylamine 17c (assumed 100% yield, 0.306 g, 0.334 mmol, 1.0 eq.) and HO-Ala-Val-Fmoc 12 (0.1367 g, 0.334 mmol, 1.0 eq.) in dry dichloromethane (18 mL). The reaction mixture was stirred for 95 minutes at room temperature when the reaction mixture was diluted with dichloromethane (30 mL) and washed sequentially with water (30 mL) and brine (30 mL). The organic layer was dried over MgSO$_4$ filtered and excess dichloromethane removed under reduced pressure. The resulting residue was purified by flash chromatography (silica gel; 100:1 v/v DCM/MeOH to 40:1 v/v DCM/MeOH) to afford the product as a yellow solid (0.220 g, 50%). LC/MS (3.804 min (ES$^+$)), m/z: 1307.37 [M+H]$^+$. $^1$H NMR (400 MHz, CDCl$_3$) δ 7.76 (d, 2H, J=7.6 Hz), 7.57 (m, 2H), 7.39 (t, 2H, J=7.6 Hz), 7.34 (d, 2H, J=3.2 Hz), 7.31 (m, 3H), 7.26 (m, 1H), 6.93 (s, 1H), 6.85 (m, 1H), 6.36 (m, 2H), 6.24 (d, 1H, J=14.7 Hz), 5.68 (m, 1H), 5.58 (m, 1H), 5.49 (m, 2H), 4.72 (m, 2H), 4.83 (m, 4H), 4.39 (m, 1H), 4.27 (m, 4H), 4.22 (t, 1H, J=6.9 Hz), 3.98 (m, 3H), 3.89 (m, 8H), 3.75 (m, 2H), 3.65 (m, 4H), 2.85 (m, 2H), 2.43 (m, 2H), 2.14 (m, 1H), 1.82 (dd, 3H, J=5.8, 0.8 Hz), 1.40 (d, 3H, J=6.9 Hz), 0.99-0.92 (m, 10H), 0.01 (s, 9H), 0.00 (s, 9H).

(iii) (9H-fluoren-9-yl)methyl(S)-1-((S)-1-((E)-3-((S)-7-methoxy-8-(3-((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-benzo[e]pyrrolo[1,2-a][1,4]diazepin-8-yloxy)propoxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)allylamino)-1-oxopropan-2-ylamino)-3-methyl-1-oxobutan-2-ylcarbamate (18e)

1-Ethyl-3-(3'-dimethylaminopropyl)carbodiimide hydrochloride (0.0541 g, 0.282 mmol, 1.0 eq.) was added to a solution of allylamine 17e (assumed 100% yield, 0.296 g, 0.282 mmol, 1.0 eq.) and HO-Ala-Val-Fmoc 12 (0.116 g, 0.282 mmol, 1.0 eq.) in dry dichloromethane (18 mL). The reaction mixture was stirred for 80 minutes at room temperature when the reaction mixture was diluted with dichloromethane (30 mL) and washed sequentially with water (30 mL) and brine (30 mL). The organic layer was dried over MgSO$_4$ filtered and excess dichloromethane removed under reduced pressure. The resulting residue was purified by flash chromatography (silica gel; 40:1 v/v DCM/MeOH to 20:1 v/v DCM/MeOH) to afford the product as a yellow solid (0.245 g, 60%). LC/MS (2.706 min (ES$^+$)), m/z: 721.5 ½[M+2H]$^+$.

(c) Compounds 19a-e (i) (9H-fluoren-9-yl)methyl(S)-1-((S)-1-((E)-3-((S)-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylamino)-1-oxopropan-2-ylamino)-3-methyl-1-oxobutan-2-ylcarbamate (19c)

SEM Fmoc amine 18c (0.212 g, 0.162 mmol, 1.0 eq.) was solubilised in THF (9.2 mL) and cooled to −78° C. under a nitrogen atmosphere. Super hydride solution (0.330 mL, 0.330 mmol, 2.04 eq.) was added drop wise over 4 minutes. After 45 minutes an aliquot was diluted with water and MeOH for LCMS After stirring for a further 10 mins, the reaction mixture was diluted with water (27 mL) and the cold bath removed. The organic layer was extracted with EtOAc (2×27 mL) and the combined organic extracts washed with brine (27 mL), dried over MgSO$_4$, filtered and concentrated under reduced pressure. The crude product was dissolved in MeOH (11.05 mL), DCM (5.53 mL) and water (1.85 mL) and enough silica gel was added to form a thick suspension which was left stirring for 5 days. The suspension was filtered and washed with DCM/MeOH 9:1 (~200 mL) until complete elution of product. The organic layer was washed with brine (2×70 mL), dried over MgSO$_4$, filtered and concentrated under reduced pressure. The resulting residue was purified by flash chromatography (silica gel; 40:1 v/v DCM/MeOH to 20:1 v/v DCM/MeOH) to afford the product as a yellow solid (0.060 g, 36%). LC/MS (2.802 min (ES$^+$)), m/z: 1016.15 [M+H]$^+$.

(ii) (9H-fluoren-9-yl)methyl(R)-1-((S)-1-((E)-3-((S)-7-methoxy-8-(3-((S)-7-methoxy-2-(4-(4-methylpiperazin-1-yl)phenyl)-5-oxo-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylamino)-1-oxopropan-2-ylamino)-3-methyl-1-oxobutan-2-ylcarbamate (19e)

SEM Fmoc amine 18e (0.245 g, 0.170 mmol, 1.0 eq) was solubilised in THF (10.6 mL) and cooled to −78° C. under a nitrogen atmosphere. Super hydride solution (0.347 mL, 0.347 mmol, 2.04 eq) was added drop wise over 4 minutes. After 45 minutes an aliquot was diluted with water and MeOH for LCMS After stirring for a further 10 minutes, the reaction mixture was diluted with water (35 mL) and the cold bath removed. The organic layer was extracted with EtOAc (2×35 mL) and the combined organic extracts washed with brine (35 mL), dried with MgSO$_4$, filtered and concentrated under reduced pressure. The crude material was dissolved in MeOH (12.8 mL), DCM (6.4 mL) and water (2.15 mL) and enough silica gel was added to form a thick suspension which was left stirring for 5 days. The suspension was filtered and washed with DCM/MeOH 9:1 (~200 mL) until complete elution of product. The organic layer was washed with brine (2×100 mL), dried over MgSO$_4$, filtered and concentrated under reduced pressure. The resulting residue was purified by flash chromatography (silica gel; 40:1 v/v DCM/MeOH to 20:1 v/v DCM/MeOH) to afford the product (0.100 g, 51%). LC/MS (2.117 min (ES$^+$)), m/z: 575.7 ½[M+2H]$^+$.

(a) Compounds 20a-e (i) (S)-2-amino-N—((S)-1-((E)-3-((S)-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylamino)-1-oxopropan-2-yl)-3-methylbutanamide (20c)

Piperidine (0.04 mL, 4.1 mmol, 13.7 eq.) was added to a stirring mixture of Fmoc amine 19c (0.030 g, 0.0295 mmol, 1 eq.) in anhydrous DMF (0.5 mL) and the mixture was stirred at ambient temperature. After 20 minutes, LCMS showed reaction was completed so the reaction mixture was diluted with DCM (75 mL) and washed with water (3×75 mL). The organic layer was dried over MgSO$_4$, filtered and concentrated to dryness under reduced pressure. Co-evaporation with n-hexanes afforded the product as a brown oil, and the material was not subjected to further purification (0.023 g, assumed 100%). LC/MS (1.868 min (ES$^+$)), m/z: 794.2 [M+H]$^+$.

(ii) (S)-2-amino-N—((S)-1-((E)-3-((S)-7-methoxy-8-(3-((S)-7-methoxy-2-(4-(4-methylpiperazin-1-yl)phenyl)-5-oxo-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylamino)-1-oxopropan-2-yl)-3-methylbutanamide (20e)

Piperidine (0.058 mL, 0.590 mmol, 12.0 eq.) was added to a stirring mixture of Fmoc amine 19e (0.050 g, 0.0492 mmol, 1.0 eq.) in anhydrous DMF (0.8 mL) and the mixture was stirred at ambient temperature. After 20 minutes, LCMS showed reaction was completed so the reaction mixture was diluted with DCM (30 mL) and washed with water (3×30 mL). The organic layer was dried over MgSO$_4$, filtered and concentrated to dryness under reduced pressure. Co-evaporation with n-hexanes afforded the product as a brown oil, and the material was not subjected to further purification (0.040 g, assumed 100%). LC/MS (1.533 min (ES$^+$)), m/z: 928.2 [M+H]$^+$.

(a) Compounds 21a-e (i) 1-(2-iodoacetamido)-N—((S)-1-((S)-1-((E)-3-((S)-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-5,11a-dihydro-1H-benzo[e]pyrrolo[1,2-a][1,4]diazepin-2-yl)allylamino)-1-oxopropan-2-ylamino)-3-methyl-1-oxobutan-2-yl)-3,6,9,12-tetraoxapentadecan-15-amide (21c)

2-Ethoxy-1-ethoxycarbonyl-1,2-dihydroquinoline (0.007 g, 0.0290 mmol, 1.0 eq) was added to a solution of amine 20c (assumed 100%, 0.023 g, 0.0290 mmol, 1.0 eq) and 1-iodo-2-oxo-6,9,12,15-tetraoxa-3-azaoctadecan-18-oic acid (I5) (0.0126 g, 0.0290 mmol, 1.0 eq) in dry dichloromethane (2 mL). The reaction mixture was stirred for 18 hours, then diluted with DCM (6 mL) and washed with water (2×10 mL). The organic layer was dried over MgSO$_4$, filtered and concentrated under reduced pressure. The resulting residue was subjected to flash chromatography (silica gel; 40:1 v/v DCM/MeOH to 5:1 v/v DCM/MeOH) to afford the product as a pale yellow oil (0.0043 g, 29%). LC/MS (2.380 min (ES$^+$)), m/z: 605.0 ½[M+2H]$^+$.

Example 4

Determination of In Vitro Cytotoxicity

Cells were plated in 150 μL growth media per well into black-sided clear-bottom 96-well plates (Costar, Corning) and allowed to settle for 1 hour in the biological cabinet before placing in the incubator at 37° C., 5% CO$_2$. The following day, 4× concentration of drug stocks were prepared, and then titrated as 10-fold serial dilutions producing 8-point dose curves and added at 50 μl per well in duplicate. Cells were then incubated for 48 hours at 37° C., 5% CO$_2$. Cytotoxicity was measure by incubating with 100 μL Cell Titer Glo (Promega) solution for 1 hour, and then luminescence was measured on a Fusion HT plate reader (Perkin Elmer). Data was processed with Excel (Microsoft) and GraphPad (Prism) to produce dose response curves and IC$_{50}$ values were generated and data collected.

| $IC_{50}$ (nM) | 786-O Caki-1 | L428 | MCF-7 |
|---|---|---|---|
| 4 | 0.2 0.0002 | 0.06 | 0.8 |

The invention claimed is:

1. A compound of formula I:

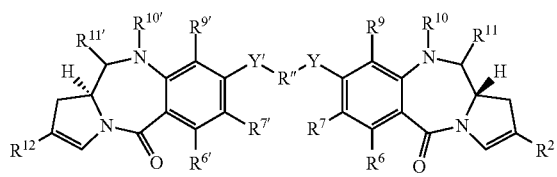

wherein:
R² is of formula II:

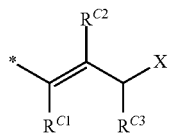

wherein X is selected from the group consisting of: OH, SH, CO₂H, COH, N=C=O, NHNH₂, CONHNH₂,

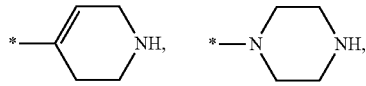 [SMILES: *C1=CCNCC1 ; *N1CCNCC1]

and NHR$^N$, wherein R$^N$ is selected from the group consisting of H and $C_{1-4}$ alkyl;
$R^{C1}$, $R^{C2}$ and $R^{C3}$ are independently selected from the group consisting of H and unsubstituted $C_{1-2}$ alkyl;
$R^{12}$ is selected from the group consisting of:
(ia) phenyl, naphthyl, and $C_{5-10}$ heteroaryl group, optionally substituted by one or more substituents selected from the group consisting of: halo, nitro, cyano, $C_{1-7}$ alkyloxy, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;
(id)

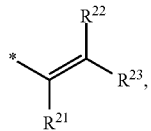

wherein each of $R^{21}$, $R^{22}$ and $R^{23}$ are independently selected from the group consisting of H, $C_{1-3}$ saturated alkyl, $C_{2-3}$ alkenyl, $C_{2-3}$ alkynyl and cyclopropyl, wherein the total number of carbon atoms in the $R^{12}$ group is no more than 5;
(ie)

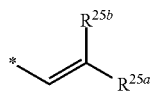

wherein one of $R^{25a}$ and $R^{25b}$ is H and the other is selected from the group consisting of: pyridyl, thiophenyl and phenyl, which phenyl is optionally substituted by a substituent selected from the group consisting of halo, methyl, and methoxy; and
(if)

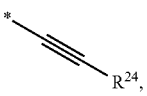

wherein $R^{24}$ is selected from the group consisting of: H $C_{1-3}$ saturated alkyl $C_{2-3}$ alkenyl $C_{2-3}$ alkynyl cyclopropyl pyridyl, thiophenyl and phenyl, which phenyl is optionally substituted by a substituent selected from the group consisting of halo, methyl, and methoxy;
$R^6$ and $R^9$ are H;
$R^7$ is a $C_{1-4}$ alkoxy group, optionally substituted by a $C_5$ heteroaryl or phenyl group; either:
(a) $R^{10}$ is H, and $R^{11}$ is OH, OR$^A$, wherein $R^A$ is $C_{1-4}$ alkyl;
(b) $R^{10}$ and $R^{11}$ form a nitrogen-carbon double bond between the nitrogen and carbon atoms to which they are bound or
(c) $R^{10}$ is H and $R^{11}$ is SO$_z$M, where z is 2 or 3 and M is a monovalent pharmaceutically acceptable cation;
R" is a $C_{3-12}$ alkylene group, optionally interrupted by one or more aromatic rings;
Y and Y' are selected from the group consisting of O, S, and NH;
$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, respectively, wherein if $R^{11}$ and $R^{11'}$ are SO$_z$M, each M is a monovalent pharmaceutically acceptable cation or together represent a divalent pharmaceutically acceptable cation,
wherein the term $C_{3-7}$ heterocyclyl refers to a monovalent moiety obtained by removing a hydrogen atom from a ring atom of a heterocyclic compounds which has from 3 to 7 ring atoms of which 1 to 4 are ring heteroatoms selected from the group consisting of N, O and S,
wherein the term $C_{5-10}$ heteroaryl refers to a monovalent moiety obtained by removing a hydrogen atom from a ring atom of a heteroaromatic compound which has from 5 to 10 ring atoms of which 1 to 4 are ring heteroatoms selected from the group consisting of N, O and S.

2. The compound according to claim 1, wherein Y is O and R" is $C_{3-7}$ alkylene.

3. The compound according to claim 1, wherein $R^{C1}$, $R^{C2}$ and $R^{C3}$ are independently selected from the group consisting of H and methyl.

4. The compound according to claim 1, wherein X is selected from the group consisting of OH, SH, CO₂H, —N=C=O and NH₂.

5. The compound according to claim 1, wherein $R^{12}$ is phenyl.

6. The compound according to claim 5, wherein $R^{12}$ bears one to three substituents selected from the group consisting of methoxy, ethoxy, fluoro, chloro, cyano, bis-oxy-methylene, methyl-piperazinyl, morpholino and methyl-thiophenyl.

7. The compound according to claim 1, wherein $R^{12}$ is selected from the group consisting of:

(i) methyl, ethyl or propyl;
(ii) cyclopropyl;
(iii) a group of formula:

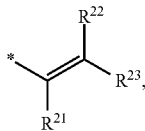

wherein each of $R^{21}$, $R^{22}$ and $R^{23}$ are independently selected from the group consisting of H, $C_{1-3}$ saturated alkyl, $C_{2-3}$ alkenyl, $C_{2-3}$ alkynyl and cyclopropyl, wherein the total number of carbon atoms in the $R^{12}$ group is no more than 4;

(iv) a group of formula:

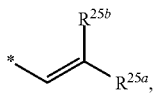

wherein one of $R^{25a}$ and $R^{25b}$ is H and the other is selected from the group consisting of: pyridyl, thiophenyl and phenyl, which phenyl is optionally substituted by a substituent selected from the group consisting of halo, methyl, and methoxy and (v) a arrow of formula:

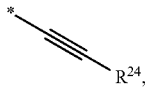

wherein $R^{24}$ is selected from the group consisting of H, methyl, ethyl, ethenyl and ethynyl.

8. The compound according to claim 1, wherein $R^{10}$ and $R^{11}$ form a nitrogen-carbon double bond.

9. The compound according to claim 1, wherein $R^{6'}$, $R^{7'}$, $R^{9'}$, $R^{10'}$, $R^{11'}$ and Y' are the same as $R^6$, $R^7$, $R^9$, $R^{10}$, $R^{11}$ and Y respectively.

10. A compound of formula IV:

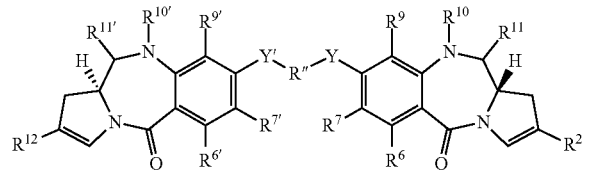

wherein:
$R^2$ is of formula II:

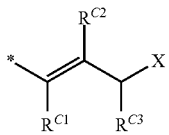

wherein X is selected from the group consisting of: OH, SH, $CO_2H$, COH, N=C=O, $NHNH_2$, $CONHNH_2$,

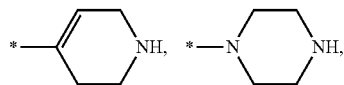

and $NHR^N$, wherein $R^N$ is selected from the group consisting of H and $C_{1-4}$ alkyl;
$R^{C1}$, $R^{C2}$ and $R^{C3}$ are independently selected from the group consisting of H and unsubstituted $C_{1-2}$ alkyl;
$R^{12}$ is selected from the group consisting of:
(ia) phenyl, naphthyl and $C_{5-10}$ heteroaryl group, optionally substituted by one or more substituents selected from the group consisting of: halo, nitro, cyano, $C_{1-7}$ alkyloxy, $C_{1-7}$ alkyl, $C_{3-7}$ heterocyclyl and bis-oxy-$C_{1-3}$ alkylene;
(ib) $C_{1-5}$ saturated aliphatic alkyl;
(ic) $C_{3-6}$ saturated cycloalkyl;
(id)

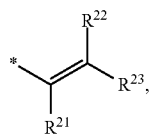

wherein each of $R^{21}$, $R^{22}$ and $R^{23}$ are independently selected from the group consisting of H, $C_{1-3}$ saturated alkyl, $C_{2-3}$ alkenyl, $C_{2-3}$ alkynyl and cyclopropyl, wherein the total number of carbon atoms in the $R^{12}$ group is no more than 5;
(ie)

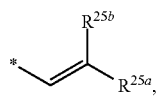

wherein one of $R^{25a}$ and $R^{25b}$ is H and the other is selected from the group consisting of: pyridyl, thiophenyl and phenyl, which phenyl is optionally substituted by a substituent selected from the group consisting of halo, methyl, and methoxy; and
(if)

wherein $R^{24}$ is selected from the group consisting of: H $C_{1-3}$ saturated alkyl $C_{2-3}$ alkenyl $C_{2-3}$ alkynyl cyclopropyl pyridyl, thiophenyl and phenyl, which phenyl is optionally substituted by a substituent selected from the group consisting of halo, methyl, and methoxy;
$R^6$ and $R^9$ are H;
$R^7$ is a $C_{1-4}$ alkoxy, optionally substituted by a $C_5$ heteroaryl or phenyl group;
R" is a $C_{3-12}$ alkylene group, optionally interrupted by one or more aromatic rings;
Y and Y' are selected from the group consisting of O, S, and NH;

$R^{6'}$, $R^{7'}$, $R^{9'}$ are selected from the same groups as $R^6$, $R^7$ and $R^9$ respectively;

and either:
- (a) $R^{10}$ is a carbamate nitrogen protecting group, and $R^{11}$ is O-Prot$^O$, wherein Prot$^O$ is an oxygen protecting group;
- (b) $R^{10}$ is a hemi-aminal nitrogen protecting group and $R^{11}$ is an oxo group; and $R^{10'}$ and $R^{11'}$ are the same as $R^{10}$ and $R^{11}$, respectively;

wherein the term $C_{3-7}$ heterocyclyl refers to a monovalent moiety obtained by removing a hydrogen atom from a ring atom of a heterocyclic compounds which has from 3 to 7 ring atoms of which 1 to 4 are ring heteroatoms selected from the group consisting of N, O and S, wherein the term $C_{5-10}$ heteroaryl refers to a monovalent moiety obtained by removing a hydrogen atom from a ring atom of a heteroaromatic compound which has from 5 to 10 ring atoms of which 1 to 4 are ring heteroatoms selected from the group consisting of N, O and S.

11. A compound according to claim 10, wherein $R^{10}$ is Troc, and $R^{11}$ is OTBS.

12. A compound according to claim 10, wherein $R^{11}$ is oxo and $R^{1o}$ is SEM.

13. A Conjugate having formula III:

L-(LU-D)$_p$     (III)

wherein L is a Ligand unit selected from the group consisting of an antibody and an antigen-binding fragment of an antibody, LU is a Linker unit which is -$A^1$-$L^1$-, wherein $A^1$ is selected from the group consisting of:

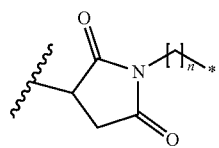

wherein the asterisk indicates the point of attachment to $L^1$, the wavy line indicates the point of attachment to the Ligand unit, and n is 0 to 6;

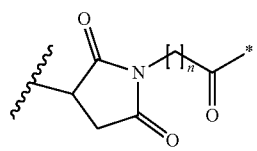

wherein the asterisk indicates the point of attachment to $L^1$, the wavy line indicates the point of attachment to the Ligand unit, and n is 0 to 6;

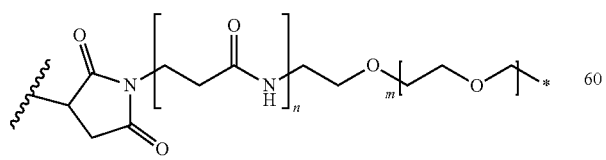

wherein the asterisk indicates the point of attachment to $L^1$, the wavy line indicates the point of attachment to the Ligand unit, n is 0 or 1, and m is 0 to 30; and

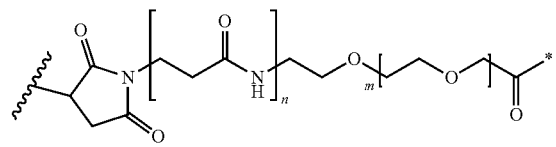

wherein the asterisk indicates the point of attachment to $L^1$, the wavy line indicates the point of attachment to the Ligand unit, n is 0 or 1, and m is 0 to 30;

wherein in each of the above $A^1$ formulae the maleimide-derived group is optionally replaced by —NH—C(O)—CH$_2$—; and $L^1$ is an amino acid sequence which is cleavable by the action of an enzyme p is 1 to 20; and D is a Drug unit of formula I:

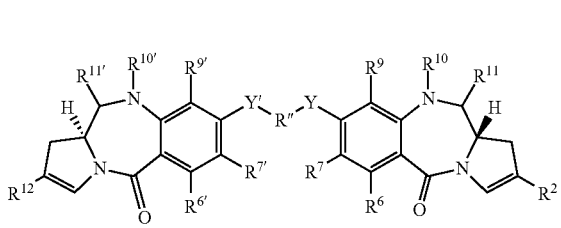

wherein:

$R^2$ is of formula II:

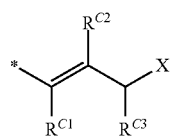

wherein X is selected from the group consisting of:
*—O—$^+$, *—S—$^+$, *—CO$_2$—$^+$, *—CO—$^+$, *—NH(C=O)—$^+$, *—NHNH—$^+$, *—CONHNH—$^+$,

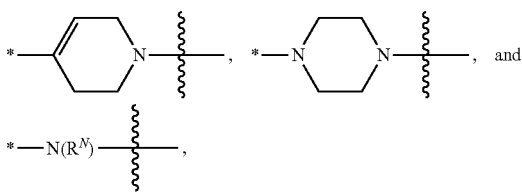

wherein $R^N$ is selected from the group comprising H and $C_{1-4}$ alkyl, and the asterisk indicates the point of attachment to the remainder of the Drug unit and the wavy line or $^+$ indicates the point of attachment to the Linker Unit;

$R^{C1}$, $R^{C2}$ and $R^{C3}$ are independently selected from the group consisting of H and unsubstituted $C_{1-2}$ alkyl;

$R^{12}$ is selected from the group consisting of:
- (ia) phenyl, naphthyl, and $C_{5-10}$ heteroaryl group, optionally substituted by one or more substituents selected from the group consisting of: halo, nitro, cyano, $C_{1-7}$ alkyloxy, $C_{1-7}$ alkyl, $C_{3-7}$ heterocyclyl and bis-oxy-$C_{1-3}$ alkylene;

(ib) $C_{1-5}$ saturated aliphatic alkyl;
(ic) $C_{3-6}$ saturated cycloalkyl;
(id)

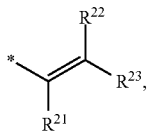

wherein each of $R^{21}$, $R^{22}$ and $R^{23}$ are independently selected from the group consisting of H, $C_{1-3}$ saturated alkyl, $C_{2-3}$ alkenyl, $C_{2-3}$ alkynyl and cyclopropyl, wherein the total number of carbon atoms in the $R^{12}$ group is no more than 5;
(ie)

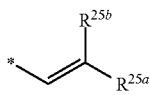

wherein one of $R^{25a}$ and $R^{25b}$ is H and the other is selected from the group consisting of: pyridyl, thiophenyl and phenyl, which phenyl is optionally substituted by a substituent selected from the group consisting of halo, methyl, and methoxy; and
(if)

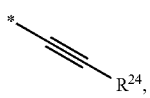

wherein $R^{24}$ is selected from the group consisting of: H $C_{1-3}$ saturated alkyl $C_{2-3}$ alkenyl $C_{2-3}$ alkynyl cyclopropyl, pyridyl, thiophenyl and phenyl, which phenyl is optionally substituted by a group selected from halo, methyl, and methoxy;
$R^6$ and $R^9$ are H;
$R^7$ is a $C_{1-4}$ alkoxy group, optionally substituted by a $C_5$ heteroaryl or phenyl group; either:
  (a) $R^{10}$ is H, and $R^{11}$ is OH, $OR^A$, wherein $R^A$ is $C_{1-4}$ alkyl;
  (b) $R^{10}$ and $R^{11}$ form a nitrogen-carbon double bond between the nitrogen and carbon atoms to which they are bound; or
  (c) $R^{10}$ is H and $R^{11}$ is $SO_zM$, where z is 2 or 3 and M is a monovalent pharmaceutically acceptable cation;
R" is a $C_{3-12}$ alkylene group, optionally interrupted by one or more aromatic rings;
Y and Y' are selected from the group consisting of O, S, and NH;
$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, respectively, wherein if $R^{11}$ and $R^{11'}$ are $SO_zM$, each M is a monovalent pharmaceutically acceptable cation or together represent a divalent pharmaceutically acceptable cation,
wherein the term $C_{3-7}$ heterocyclyl refers to a monovalent moiety obtained by removing a hydrogen atom from a ring atom of a heterocyclic compounds which has from 3 to 7 ring atoms of which 1 to 4 are ring heteroatoms selected from the group consisting of N, O and S, wherein the term $C_{5-10}$ heteroaryl refers to a monovalent moiety obtained by removing a hydrogen atom from a ring atom of a heteroaromatic compound which has from 5 to 10 ring atoms of which 1 to 4 are ring heteroatoms selected from the group consisting of N, O and S.

14. The Conjugate of claim 13, wherein $A^1$ is

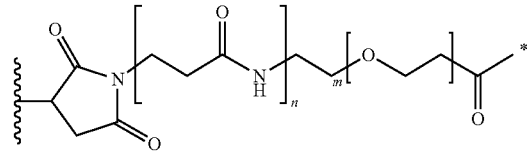

wherein the asterisk indicates the point of attachment to $L^1$, the wavy line indicates the point of attachment to the Ligand unit, n is 0 or 1, and m is 0 to 30 and wherein in the above $A^1$ formula the maleimide-derived group is optionally replaced by $-NH-C(O)-CH_2-$.

15. The Conjugate of claim 13, wherein $L^1$ is selected from the group consisting of valine-alanine, valine-citrulline and phenylalanine-lysine.

16. A drug linker of formula V:

LU-D     (V)

or a pharmaceutically acceptable salt, wherein LU is a Linker unit which is $G^1-L^1$, wherein $G^1$ is selected from the group consisting of:

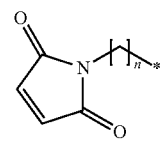

wherein the asterisk indicates the point of attachment to $L^1$ and n is 0 to 6;

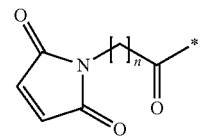

wherein the asterisk indicates the point of attachment to $L^1$ and n is 0 to 6;

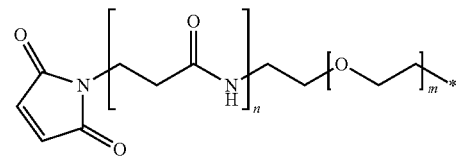

wherein the asterisk indicates the point of attachment to $L^1$, n is 0 or 1, and m is 0 to 30;

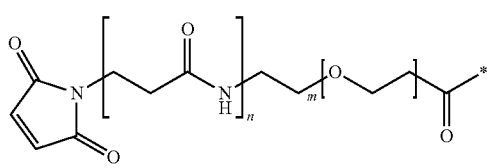

wherein the asterisk indicates the point of attachment to $L^1$, n is 0 or 1, and m is 0 to 30;

and wherein in each of the above $L^1$ formulae the maleimide moiety is optionally replaced by —NH—C(O)—CH$_2$X, wherein X is Cl, Br or I, $L^1$ is an amino acid sequence which is cleavable by the action of an enzyme and wherein D is of formula I:

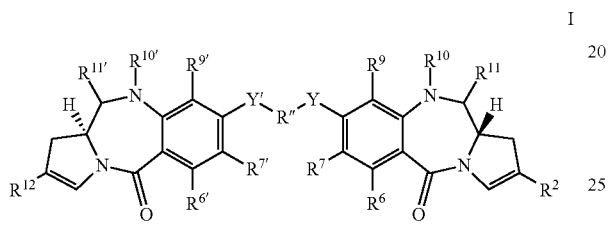

wherein:
$R^2$ is of formula II:

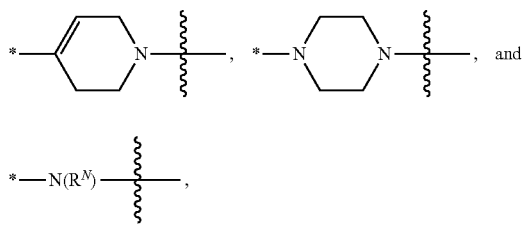

where in X is selected from the group consisting of $*\text{—O—}^q$, $*\text{—S—}^q$, $*\text{—CO}_2\text{—}^q$, $*\text{—CO—}^q$, —NH(C=O)—$^q$, $*$—NHNH—$^q$, $*$—CONHNH—$^q$,

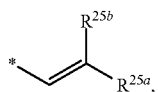, and

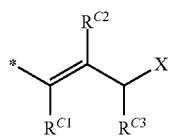, wherein $R^N$ is selected from the group consisting of H and $C_{1-4}$ alkyl, and the asterisk indicates the point of attachment to the remainder of the Drug unit and the wavy line or q indicates the point of attachment to the Linker Unit;

$R^{C1}$, $R^{C2}$ and $R^{C3}$ are independently selected from the group consisting of H and unsubstituted $C_{1-2}$ alkyl;

$R^{12}$ is selected from the group consisting of:
(ia) phenyl, naphthyl, and $C_{5-10}$ heteroaryl group, optionally substituted by one or more substituents selected from the group consisting of: halo, nitro, cyano, $C_{1-7}$ alkyloxy, $C_{1-7}$ alkyl, $C_{3-7}$ heterocyclyl and bis-oxy-$C_{1-3}$ alkylene;

(ib) $C_{1-5}$ saturated aliphatic alkyl;
(ic) $C_{3-6}$ saturated cycloalkyl;
(id)

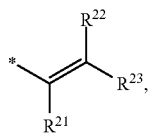

wherein each of $R^{21}$, $R^{22}$ and $R^{23}$ are independently selected from the group consisting of H, $C_{1-3}$ saturated alkyl, $C_{2-3}$ alkenyl, $C_{2-3}$ alkynyl and cyclopropyl, wherein the total number of carbon atoms in the $R^{12}$ group is no more than 5;

(ie)

wherein one of $R^{25a}$ and $R^{25b}$ is H and the other is selected from the group consisting of: pyridyl, thiophenyl and phenyl, which phenyl is optionally substituted by a substituent selected from the group consisting of halo, methyl, and methoxy; and (if)

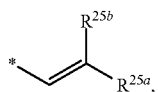

wherein $R^{24}$ is selected from the group consisting of: H $C_{1-3}$ saturated alkyl $C_{2-3}$ alkenyl $C_{2-3}$ alkynyl cyclopropyl pyridyl, thiophenyl and phenyl, which phenyl is optionally substituted by a substituent selected from the group conisting of halo, methyl, and methoxy;

$R^6$ and $R^9$ are H;
$R^7$ is $C_{1-4}$ alkoxy group, optionally substituted by a $C_5$ heteroaryl or phenyl group; either:
(a) $R^{10}$ is H, and $R^{11}$ is OH, OR$^A$, wherein $R^A$ is $C_{1-4}$ alkyl;
(b) $R^{10}$ and $R^{11}$ form a nitrogen-carbon double bond between the nitrogen and carbon atoms to which they are bound; or
(c) $R^{10}$ is H and $R^{11}$ is SO$_z$M, wherein z is 2 or 3 and M is a monovalent pharmaceutically acceptable cation;

R" is a $C_{3-12}$ alkylene group, optionally interrupted by one or more aromatic rings;

Y and Y' are selected from the group consisting of O, S, and NH;

$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, respectively, wherein if $R^{11}$ and $R^{11'}$ are SO$_z$M, each M is a monovalent pharmaceutically acceptable cation or together represent a divalent pharmaceutically acceptable cation, wherein the term $C_{3-7}$ heterocyclyl refers to a monovalent moiety obtained by removing a hydrogen atom from a ring atom of a heterocyclic compounds which has from 3 to 7 ring atoms of which 1 to 4 are ring heteroatoms selected from the group consisting of N, O and S, wherein the term $C_{5-10}$ heteroaryl refers to a monovalent moiety obtained by removing a hydrogen atom from a ring atom of a heteroaromatic compound which has from 5 to 10 ring atoms of which 1 to 4 are ring heteroatoms selected from the group consisting of N, O and S.

17. A method of treating a mammal having a proliferative disease, comprising administering an effective amount of the Conjugate of claim 13 to a subject in need thereof, wherein the proliferative disease treated is selected from the group consisting of kidney cancer, Hodgkin Lymphoma and breast cancer.

\* \* \* \* \*